United States Patent
Shapiro

(10) Patent No.: US 10,030,026 B2
(45) Date of Patent: Jul. 24, 2018

(54) DIFLUOROETHYLPYRIDINE DERIVATIVES AS NR2B NMDA RECEPTOR ANTAGONISTS

(71) Applicant: Rugen Holdings (Cayman) Limited, Grand Cayman (KY)

(72) Inventor: Gideon Shapiro, Gainesville, FL (US)

(73) Assignee: Rugen Holdings (Cayman) Limited, Grand Cayman (KY)

( * ) Notice: Subject to any disclaimer, the term of this patent is extended or adjusted under 35 U.S.C. 154(b) by 0 days.

(21) Appl. No.: 15/315,812

(22) PCT Filed: Jun. 3, 2015

(86) PCT No.: PCT/US2015/034009
§ 371 (c)(1),
(2) Date: Dec. 2, 2016

(87) PCT Pub. No.: WO2015/187845
PCT Pub. Date: Dec. 10, 2015

(65) Prior Publication Data
US 2017/0101412 A1    Apr. 13, 2017

Related U.S. Application Data

(60) Provisional application No. 62/007,762, filed on Jun. 4, 2014.

(51) Int. Cl.
*A01N 43/90* (2006.01)
*A61K 31/519* (2006.01)
*C07D 487/04* (2006.01)

(52) U.S. Cl.
CPC .......... *C07D 487/04* (2013.01); *A61K 31/519* (2013.01)

(58) Field of Classification Search
CPC ............................ C07D 487/04; A61K 31/519
USPC ....................................... 514/262.1; 544/262
See application file for complete search history.

(56) References Cited

U.S. PATENT DOCUMENTS

| | | |
|---|---|---|
| 7,592,360 B2 | 9/2009 | Liverton et al. |
| 9,567,341 B2 | 2/2017 | Shapiro |
| 2016/0075713 A1 | 3/2016 | Shapiro |
| 2017/0209449 A1 | 7/2017 | Shapiro |

FOREIGN PATENT DOCUMENTS

| | | |
|---|---|---|
| WO | WO-2004/108705 A1 | 12/2004 |
| WO | WO-2006/113471 A2 | 10/2006 |
| WO | WO-2010/015637 A1 | 2/2010 |
| WO | WO-2014/120800 A1 | 8/2014 |
| WO | WO-2015/187845 A1 | 12/2015 |
| WO | WO-2016/044323 A1 | 3/2016 |

OTHER PUBLICATIONS

Addy, C. et al., Single-dose administration of MK-0657, an NR2B-selective NMDA antagonist, does not result in clinically meaningful improvement in motor function in patients with moderate Parkinson's disease, J Clin Pharmacol, 49(7):856-864 (2009).
Bandyopadhyay, S. and Hablitz, J., NR2B antagonists restrict spatiotemporal spread of activity in a rat model of cortical dysplasia, Epilepsy Research, 72:127-139 (2006).
Barton, M. et al., Pharmacological characterization of the 6 Hz psychomotor seizure model of partial epilepsy, Epilepsy Res, 47(3):217-227 (2001).
Bausch, S. et al., Inverse relationship between seizure expression and extrasynaptic NMDAR function following chronic NMDAR inhibition, Epilepsia, 51(Suppl 3):102-105 (2010).
Beinat, C. et al., Current Medicinal Chemistry, 17:4166-4190 (2010).
Berge, S. et al., Pharmaceutical salts, J Pharm Sci, 66(1):1-19 (1977).
Borza, I. and Dománily, G., NR2B selective NMDA antagonists: the evolution of the ifenprodil-type pharmacophore, Curr Top Med Chem, 6(7):687-695 (2006).
Brown, W. et al., Comparative assay of an antiepileptic drugs by psychomotor seizure test and minimal electroshock threshold test, J Pharmacol Exp Ther, 107(3):273-283 (1953).
Castel-Branco, M. et al., The maximal electroshock seizure (MES) model in the preclinical assessment of potential new antiepileptic drugs, Methods Find Exp Clin Pharmacol, 31(2):101-106 (2009).
Chenard, B. et al., (1S,2S)-1-(4-hydroxyphenyl)-2-(4-hydroxy-4-phenylpiperidino)-1-propanol: a potent new neuroprotectant which blocks N-methyl-D-aspartate responses, J Med Chem, 38(16):3138-3145 (1995).
Chermat and Simon, Fiche Technique, Journal of Pharmacology, 6:494-496 (1975).
Cull-Candy, S. et al., NMDA receptor diversity in the cerebellum: identification of subunits contributing to functional receptors, Neuropharmacology, 37(10-11):1369-1380 (1998).
Curran, H. and Morgan, C., Cognitive, dissociative and psychotogenic effects of ketamine in recreational users on the night of drug use and 3 days later, Addiction, 95(4):575-590 (2000).

(Continued)

Primary Examiner — Jeffrey H Murray
(74) Attorney, Agent, or Firm — Choate, Hall & Stewart LLP; Kristen C. Buteau

(57) ABSTRACT

Disclosed are chemical entities of formula (I) wherein X, Y, Z, $R^1$, $R^3$, $R^4$, $R^5$ and $R^6$ are defined herein, as NR2B subtype selective receptor antagonists. Also disclosed are pharmaceutical compositions comprising a chemical entity of formula (I), and methods of treating various diseases and disorders associated with NR2B antagonism, e.g., diseases and disorders of the CNS, such as depression, by administering a chemical entity of formula I.

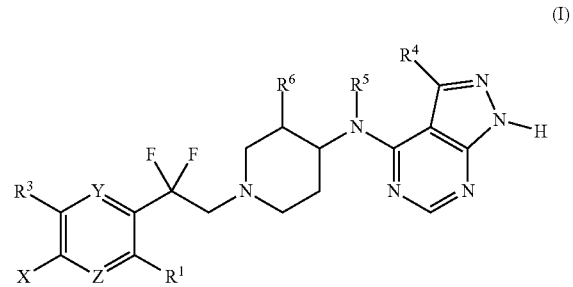

(I)

20 Claims, 2 Drawing Sheets

(56) References Cited

OTHER PUBLICATIONS

Dalby, N. and Nielsen, E., Comparison of the preclinical anticonvulsant profiles of tiagabine, lamotrigine, gabapentin and vigabatrin, Epilepsy Res, 28(1):63-72 (1997).
Damasio, Antonio R., Alzheimer's Disease and Related Dementias, Cecil Textbook of Medicine, 20th Edition, 2:1992-1996 (1996).
Esneault, E. et al., Evaluation of pro-convulsant risk in the rat: spontaneous and provoked convulsions, J Pharmacol Toxicol Methods, 72:59-66 (2015).
Fischer, G. et al., Ro 25-6981, a highly potent and selective blocker of N-methyl-D-aspartate receptors containing the NR2B subunit, Characterization in vitro, J Pharmacol Exp Ther, 283(3):1285-1292 (1997).
Fisher, R. et al., Epileptic seizures and epilepsy: definitions proposed by the International League Against Epilepsy (ILAE) and the International Bureau for Epilepsy (IBE), Epilepsia, 46(4):470-472 (2005).
Giannini, A. James et al., Phencyclidine and the Dissociativese, Psychiatric Medicine, 3:197-217 (1985).
Haas, D. and Harper, D., Ketamine: a review of its pharmacologic properties and use in ambulatory anesthesia, Anesth Prog, 39(3):61-68 (1992).
Hancox, J. and James, A., Refining insights into high-affinity drug binding to the human ether-à-go-go-related gene potassium channel, Mol Pharmacol, 73(6):1592-1595 (2008).
Hansen, K. et al., Pharmacological characterization of ligands at recombinant NMDA receptor subtypes by electrophysiological recordings and intracellular calcium measurements, Comb Chem High Throughput Screen, 11(4):304-315 (2008).
Hardy, J. et al., Randomized, double-blind, placebo-controlled study to assess the efficacy and toxicity of subcutaneous ketamine in the management of cancer pain, J Clin Oncol, 30(29):3611-3617 (2012).
Ibrahim, L. et al., Randomized, placebo-controlled, crossover pilot trial of the oral selective NR2B antagonist MK-0657 in patients with treatment-resistant major depressive disorder, J Clin Psychopharmacol, 32(4):551-557 (2012).
International Search Report for PCT/US2015/034009, 3 pages (dated Sep. 30, 2015).
International Search Report for PCT/US2015/050267, 4 pages (dated Dec. 9, 2015).
Jordan, V. Craig, Tamoxifen: A Most Unlikely Pioneering Medicine, Nature Reviews: Drug Discovery, 2(3):205-213 (2003).
Katalinic, N. et al., Ketamine as a new treatment for depression: a review of its efficacy and adverse effects, Aust N Z J Psychiatry, 47(8):710-727 (2013).
Kawai, M. et al., Discovery of novel and orally active NR2B-selective N-methyl-d-aspartate (NMDA) antagonists, pyridinol derivatives with reduced HERG binding affinity, Bioorg Med Chem Lett, 17(20):5533-5536 (2007).
Layton, M. et al., Recent advances in the development of NR2B subtype-selective NMDA receptor antagonists, Curr Top Med Chem, 6(7):697-709 (2006).
Lemke, J. et al., GRIN2B Mutations in West Syndrome and Intellectual Disability with Focal Epilepsy, Ann Neurol, 75:147-154 (2014).
Liverton, N. et al., Identification and characterization of 4-methylbenzyl 4-[(pyrimidin-2-ylamino)methyl]piperidine-1-carboxylate, an orally bioavailable, brain penetrant NR2B selective N-methyl-D-aspartate receptor antagonist, J Med Chem, 50(4):807-819 (2007).
Lucki , I. et al., Sensitivity to the effects of pharmacologically selective antidepressants in different strains of mice, Psychopharmacology (Berl), 155(3):315-322 (2001).
Mares, Pavel, Age and activation determines the anticonvulsant effect of ifenprodil in rats, Naunyn-Schmiedeberg's Arch Pharmacol, 387:753-761 (2014).
Mathews, D. and Zarate, C., Current status of ketamine and related compounds for depression, J Clin Psychiatry, 74(5):516-517 (2013).
Menniti, F. et al., CP-101,606: An NR2B- Selective NMDA Receptor Antagonist, CNS Drug Reviews, 4(4):307-322 (1998).
Mony, L. et al., Allosteric modulators of NR2B-containing NMDA receptors: molecular mechanisms and therapeutic potential, Br J Pharmacol, 157(8):1301-1317 (2009).
Murrough, J. et al., Antidepressant efficacy of ketamine in treatment-resistant major depression: a two-site randomized controlled trial, Am J Psychiatry, 170(10):1134-1142 (2013).
Neligan, et al., The epidemiology of the epilepsies, Handb Clin Neurol, 107:113-133 (2012).
Nielsen, D. et al., Antidepressant-like activity of corticotropin-releasing factor type-1 receptor antagonists in mice, European Journal of Pharmacology, 499:135-146 (2004).
Noppers, I. et al., Drug-induced liver injury following a repeated course of ketamine treatment for chronic pain in CRPS type 1 patients: a report of 3 cases, Pain, 152(9):2173-2178 (2011).
Paoletti, P. et al., NMDA receptor subunit diversity: impact on receptor properties, synaptic plasticity and disease, Nat Rev Neurosci, 14(6):383-400 (2013).
Porsolt, R. et al., Behavioral despair in mice: a primary screening test for antidepressants, Arch Int Pharmacodyn Ther, 229(2):327-336 (1977).
Reynolds, I. and Miller, R., Ifenprodil is a novel type of N-methyl-D-aspartate receptor antagonist: interaction with polyamines, Mol Pharmacol, 36(5):758-765 (1989).
Ruppa, K. et al., NMDA Antagonists of GluN2B Subtype and Modulators of GluN2A, GluN2C, and GluN2D Subtypes—Recent Results and Developments, Annual Reports in Medicinal Chemistry, 47:89-103 (2012).
Sanacora, G. et al., Targeting the glutamatergic system to develop novel, improved therapeutics for mood disorders, Nat Rev Drug Discov, 7(5):426-437 (2008).
Steece-Collier, K. et al., Antiparkinsonian actions of CP-101,606, an antagonist of NR2B subunit-containing N-methyl-d-aspartate receptors, Exp Neurol, 163(1):239-243 (2000).
Swinyard, E. et al., Comparative assays of antiepileptic drugs in mice and rats, J Pharmacol Exp Ther, 106(3):319-330 (1952).
Szczurowska, E. and Mares, P., Different action of a specific NR2B/NMDA antagonist Ro 25-6981 on cortical evoked potentials and epileptic afterdischarges in immature rats, Brain Research Bulletin, 111:1-8 (2015).
Traynelis, S. et al., Glutamate receptor ion channels: structure, regulation, and function, Pharmacol Rev, 62(3):405-496 (2010).
Written Opinion for PCT/US2015/034009, 6 pages (dated Sep. 30, 2015).
Written Opinion for PCT/US2015/050267, 5 pages (dated Dec. 9, 2015).
Zarate, C. et al., A randomized trial of an N-methyl-D-aspartate antagonist in treatment-resistant major depression, Arch Gen Psychiatry, 63(8):856-864 (2006).
Zarate, C. et al., Replication of ketamine's antidepressant efficacy in bipolar depression: a randomized controlled add-on trial, Biol Psychiatry, 71(11):939-946 (2012).
Boyce-Rustay, J.M. and Holmes, A., Functional Roles of NMDA Receptor NR2A and NR2B Subunits in the Acute Intoxicating Effects of Ethanol in Mice, Synapse, 56:222-225 (2005).
Brown, D. et al., 2,6-Disubstituted pyrazines and related analogs as NR2B site antagonists of the NMDA receptor with anti-depressant activity, Bioorg Med Chem Lett, 21(11):3399-3403 (2011).
Chen, M. et al., Differential Roles of NMDA Receptor Subtypes in Ischemic Neuronal Cell Death and Ischemic Tolerance, Stroke, 39:3042-3048 (2008).
Garner, R. et al., Preclinical pharmacology and pharmacokinetics of CERC-301, a GluN2B-selective N-methyl-D-aspartate receptor antagonist, Pharmacology Research & Perspectives, 3(6):e00198 (2015).
Ghasemi, M. and Schachter, S.C., The NMDA receptor complex as a therapeutic target in epilepsy: a review, Epilepsy & Behavior, 22:617-640 (2011).
Jimenez-Sanchez, L. et al., The Role of GluN2A and GluN2B Subunits on the Effect of NMDA Receptor Antagonists in Modeling Schizophrenia and Treating Refractory Depression, Neuropsychopharmacology, 39:2673-2680 (2014).

(56) References Cited

OTHER PUBLICATIONS

Kao, J. et al., NR2B subunit of NMDA receptor at nucleus accumbens is involved in morphine rewarding effect by siRNA study, Drug and Alcohol Dependence, 118:366-374 (2011).

Kong, M. et al., NR2B antagonist CP-101,606 inhibits NR2B phosphorylation at tyrosine-1472 and its interactions with Fyn in levodopa-induced dyskinesia rat model, Behavioural Brain Research, 282:46-53 (2015).

Konitsiotis, S. et al., Effects of N-methyl-D-aspartate receptor antagonism on neuroleptic-indeuced orofacial dyskinesias, Physchopharmacology, 185:369-377 (2006).

Layton, M.E. et al., Discovery of 3-Substituted Aminocyclopentances as Potent and Orally Bioavailable NR2B Subtype-Selective NMDA Antagonists, ACS Chem. Neurosci., 2:352-362 (2011).

Li, L. et al., Role of NR2B-type NMDA receptors in selective neurodegeneration in Huntington disease, Neurobiology of Aging, 24:1113-1121 (2003).

Lima-Ojeda, J.M. et al., Pharmacological blockad of GluN2B-containing NMDA reeptors induces antidepressant-like effects lacking psychotomimetic action and neurotoxicity in the perinatal and adult rodent brain, Progress in Neuro-Psychopharmacology & Biological Psychiatry, 45:28-33 (2013).

Liverton, N.J. et al., Identification and Characterization of 4-Methylbenzyl 4-[(Pyrimidin-2-ylamino)methyl]piperidine-1-carboxylate, an Orally Bioavailable, Brain Penetrant NR2B Selective N-Methyl-D-Aspartate Receptor Antagonist, J. Med. Chem., 50:807-819 (2007).

Mares, P. and Mikulecka, A., Different effects of two N-methyl-D-aspartate receptor antagonists on seizures, spontaneous behavior, and motor performance in immature rats, Epilepsy & Behavior, 14:32-39 (2009).

Mares, P., Age and activation determines the anticonvulsant effect in ifenprodil in rats, Naunyn-Schmiedeberg's Arch Pharmacol, 387:753-761 (2014).

Menniti, F.S. et al., CP-101,606, an NR2B subunit selective NMDA receptor antagonist, inhibits NMDA and injury induced c-fos expression and corticol spreading depression in rodents, Neurpharmacology, 39:1147-1155 (2000).

Naspolini, A.P. et al., Traxoprodil decreases pentylenetetrazol-induced seizures, Epilepsy Research, 100:12-19 (2012).

Niesters, M. et al., Ketamine for chronic pain: risks and benefits, British Journal of Clinical Pharmacology, 77(2):357-367 (2013).

Nutt, J.G. et al., Effects of NR2B Selective NMDA Glutamate Antagonist, CP-101,606, on Dyskinesia and Parkinsonism, Movement Disorders, 23(13):1860-1866 (2008).

Peeters, M. et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, 321(2):564-572 (2007).

Preskorn, S. et al., An innovative design to establish proof of concept of the antidepressant effects of the NR2B subunit selective N-methyl-D-aspartate antagonist, CP-101,606, in patients with treatment-refractory major depressive disorder, J Clin Psychopharmacol, 28(6):631-637 (2008).

Sang, C.N. et al., The NR2B subunit-selective NMDA receptor antagonist, CP-101,606, reduces spontaneous pain intensity in patients with central and peripheral neuropathic pain, Society for Neuroscience, Abstract 814.9 (2003).

Shehadeh, J. et al., Striatal neuronal apoptosis is preferentially enhanced by NMDA receptor activation in YAC transgenic mouse model of Huntington disease, Neurobiology of Disease, 21:392-403 (2006).

Szczurowska, E. and Mares, P., Different action of a specific NR2B/NMDA antagonist Ro 25-6981 on corticol evoked potentials and epileptic afterdischarges in immature rats, Brain Research Bulletin, 111:1-8 (2015).

Tahirovic, Y.A. et al., Enantiomeric Propanolamines as selective N-Methyl-D-aspartate 2B Receptor Antagonists, J. Med. Chem., 51:5506-5521 (2008).

Taniguchi, K. et al., Antinociceptive activity of CP-101,606 an NMDA receptor NR2B subunit antagonist, British Journal of Pharmacology, 122:809-812 (1997).

Vengeliene, V. et al., The role of the NMDA receptor in alcohol relapse: a pharmacological mapping study using the alcohol deprivation effect, Neuropharmacology, 48:822-829 (2005).

Wang, H. et al., pH-Sensitive NMDA Inhibitors Improve Outcome in a Murine Model of SAH, Neurocrit Care, 21:119-131 (2014).

Wang, X.M. and Bausch, S.B., Effects of distinct classes of N-methyl-D-aspartate receptor antagonist on seizures, axonal sprouting and neuronal loss in vitro: suppression by NR2B-selective antagonists, Neuropharmacology, 47:1008-1020 (2004).

Warraich, S.T. et al., Evaluation of behavioural effects of a selective NMDA NR1A/2B receptor antagonist in the unilateral 6-OHDA lesion rat model, Brain Research Bulletin, 79:85-90 (2009).

Wessel, R.H. et al., NR2B selective NMDA receptor antagonist CP-101,606 prevents levodopa-induced motor response alterations in hemi-parkinsonian rats, Neuropharmacology, 47:184-194 (2004).

Xie, X. et al., Role of a Hippocampal Src-Family Kinase-Mediated Glutamatergic Mechanism in Drug Context-Induced Cocaine Seeking, Neuropsychopharmacology, 38:2657-2665 (2013).

Yuan, H. et al., Context-Dependent GluN2B-Selective Inhibitors of NMDA Receptor Function Are Neuroprotective with Minimal Side Effects, Neuron, 85:1305-1318 (2015).

Zeron, M.M. et al., Increased Sensitivity to N-Methyl-D-Aspartate Receptor-Mediated Excitotoxicity in a Mouse Model of Huntington's Disease, Neuron, 33:849-860 (2002).

DIFLUOROETHYLPYRIDINE DERIVATIVES AS NR2B NMDA RECEPTOR ANTAGONISTS

BACKGROUND

Non-selective NMDA receptor antagonists, originally developed in stroke and head trauma, have more recently shown clinical efficacy in treating depression. The non-selective NMDA receptor antagonist, ketamine, has been shown to have rapid onset and efficacy in depression resistant to standard monoamine reuptake inhibitor therapy (Mathews and Zarate, 2013, *J. Clin. Psychiatry* 74:516-158). However, non-selective NMDA receptor antagonists such as ketamine have a range of undesirable pharmacological activities which limit application in humans. In particular dissociative or psychogenic side effects are particularly prominent for non-selective NMDA receptor antagonists. More recently, NR2B subtype selective NMDA receptor antagonists have demonstrated potential in a wide range of clinical indications. In particular, NR2B antagonists have also demonstrated antidepressant activity in early stage clinical trials (Ibrahim et al., 2012, *J. Clin. Psychopharmacol.* 32, 551-557; Preskorn et al., 2008, *J. Clin. Psychopharmacol.* 28, 631-637). Furthermore, selective NR2B antagonists have advantages over unselective NMDA receptor antagonists such as ketamine due to greatly diminished dissociative side effects. However, NR2B antagonists described to date have generally exhibited drawbacks with regard to other drug properties which have limited potential use in human drug therapy.

SUMMARY

For broad scope of application and safe human use in a range of clinical indications including depression, improved NR2B subtype selective antagonists are needed. The present invention, among other things, addresses the need for NR2B receptor antagonists that are improved in one or more aspects exemplified by pharmacokinetic performance, oral activity, cardiovascular safety, and in vitro and in vivo therapeutic safety index measures.

In some embodiments, the present invention encompasses the insight that chemical entities of formula I:

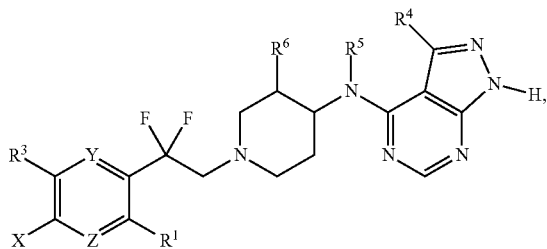

I wherein X, Y, Z, $R^1$, $R^3$, $R^4$, $R^5$ and $R^6$ are defined herein, are NR2B subtype selective receptor antagonists. Chemical entities of formula I, and pharmaceutically acceptable compositions thereof, are useful for treating a variety of diseases and disorders associated with NR2B receptor antagonism. Such diseases and disorders include those described herein.

DETAILED DESCRIPTION OF CERTAIN EMBODIMENTS

General Description of Chemical Entities

Figure 1:
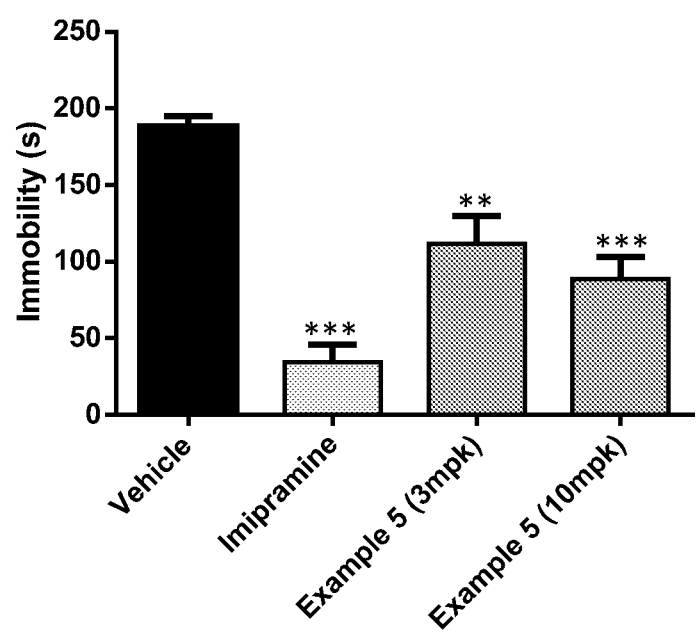
FIG. 1 shows the results of the forced swim test as described in Example 2.4.1.

In some embodiments, the present invention provides chemical entities of formula I:

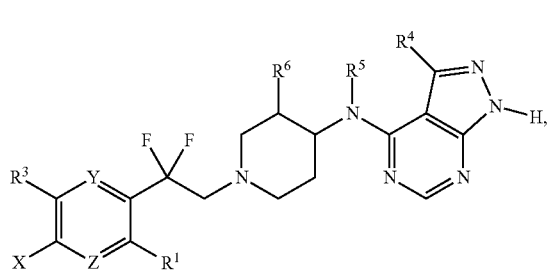

I wherein:
one of Y and Z is N, and the other is $C(R^2)$;
X is hydrogen, halogen, $C_1$-$C_6$ alkyl, $C_3$-$C_6$ cycloalkyl, $C_1$-$C_4$ alkoxy, —$CO_2R^7$, —CN, —$SR^7$, —$S(O)_2R^7$, —$NO_2$, or —$N(R^7)(R^8)$, wherein said $C_1$-$C_6$ alkyl is optionally substituted with one to six fluorine atoms and said $C_1$-$C_4$ alkoxy is optionally substituted with one to six fluorine atoms;
$R^1$ is hydrogen, halogen, $C_1$-$C_4$ alkyl, $C_1$-$C_4$ alkoxy, —CN, —$NO_2$, —$N(R^7)(R^8)$, —$CO_2R^7$, —$C(O)N(R^7)(R^8)$ or $C_3$-$C_6$ cycloalkyl, wherein said $C_1$-$C_4$ alkyl is optionally substituted with one to three fluorine atoms and said $C_1$-$C_4$ alkoxy is optionally substituted with one to three fluorine atoms;
$R^2$ is hydrogen, halogen, $C_1$-$C_4$ alkyl, cyclopropyl or $C_1$-$C_4$ alkoxy wherein said $C_1$-$C_4$ alkyl is optionally substituted with one to three fluorine atoms and said $C_1$-$C_4$ alkoxy is optionally substituted with one to three fluorine atoms;
$R^3$ is hydrogen, —F, —Cl, —$CH_3$, —$CF_3$ or —$OCH_3$;
$R^4$ is hydrogen, —F, —Cl, $C_1$-$C_3$ alkyl or cyclopropyl, wherein said $C_1$-$C_3$ alkyl is optionally substituted with one to three fluorine atoms;
$R^5$ is hydrogen or —$CH_3$;
$R^6$ is hydrogen, —F or —$CH_3$;
each instance of $R^7$ independently is $C_1$-$C_4$ alkyl; and
each instance of $R^8$ independently is hydrogen or $C_1$-$C_4$ alkyl.

Unless otherwise specified or clear from context, the term "chemical entity" refers to a compound having the indicated structure, whether in its "free" form (e.g., "free compound" or "free base" or "free acid" form, as applicable), or in a salt form, particularly a pharmaceutically acceptable salt form, and furthermore whether in solid state form or otherwise. In some embodiments, a solid state form is an amorphous (i.e., non-crystalline) form; in some embodiments, a solid state form is a crystalline form. In some embodiments, a crystalline form (e.g., a polymorph, pseudohydrate, or hydrate). Similarly, the term encompasses the compound whether provided in solid form or otherwise. Unless otherwise specified, all statements made herein regarding "compounds" apply to the associated chemical entities, as defined.

Chemical Entities and Definitions

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

Chemical entities of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The term "alkyl", as by itself or as part of another substituent, means a substituted or unsubstituted, linear or branched, univalent hydrocarbon chain that is completely saturated or that contains one or more units of unsaturation. Unless otherwise specified, alkyl groups contain 1 to 7 carbon atoms ("$C_1$-$C_7$ alkyl"). In some embodiments, alkyl groups contain 1 to 6 carbon atoms ("$C_1$-$C_6$ alkyl"). In some embodiments, alkyl groups contain 1 to 5 carbon atoms ("$C_1$-$C_5$ alkyl"). In some embodiments, alkyl groups contain 1 to 4 carbon atoms ("$C_1$-$C_4$ alkyl"). In some embodiments, alkyl groups contain 3 to 7 carbon atoms ("$C_3$-$C_7$ alkyl"). Examples of saturated alkyl groups include methyl, ethyl, n-propyl, i-propyl, n-butyl, t-butyl, i-butyl, s-butyl, homologs and isomers of, for example, n-pentyl, n-hexyl, n-heptyl, n-octyl, and the like. An unsaturated alkyl group is one having one or more carbon-carbon double bonds or carbon-carbon triple bonds. Examples of unsaturated alkyl groups include allyl, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the like. The term "lower alkyl" refers to alkyl groups having 1 to 4 (if saturated) or 2 to 4 (if unsaturated) carbon atoms. Exemplary lower alkyl groups include methyl, ethyl, n-propyl, i-propyl, n-butyl, s-butyl, i-butyl, t-butyl and the like. The term "alkenyl" refers to alkyl groups having at least two carbon atoms and at least one carbon-carbon double bond. The term "alkynyl" refers to alkyl groups having at least two carbon atoms and at least one carbon-carbon triple bond.

The term "cycloalkyl", by itself or as part of another substituent, refers to a monocyclic univalent hydrocarbon that is completely saturated or that contains one or more units of unsaturation, but which is not aromatic, that has a single point of attachment to the rest of the molecule. In some embodiments, cycloalkyl groups contain 3 to 8 ring carbon atoms ("$C_3$-$C_8$ cycloalkyl"). Examples of cycloalkyl include cyclopropyl, cyclobutyl, cyclopentyl, cyclohexyl, 1-cyclohexenyl, 3-cyclohexenyl, cycloheptyl, and the like.

The term "alkoxy", by itself or as part of another substituent, refers to the group —O-alkyl.

The term "halogen" or "halo", by itself or as part of another substituent, refers to fluorine, chlorine, bromine or iodine.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66:1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement hydrogen, carbon, nitrogen, oxygen, chlorine or fluorine with $^2$H, $^3$H, $^{11}$C, $^{13}$C, $^{14}$C, $^{13}$N, $^{15}$N, $^{17}$O, $^{18}$O, $^{36}$Cl or $^{18}$F, respectively, are within the scope of this invention. Such compounds are useful, for example, as analytical tools, as probes in biological assays, or as therapeutic agents in accordance with the present invention. Additionally, incorporation of heavier isotopes such as deuterium ($^2$H) can afford certain therapeutic advantages resulting from greater metabolic stability, for example, increase in vivo half-life, or reduced dosage requirements.

Exemplary Embodiments of Chemical Entities

In some embodiments, the present invention provides chemical entities of formula I:

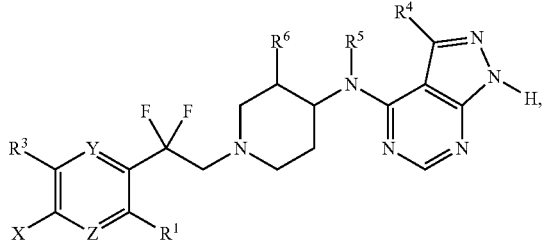

(I)

one of Y and Z is N, and the other is C(R$^2$);
wherein:
X is hydrogen, halogen, C$_1$-C$_6$ alkyl, C$_3$-C$_6$ cycloalkyl, C$_1$-C$_4$ alkoxy, —CO$_2$R$^7$, —CN, —SR$^7$, —S(O)$_2$R$^7$, —NO$_2$, or —N(R$^7$)(R$^8$), wherein said C$_1$-C$_6$ alkyl is optionally substituted with one to six fluorine atoms and said C$_1$-C$_4$ alkoxy is optionally substituted with one to six fluorine atoms;
R$^1$ is hydrogen, halogen, C$_1$-C$_4$ alkyl, C$_1$-C$_4$ alkoxy, —CN, —NO$_2$, —N(R$^7$)(R$^8$), —CO$_2$R$^7$, —C(O)N(R$^7$)(R$^8$) or C$_3$-C$_6$ cycloalkyl, wherein said C$_1$-C$_4$ alkyl is optionally substituted with one to three fluorine atoms and said C$_1$-C$_4$ alkoxy is optionally substituted with one to three fluorine atoms;
R$^2$ is hydrogen, halogen, C$_1$-C$_4$ alkyl, cyclopropyl or C$_1$-C$_4$ alkoxy wherein said C$_1$-C$_4$ alkyl is optionally substituted with one to three fluorine atoms and said C$_1$-C$_4$ alkoxy is optionally substituted with one to three fluorine atoms;
R$^3$ is hydrogen, —F, —Cl, —CH$_3$, —CF$_3$ or —OCH$_3$;
R$^4$ is hydrogen, —F, —Cl, C$_1$-C$_3$ alkyl or cyclopropyl, wherein said C$_1$-C$_3$ alkyl is optionally substituted with one to three fluorine atoms;
R$^5$ is hydrogen or —CH$_3$;
R$^6$ is hydrogen, —F or —CH$_3$;
each instance of R$^7$ independently is C$_1$-C$_4$ alkyl; and
each instance of R$^8$ independently is hydrogen or C$_1$-C$_4$ alkyl.

In some embodiments X is hydrogen.
In some embodiments X is —CN.
In some embodiments X is —SCH$_3$, —SCH$_2$CH$_3$, —SO$_2$CH$_2$CH$_3$, —SO$_2$CH$_3$ or —SO$_2$CF$_3$.
In some embodiments X is —NO$_2$.
In some embodiments X is —N(R$^7$)(R$^8$).
In some embodiments X is —N(CH$_3$)$_2$, —NH(CH$_3$) or —N(CH$_3$)(CH$_2$CH$_3$).
In some embodiments X is fluorine or chlorine.
In some embodiments X is C$_1$-C$_4$ alkyl.
In some embodiments X is —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$ or —CH$_2$CF$_2$CF$_3$.
In some embodiments X is C$_1$-C$_4$ alkoxy.
In some embodiments X is —OCH$_3$, —OCF$_3$, —OCHF$_2$ or OCFH$_2$.
In some embodiments X is C$_3$-C$_6$ cycloalkyl.

In some embodiments X is cyclopropyl.
In some embodiments R$^1$ is hydrogen.
In some embodiments R$^1$ is fluorine or chlorine.
In some embodiments R$^1$ is C$_1$-C$_4$ alkyl.
In some embodiments R$^1$ is —CH$_3$, —CH$_2$CH$_3$, —CH(CH$_3$)$_2$ or —CF$_3$.
In some embodiments R$^1$ is C$_1$-C$_4$ alkoxy.
In some embodiments R$^1$ is —OCH$_3$, —OCF$_3$, —OCHF$_2$ or —OCFH$_2$.
In some embodiments R$^1$ is —CN or —NO$_2$.
In some embodiments R$^1$ is CO$_2$R$^7$.
In some embodiments R$^1$ is —CO$_2$CH$_3$ or —CO$_2$CH$_2$CH$_3$.
In some embodiments R$^1$ is —C(O)N(R$^7$)(R$^8$).
In some embodiments R$^1$ is —C(O)N(CH$_3$)$_2$, —C(O)NH(CH$_3$) or —C(O)N(CH$_3$)(CH$_2$CH$_3$).
In some embodiments R$^1$ is C$_3$-C$_6$ cycloalkyl.
In some embodiments R$^1$ is cyclopropyl.
In some embodiments R$^2$ is hydrogen.
In some embodiments R$^2$ is fluorine or chlorine.
In some embodiments R$^2$ is C$_1$-C$_4$ alkyl.
In some embodiments R$^2$ is —CH$_3$, —CH$_2$CH$_3$, —CH(CH$_3$)$_2$ or —CF$_3$.
In some embodiments R$^2$ is cyclopropyl.
In some embodiments R$^2$ is C$_1$-C$_4$ alkoxy.
In some embodiments R$^2$ is —OCH$_3$, —OCF$_3$, —OCHF$_2$ or —OCFH$_2$.
In some embodiments R$^3$ is hydrogen.
In some embodiments R$^3$ is fluorine or chlorine.
In some embodiments R$^3$ is —CH$_3$, —CF$_3$ or —OCH$_3$.
In some embodiments R$^4$ is hydrogen.
In some embodiments R$^4$ is fluorine or chlorine.
In some embodiments R$^4$ is —CH$_3$.
In some embodiments R$^4$ is cyclopropyl.
In some embodiments R$^5$ is hydrogen.
In some embodiments R$^5$ is —CH$_3$.
In some embodiments R$^6$ is hydrogen.
In some embodiments R$^6$ is —CH$_3$.
In some embodiments R$^6$ is fluorine.

In some embodiments, a chemical entity of formula (I) is a chemical entity of formula (II):

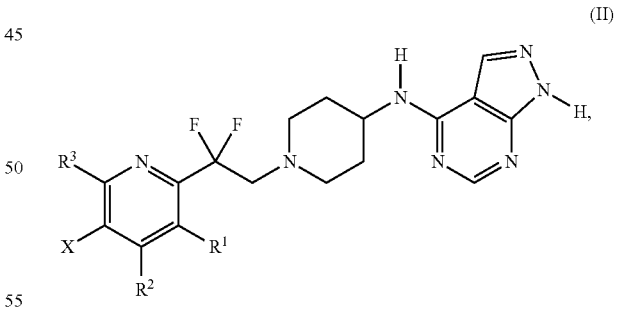

(II)

wherein each of R$^1$, R$^2$, X and R$^3$ is as described in embodiments of formula (I), supra, or described in embodiments herein, both singly and in combination.

In some embodiments of formula (II),
X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl;
R$^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl;

R$^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and R$^3$ is hydrogen —F, —Cl, —CH$_3$, —CF$_3$ or —OCH$_3$.

In some embodiments, a chemical entity of formula (I) is a chemical entity of formula (IIa):

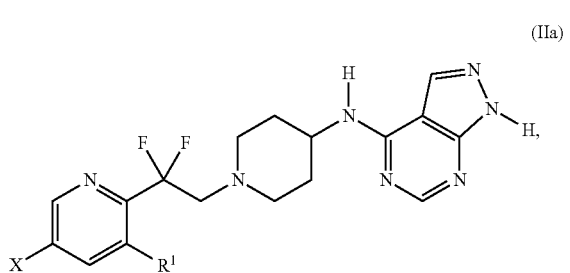

(IIa)

wherein each of R$^1$ and X is as described in embodiments of formula (I), supra, or described in embodiments herein, both singly and in combination.

In some embodiments of formula (IIa),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and R$^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl.

In some embodiments, a chemical entity of formula (I) is a chemical entity of formula (III):

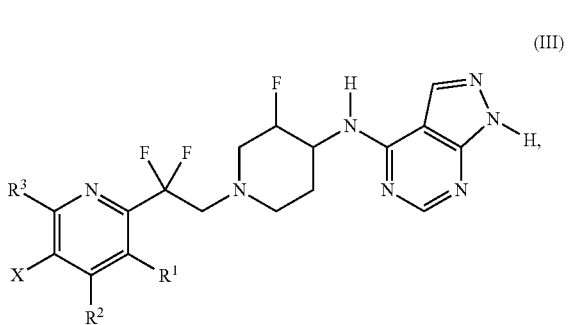

(III)

wherein each of R$^1$, R$^2$, X and R$^3$ is as described in embodiments of formula (I), supra, or described in embodiments herein, both singly and in combination.

In some embodiments of formula (III),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl;

R$^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl; R$^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and R$^3$ is hydrogen —F, —Cl, —CH$_3$, —CF$_3$ or —OCH$_3$.

In some embodiments, a chemical entity of formula (I) is a chemical entity of formula (IIIa):

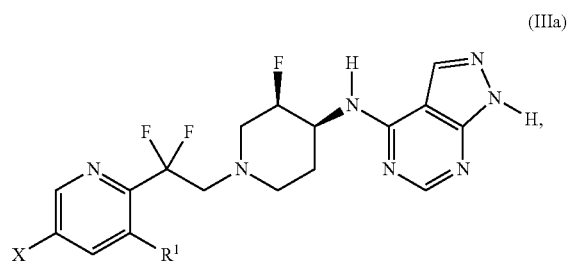

(IIIa)

wherein each of R$^1$ and X is as described in embodiments for formula (I), supra, or described in embodiments herein, both singly and in combination.

In some embodiments of formula (IIIa),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and R$^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl.

In some embodiments, a chemical entity of formula (I) is a chemical entity of formula (IIIb):

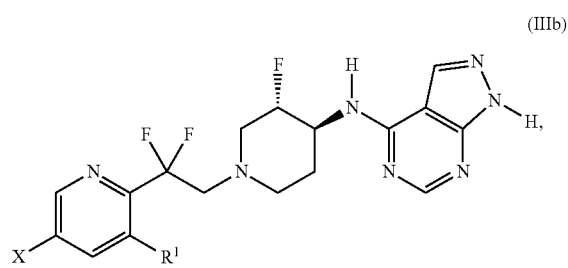

(IIIb)

wherein each of R$^1$ and X is as described in embodiments for formula (I), supra, or described in embodiments herein, both singly and in combination.

In some embodiments of formula (IIIb),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and R$^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl.

In some embodiments, a chemical entity of formula (I) is a chemical entity of formula (IV):

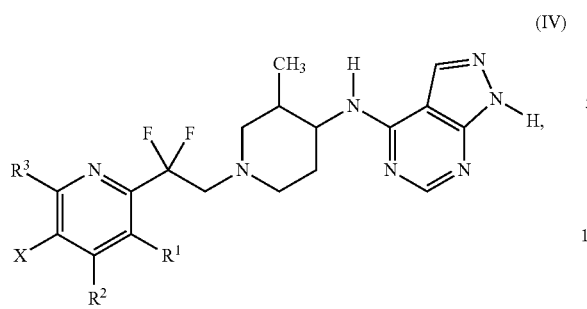

(IV)

wherein each of $R^1$, $R^2$, X and $R^3$ is as described in embodiments of formula (I), supra, or described in embodiments herein, both singly and in combination.

In some embodiments of formula (IV),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl;

$R^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl;

$R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and $R^3$ is hydrogen —F, —Cl, —CH$_3$, —CF$_3$ or —OCH$_3$.

In some embodiments, a chemical entity of formula (I) is a chemical entity of formula (IVa):

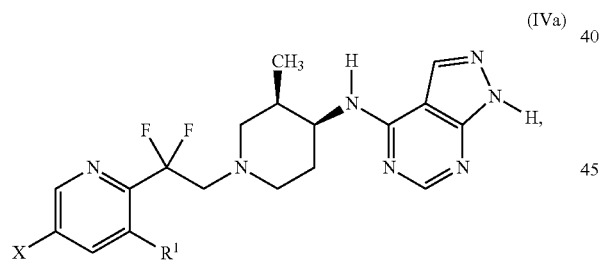

(IVa)

wherein each of $R^1$ and X is as described in embodiments for formula (I), supra, or described in embodiments herein, both singly and in combination.

In some embodiments of formula (IVa),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl.

In some embodiments, a chemical entity of formula (I) is a chemical entity of formula (IVb):

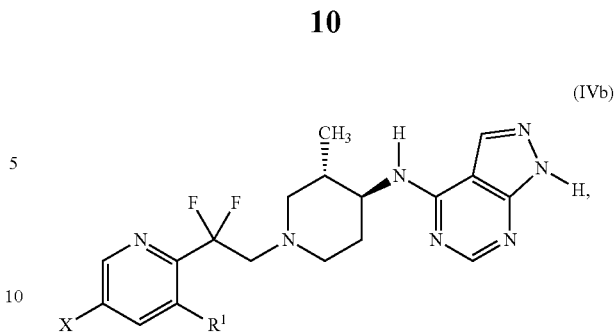

(IVb)

wherein each of $R^1$ and X is as described in embodiments for formula (I), supra, or described in embodiments herein, both singly and in combination.

In some embodiments of formula (IVb),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl.

In some embodiments, a chemical entity of formula (I) is a chemical entity of formula (V):

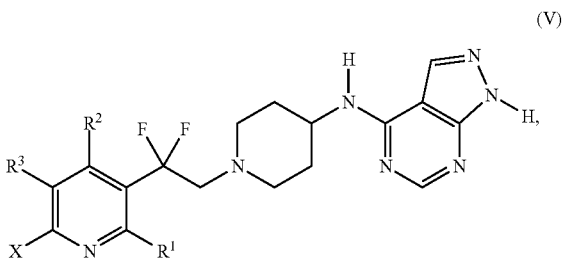

(V)

wherein each of $R^1$, $R^2$, X and $R^3$ is as described in embodiments of formula (I), supra, or described in embodiments herein, both singly and in combination.

In some embodiments of formula (V),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl;

$R^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl;

$R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and $R^3$ is hydrogen —F, —Cl, —CH$_3$, —CF$_3$ or —OCH$_3$.

In some embodiments, a chemical entity of formula (I) is a chemical entity of formula (Va):

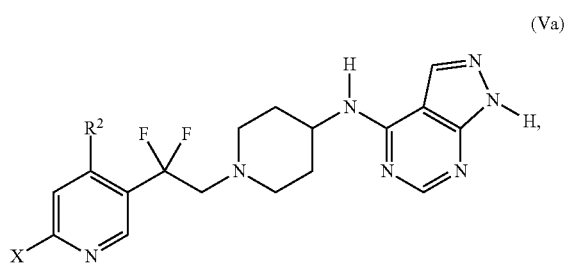

(Va)

wherein each of $R^2$ and X is as described in embodiments of formula (I), supra, or described in embodiments herein, both singly and in combination.

In some embodiments of formula (Va),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$.

In some embodiments, a chemical entity of formula (I) is a chemical entity of formula (VI):

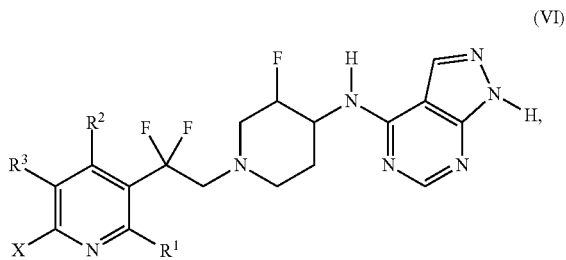

(VI)

wherein each of $R^1$, $R^2$, X and $R^3$ is as described in embodiments of formula (I), supra, or described in embodiments herein, both singly and in combination.

In some embodiments of formula (VI),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl;

$R^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl;

$R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and $R^3$ is hydrogen —F, —Cl, —CH$_3$, —CF$_3$ or —OCH$_3$.

In some embodiments, a chemical entity of formula (I) is a chemical entity of formula (VIa):

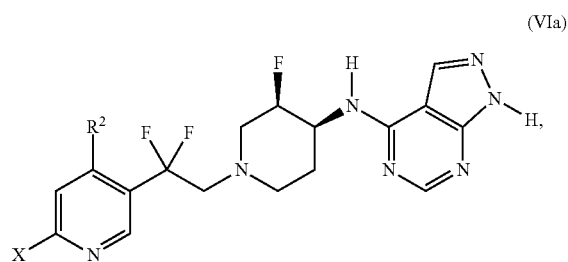

(VIa)

wherein each of $R^2$ and X is as described in embodiments for formula (I), supra, or described in embodiments herein, both singly and in combination.

In some embodiments of formula (VIa),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$.

In some embodiments, a chemical entity of formula (I) is a chemical entity of formula (VIb):

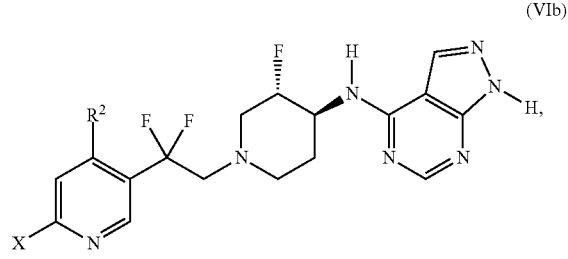

(VIb)

wherein each of $R^2$ and X is as described in embodiments for formula (I), supra, or described in embodiments herein, both singly and in combination.

In some embodiments of formula (VIb),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$.

In some embodiments, a chemical entity of formula (I) is a chemical entity of formula (VII):

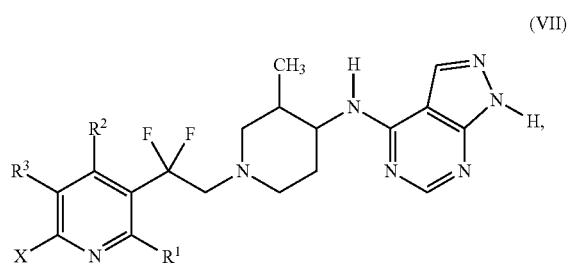

(VII)

wherein each of $R^1$, $R^2$, X and $R^3$ is as described in embodiments of formula (I), supra, or described in embodiments herein, both singly and in combination.

In some embodiments of formula (VII),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl;

$R^1$ is hydrogen, —F, —Cl, —CH$_3$, —CH$_2$CH$_3$, —CH(CH$_3$)$_2$, —CF$_3$, —OCH$_3$, —OCF$_3$, —OCHF$_2$, —OCFH$_2$, —CN, —NO$_2$, —CO$_2$CH$_3$, —CO$_2$CH$_2$CH$_3$, —C(O)N(CH$_3$)$_2$, —C(O)NH(CH$_3$) or cyclopropyl;

$R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$; and $R^3$ is hydrogen —F, —Cl, —CH$_3$, —CF$_3$ or —OCH$_3$.

In some embodiments, a chemical entity of formula (I) is a chemical entity of formula (VIIa):

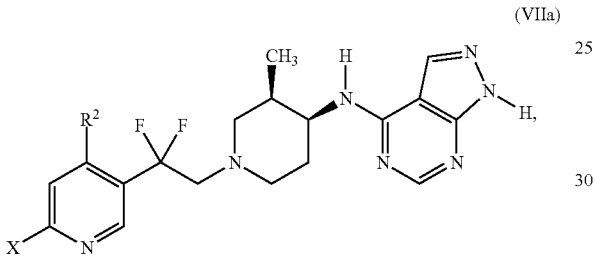

(VIIa)

wherein each of $R^2$ and X is as described in embodiments for formula (I), supra, or described in embodiments herein, both singly and in combination.

In some embodiments of formula (VIIa),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$.

In some embodiments, a chemical entity of formula (I) is a chemical entity of formula (VIIb):

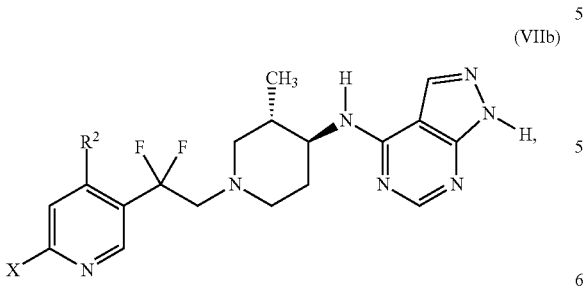

(VIIb)

wherein each of $R^2$ and X is as described in embodiments for formula (I), supra, or described in embodiments herein, both singly and in combination.

In some embodiments of formula (VIIb),

X is hydrogen, —CN, —SCH$_3$, —SO$_2$CH$_3$, —SO$_2$CF$_3$, —NO$_2$, —N(CH$_3$)$_2$, —F, —Cl, —CH$_3$, —CH$_2$CH$_3$, —CH(CH$_3$)$_2$, —CF$_3$, —CHF$_2$, —CH$_2$F, —CF$_2$CF$_3$, —CH(CF$_3$)$_2$, —CH$_2$CF$_2$CF$_3$, —OCH$_3$, —OCF$_3$, —OCHF$_2$, —OCFH$_2$ or cyclopropyl; and $R^2$ is hydrogen, —F, —Cl, —CH$_3$, —CH$_2$CH$_3$, —CH(CH$_3$)$_2$, —CF$_3$, cyclopropyl, —OCH$_3$, —OCF$_3$, —OCHF$_2$ or —OCFH$_2$.

Exemplary chemical entities of formula I are shown in Tables 1.C to 8.C, below.

TABLE 1.C

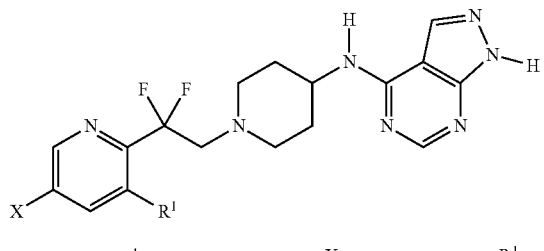

| compound | X | $R^1$ |
|---|---|---|
| C-1 | H | H |
| C-2 | F | H |
| C-3 | Cl | H |
| C-4 | CH$_3$ | H |
| C-5 | CF$_3$ | H |
| C-6 | CF$_2$H | H |
| C-7 | CH$_2$F | H |
| C-8 | CH$_2$CH$_3$ | H |
| C-9 | cyclopropyl | H |
| C-10 | CH$_3$O | H |
| C-11 | CF$_3$O | H |
| C-12 | CHF$_2$O | H |
| C-13 | SCH$_3$ | H |
| C-14 | CN | H |
| C-15 | F | F |
| C-16 | Cl | F |
| C-17 | CH$_3$ | F |
| C-18 | CF$_3$ | F |
| C-19 | CF$_2$H | F |
| C-20 | CH$_2$F | F |
| C-21 | CH$_2$CH$_3$ | F |
| C-22 | cyclopropyl | F |
| C-23 | F | Cl |
| C-24 | Cl | Cl |
| C-25 | CH$_3$ | Cl |
| C-26 | CF$_3$ | Cl |
| C-27 | cyclopropyl | Cl |
| C-28 | F | CH$_3$ |
| C-29 | Cl | CH$_3$ |
| C-30 | CH$_3$ | CH$_3$ |
| C-31 | CF$_3$ | CH$_3$ |
| C-32 | cyclopropyl | CH$_3$ |

TABLE 2.C

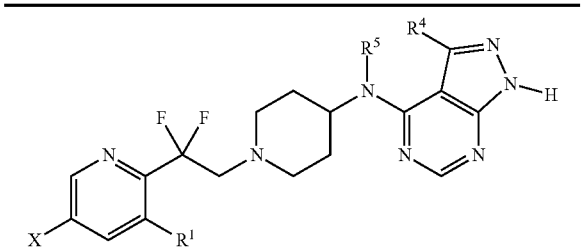

| compound | X | $R^1$ | $R^4$ | $R^5$ |
|---|---|---|---|---|
| C-33 | CF$_3$ | H | CH$_3$ | H |
| C-34 | Cl | H | CH | H |
| C-35 | CH$_3$ | H | CH$_3$ | H |
| C-36 | CF$_3$ | H | Cl | H |
| C-37 | Cl | H | Cl | H |

TABLE 2.C-continued

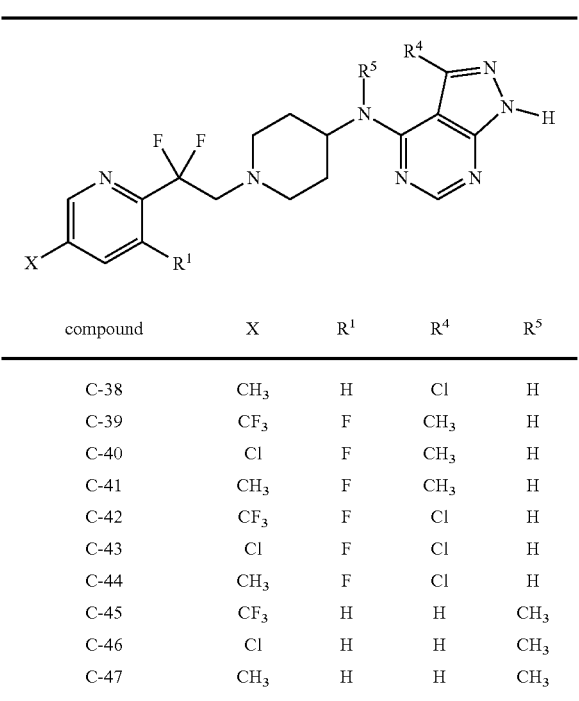

| compound | X | R¹ | R⁴ | R⁵ |
|---|---|---|---|---|
| C-38 | CH₃ | H | Cl | H |
| C-39 | CF₃ | F | CH₃ | H |
| C-40 | Cl | F | CH₃ | H |
| C-41 | CH₃ | F | CH₃ | H |
| C-42 | CF₃ | F | Cl | H |
| C-43 | Cl | F | Cl | H |
| C-44 | CH₃ | F | Cl | H |
| C-45 | CF₃ | H | H | CH₃ |
| C-46 | Cl | H | H | CH₃ |
| C-47 | CH₃ | H | H | CH₃ |

TABLE 3.C

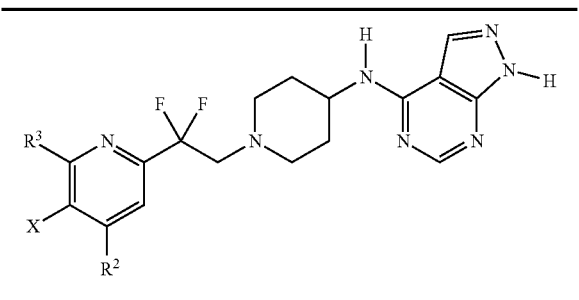

| compound | X | R² | R³ |
|---|---|---|---|
| C-48 | F | F | H |
| C-49 | Cl | F | H |
| C-50 | CH₃ | F | H |
| C-51 | CF₃ | F | H |
| C-52 | F | CH₃ | H |
| C-53 | Cl | CH₃ | H |
| C-54 | CH₃ | CH₃ | H |
| C-55 | CF₃ | CH₃ | H |
| C-56 | F | Cl | H |
| C-57 | Cl | Cl | H |
| C-58 | CH₃ | Cl | H |
| C-59 | CF₃ | Cl | F |
| C-60 | F | H | F |
| C-61 | Cl | H | F |
| C-62 | CH₃ | H | F |
| C-63 | CF₃ | H | Cl |
| C-64 | F | H | Cl |
| C-65 | Cl | H | Cl |
| C-66 | CH₃ | H | Cl |
| C-67 | CF₃ | H | CH₃ |
| C-68 | F | H | CH₃ |
| C-69 | Cl | H | CH₃ |
| C-70 | CH₃ | H | CH₃ |

TABLE 4.C

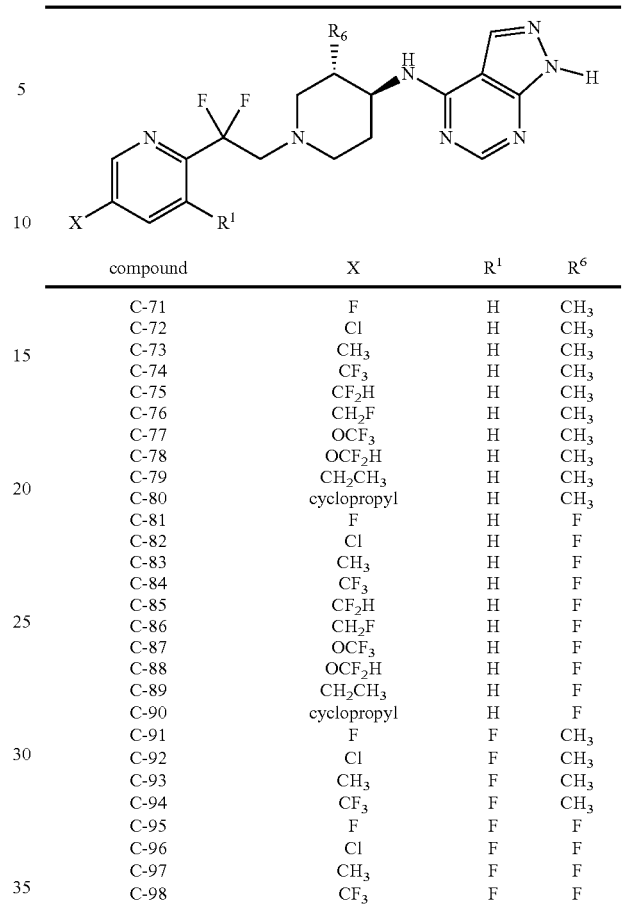

| compound | X | R¹ | R⁶ |
|---|---|---|---|
| C-71 | F | H | CH₃ |
| C-72 | Cl | H | CH₃ |
| C-73 | CH₃ | H | CH₃ |
| C-74 | CF₃ | H | CH₃ |
| C-75 | CF₂H | H | CH₃ |
| C-76 | CH₂F | H | CH₃ |
| C-77 | OCF₃ | H | CH₃ |
| C-78 | OCF₂H | H | CH₃ |
| C-79 | CH₂CH₃ | H | CH₃ |
| C-80 | cyclopropyl | H | CH₃ |
| C-81 | F | H | F |
| C-82 | Cl | H | F |
| C-83 | CH₃ | H | F |
| C-84 | CF₃ | H | F |
| C-85 | CF₂H | H | F |
| C-86 | CH₂F | H | F |
| C-87 | OCF₃ | H | F |
| C-88 | OCF₂H | H | F |
| C-89 | CH₂CH₃ | H | F |
| C-90 | cyclopropyl | H | F |
| C-91 | F | F | CH₃ |
| C-92 | Cl | F | CH₃ |
| C-93 | CH₃ | F | CH₃ |
| C-94 | CF₃ | F | CH₃ |
| C-95 | F | F | F |
| C-96 | Cl | F | F |
| C-97 | CH₃ | F | F |
| C-98 | CF₃ | F | F |

TABLE 5.C

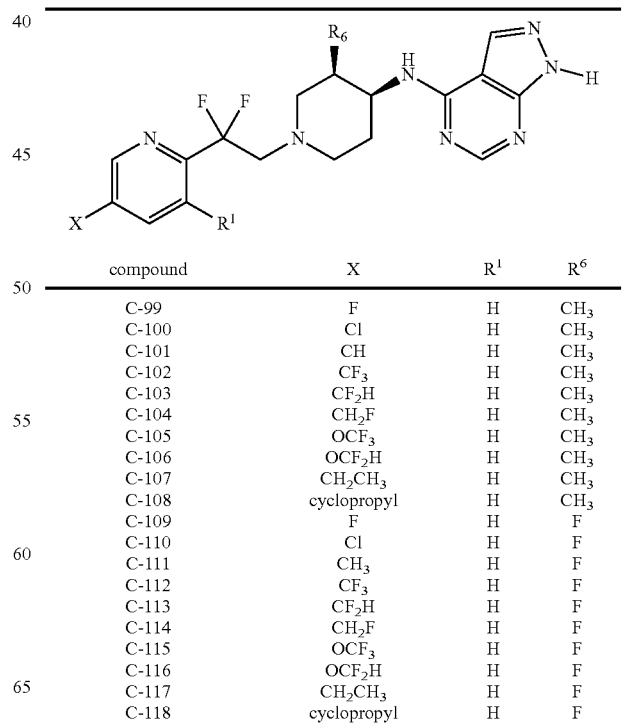

| compound | X | R¹ | R⁶ |
|---|---|---|---|
| C-99 | F | H | CH₃ |
| C-100 | Cl | H | CH₃ |
| C-101 | CH | H | CH₃ |
| C-102 | CF₃ | H | CH₃ |
| C-103 | CF₂H | H | CH₃ |
| C-104 | CH₂F | H | CH₃ |
| C-105 | OCF₃ | H | CH₃ |
| C-106 | OCF₂H | H | CH₃ |
| C-107 | CH₂CH₃ | H | CH₃ |
| C-108 | cyclopropyl | H | CH₃ |
| C-109 | F | H | F |
| C-110 | Cl | H | F |
| C-111 | CH₃ | H | F |
| C-112 | CF₃ | H | F |
| C-113 | CF₂H | H | F |
| C-114 | CH₂F | H | F |
| C-115 | OCF₃ | H | F |
| C-116 | OCF₂H | H | F |
| C-117 | CH₂CH₃ | H | F |
| C-118 | cyclopropyl | H | F |

TABLE 5.C-continued

| compound | X | R¹ | R⁶ |
|---|---|---|---|
| C-119 | F | F | CH₃ |
| C-120 | Cl | F | CH₃ |
| C-121 | CH₃ | F | CH₃ |
| C-122 | CF₃ | F | CH₃ |
| C-123 | F | F | F |
| C-124 | Cl | F | F |
| C-125 | CH₃ | F | F |
| C-126 | CF₃ | F | F |

TABLE 6.C

| compound | X | R¹ | R² | R³ |
|---|---|---|---|---|
| C-127 | CF₃ | H | H | H |
| C-128 | CH₃ | H | H | H |
| C-129 | F | H | H | H |
| C-130 | Cl | H | H | H |
| C-131 | OCH₃ | H | H | H |
| C-132 | OCF₃ | H | H | H |
| C-133 | SCH₃ | H | H | H |
| C-134 | CH₂CH₃ | H | H | H |
| C-135 | cyclopropyl | H | H | H |
| C-136 | CF₃ | F | H | H |
| C-137 | CF₃ | H | F | H |
| C-138 | CF₃ | H | H | F |
| C-139 | H | CF₃ | H | H |
| C-140 | H | H | CF₃ | H |
| C-141 | H | H | H | CF₃ |

TABLE 7.C

| compound | X | R⁴ | R⁶ |
|---|---|---|---|
| C-142 | CF₃ | CH₃ | H |
| C-143 | CH₃ | CH₃ | H |
| C-144 | CF₃ | H | F |
| C-145 | CH₃ | H | F |
| C-146 | CH₂CH₃ | H | F |
| C-147 | SCH₃ | H | F |

TABLE 7.C-continued

| compound | X | R⁴ | R⁶ |
|---|---|---|---|
| C-148 | cyclopropyl | H | F |
| C-149 | OCF₃ | H | F |
| C-150 | OCH₃ | H | F |
| C-151 | CF₃ | H | CH₃ |
| C-152 | CH₃ | H | CH₃ |
| C-153 | CH₂CH₃ | H | CH₃ |
| C-154 | SCH₃ | H | CH₃ |
| C-155 | cyclopropyl | H | CH₃ |
| C-156 | OCF₃ | H | CH₃ |
| C-157 | OCH₃ | H | CH₃ |

TABLE 8.C

| compound | X | R⁴ | R⁶ |
|---|---|---|---|
| C-158 | CF₃ | Cl | H |
| C-159 | CH₃ | Cl | H |
| C-160 | CF₃ | H | F |
| C-161 | CH₃ | H | F |
| C-162 | CH₂CH₃ | H | F |
| C-163 | SCH₃ | H | F |
| C-164 | cyclopropyl | H | F |
| C-165 | OCF₃ | H | F |
| C-166 | OCH₃ | H | F |
| C-167 | CF₃ | H | CH₃ |
| C-168 | CH₃ | H | CH₃ |
| C-169 | CH₂CH₃ | H | CH₃ |
| C-170 | SCH₃ | H | CH₃ |
| C-171 | cyclopropyl | H | CH₃ |
| C-172 | OCF₃ | H | CH₃ |
| C-173 | OCH₃ | H | CH₃ |

Pharmacology

Glutamate (GLU) is a fundamental excitatory neurotransmitter in the mammalian brain and central nervous system (CNS). The effects of this endogenous neurotransmitter are mediated through binding to and activation of GLU to glutamate receptors (GLURs), which are broadly classified into metabotropic G-protein coupled (mGluRs) and ligand gated ion channels or ionotropic GluRs. The ionotropic GLURs are pharmacologically classified into three main types based on the actions of selective receptor agonists: NMDA (N-methyl D-aspartate selective), KA (kainic acid selective) and AMPA (α-amino-3-hydroxy-5-methyl-4-isoxazolepropionic acid) receptors whose structure and pharmacological function has been recently reviewed in detail (S. F. Traynelis et al. *Pharmacology Reviews*, 2010, 62, 405-496). Electrophysiology studies have demonstrated NMDARs to be cation ion channels that are subject to voltage-dependent channel block by endogenous $Mg^{2+}$. Activation of NMDARs by glutamate in the presence of glycine as a co-agonist results in opening of the receptor ion channel. This in turn allows for the flow of $Na^+$ and $Ca^{2+}$ into the cell generating excitatory postsynaptic potentials (EPSPs) and $Ca^{2+}$ activated second messenger signaling pathways in neurons. By virtue of their permeability to $Ca^{2+}$, activation of NMDA receptors regulates long-term changes in neuronal communication such as learning and memory and synaptic plasticity.

Since the original pharmacological characterization with selective ligands, molecular biology and cloning studies have enabled detailed characterization of NMDARs at the molecular level (Paoletti et al., 2013, Nat. Rev. Neurosci. 14:383-400). Thus, NMDARs are heterotetramers comprised of two NR1 subunits and two NR2 subunits. NR1 subunits contain the binding site for the glycine co-agonist while NR2 subunits contain the binding site for glutamate. The existence of multiple splice variants for NR1 and four isoforms of NR2 (NR2A, NR2B, NR2C and NR2D) from different genes results in a diverse molecular array and of NMDARs. The pharmacological and electrophysiological properties of NMDARs vary depending on the particular NR1 isoform and NR2 subtype composition. Furthermore, the NR2 subtype isoforms are differentially expressed across cell types and brain regions. Thus, compounds that interact selectivity with NR2 subunits can exert specific pharmacological effects in particular brain regions and have potential to treat CNS diseases with a high degree of specificity and selectivity (e.g. vz side effects). For example the low expression of the NR2B subtype in the cerebellum relative to other brain structures (Cull-Candy et al., 1998, Neuropharmacol. 37:1369-1380) indicated lower motor side effects for this subtype.

NMDA receptor antagonism has been extensively investigated for its potential to treat a variety of CNS diseases including stroke, epilepsy, pain, depression Parkinson's Disease and Alzheimer's disease (Paoletti et al., Nat. Rev. Neurosci 14:383-400; Sancora, 2008, Nature Rev. Drug Disc., 7, 426-437). The NMDA receptor offers a number of pharmacological entry points for developing receptor inhibitors. Direct blockers of the NMDAR ion channel pore represent one family of antagonist compounds for which efficacy could be demonstrated in diverse in vitro and in vivo CNS disease models including, epilepsy, pain and neurodegeneration/stroke. However, compounds from this class, as exemplified by phencyclidine (PCP), MK-801, and ketamine, are generally categorized as unselective across the diversity of NMDA receptor subtypes.

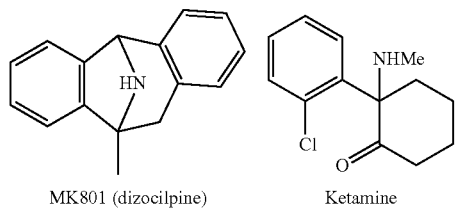

MK801 (dizocilpine)   Ketamine

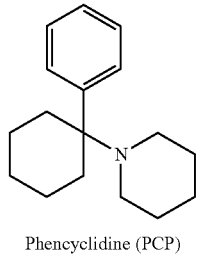

Phencyclidine (PCP)

In humans unselective, high-affinity NMDAR antagonists have generally been associated with serious clinical side effects including hallucinations, dysphoria and lack of coordination. Nevertheless, ketamine, an intravenous drug originally approved for use in anesthesia (Haas et. al, 1992, Anesthesia Prog., 39, 61-68) has more recently demonstrated clinical efficacy as an antidepressant therapy (Katalinic et al. 2013, Aust. N. Z. J. Psychiatry, 47, 710-727). The antidepressant action of acute ketamine therapy has an essentially immediate onset compared to approximately six weeks required for standard serotonin reuptake inhibitor (SSRI) drug therapy. Thus, intravenous administration of the drug has shown rapid onset and prolonged efficacy that can be maintained with continued intermittent administrations (Zarate et al., 2006, Arch. Gen. Psychiatry 63, 856-864). Finally, ketamine has been shown to be effective in cases of depression resistant to standard drug therapies (Murrough et al., 2013, American J. Psychiatry, 170, 1134-1142) including bipolar depression (Zarate et al. 2012, Biol. Psychiatry, 71, 939-946). However, as an intravenous drug with serious side effects (Gianni et. al 1985, Psychiatric Medicine, 3, 197-217; Curran et al 2000, Addiction, 95, 575-590) and potential chronic toxicity (Hardy et al., 2012, J. Clin. Oncol. 30:3611-3617; Noppers et al., 2011, Pain 152:2173-2178) ketamine therapy is of limited utility and restricted to acute or intermittent administration. To have broader scope of application and utility as a therapy for depression and other CNS diseases, orally active selective NMDA antagonists with reduced side effects are needed that can be administered chronically.

Ifenprodil, a vasodilator $\alpha_1$-adrenergic antagonist drug, was determined to have a novel allosteric modulator mechanism of action at the NR2B NMDA receptor subtype (Reynolds et al. 1989, Mol. Pharmacol., 36, 758-765). This new mechanism held promise for a new class of NMDA antagonist drugs having therapeutic efficacy without the limiting side effects of subtype unselective ion channel blockers. Following this discovery, NR2B selective antagonist analogs of ifenprodil (Borza et al., 2006, Current Topics in Medicinal Chemistry, 6, 687-695; Layton et al. Current Topics in Medicinal Chemistry, 6, 697-709) optimized against the undesirable $\alpha_1$-adrenergic activity included Ro-25,6981 (Fischer et al. 1997, J. Pharmacol. Exp. Ther., 283, 1285-1292) and CP-101,606 otherwise known as traxoprodil (Chenard et al. 1995, Journal of Medicinal Chemistry, 38, 3138-3145; Menniti et al. 1998, CNS Drug Reviews., 4, 307-322). In a clinical study, CP-101,606 evidenced antidepressant activity in humans after intravenous administration with a favorable dissociative side effect profile relative to unselective NMDA antagonists (Preskorn et al. 2008, *Journal of Clinical Psychopharmacology*, 28, 631-637). However, CP-101,606 has suboptimal pharmacokinetic properties and requires limiting intravenous administration. For CP-101,606 a slow intravenous infusion protocol was required for optimal results in the aforementioned antidepressant clinical study (Preskorn et al. 2008, *Journal of Clinical Psychopharmacology*, 28, 631-637).

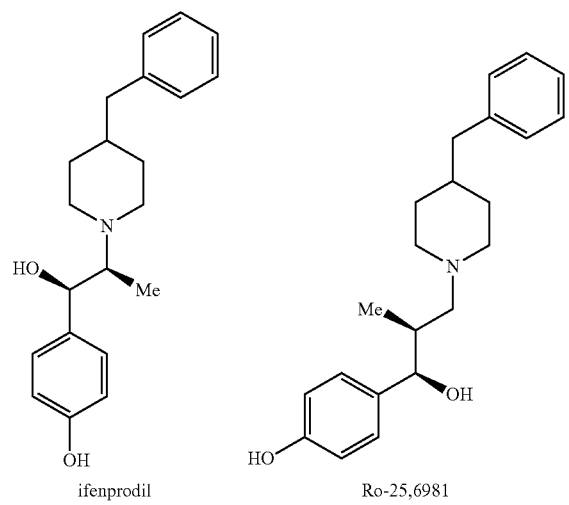

ifenprodil

Ro-25,6981

CP-101,606

Other NR2B antagonists which have been described as reviewed by B. Ruppa et al. (K. B. Ruppa et al., *Annual Reports in Medicinal Chemistry* 2012, 47:89-103) include MK0657 (J. A. McCauley et al., 3$^{rd}$ *Anglo-Swedish Medicinal Chemistry Symposium*, Å re, Sweden, Mar. 11-14, 2007; L. Mony et al., *British J. of Pharmacology* 2009, 157:1301-1317; see also Intl. Appl. Publ. No. WO 2004/108705; U.S. Pat. No. 7,592,360) and compounds of formula LX (Intl. Appl. Publ. No. WO 2006/113471), below, including the specific analog LX-1 depicted below.

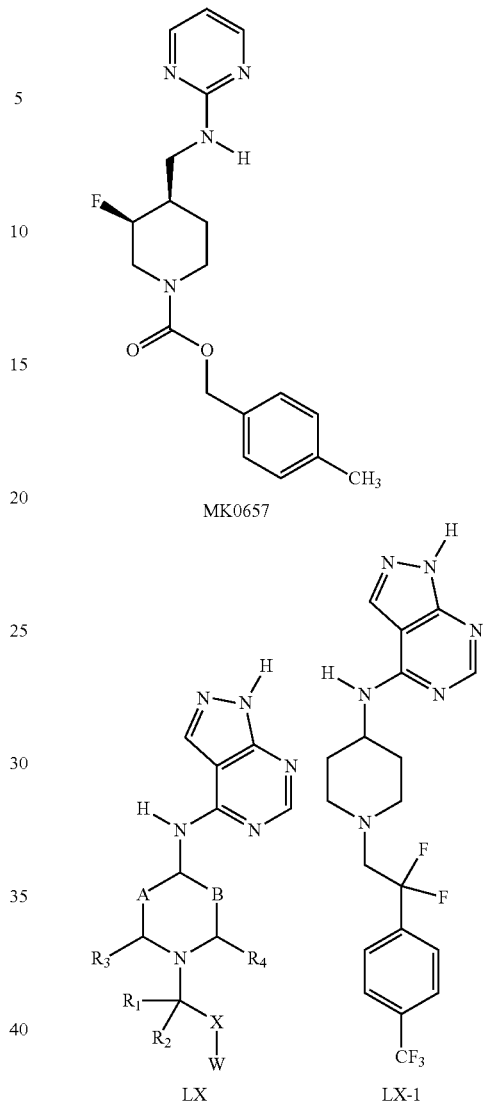

MK0657

LX

LX-1

The difficulties presented by NR2B antagonists having basic amine moieties with regard to overcoming hERG and CYP2D6 safety liabilities while maintaining NR2B in vitro and in vivo potency are well established as noted by Kawai et al. (M. Kawai et al., *Bioorganic and Medicinal Chem. Lett.* 2007, v17:5533-5536) and Brown et al. (Brown et al., *Bioorganic and Medicinal Chem. Lett.* 2011, v21:3399-3403). Compound inhibition of hERG channels and associated QT prolongation in the electrocardiograph (ECG) represents a well recognized serious human cardiovascular safety risk (Hancox et al., *Molecular Pharmacology* 2008, 73:1592-1595). QT prolongation can lead to torsades de pointes (TdP) cardiac arrhythmia which can degenerate into ventricular tachycardia and sudden death.

Compound inhibition of human metabolic cytochrome P-450 enzymes including CYP2D6 represents a risk with regard to human drug safety due to drug-drug interactions (*Drug Metabolism Handbook: Concepts and Applications*, ed. Ala F. Nassar copyright 2009 Wiley & Sons, Hoboken, N.J.). Thus, the clearance of drugs that are substrates of CYP2D6 can be reduced by compounds that inhibit CYP2D6. The result can be toxic or side effect overload due to accumulation of the given CYP2D6 drug substrate. CNS drugs including antidepressant drugs feature prominently among the established CYP2D6 substrates. Therefore, CYP2D6 inhibition is highly undesirable for an NR2B antagonist drug especially given the common application of comedications or polypharmacy in CNS indications including depression. Examples of CY2D6 substrates include antidepressants from the SSRI class such as fluoxetine, paroxetine, and fluvoxamine, duloxetine, an antidepressants from the SSNI class, numerous antipsychotics including haloperidol, risperidone and aripiperazole, numerous beta-blocker antihypertensives including metaprolol, propranolol, timolol and alprenolol and the Alzheimer's disease anticholinesterase inhibitor drug donepezil (Flockhart DA (2007). "Drug Interactions: Cytochrome P450 Drug Interaction Table", Indiana University School of Medicine, accessed at <<http://medicine.iupui.edu/clinpharm/ddis/>> on May 28, 2014).

MK0657 and closely related analogs (Liverton et al., *J. Med. Chem.* 2007, v50:807-819) represent an improved generation of NR2B antagonists with respect to human oral bioavailability. However, drug-related systolic as well as diastolic blood pressure elevation cardiovascular side effect for MK0657 after oral dosing have been described in a published clinical efficacy trial study in patients with Parkinson's Disease (Addy et al., *J. Clin. Pharm.* 2009, v49: 856-864). Similar blood pressure effects were reported to have also been observed after single doses of MK0657 in safety studies with healthy elderly subjects. Compound LX-1 demonstrates oral bioavailability in animals and lacks a phenolic group which can compromise oral bioavailability in humans. However, as noted herein, compound LX-1, which has a basic piperidine nitrogen atom, exhibits human hERG channel inhibition with an $IC_{50}$<10 µM (~4.5 µM), and exhibits human CYP2D6 metabolic enzyme inhibition activity ($IC_{50}$~1.0 µM).

For broad scope of application and safe human use, improved NR2B selective antagonists are needed, as noted in a recent review (K. B. Ruppa et al., *Annual Reports in Medicinal Chemistry* 2012, 47:89-103). There is a need for NR2B antagonist compounds which are improved in one or more aspects exemplified by pharmacokinetic, absorption, metabolism, excretion (ADME, e.g., oral activity), improved efficacy, off-target activity, improved therapeutic safety index relative and compatibility with chronic oral therapy.

Provided chemical entities are antagonists of the NR2B receptor and have technical advantages with regard to one or more pharmaceutical drug properties, such as oral bioavailability, pharmacokinetic parameters, ADME properties (e.g., CYP inhibition), cardiac ion channel (e.g., hERG) activity and other non-NMDA off-target side effect mediating receptors. In some embodiments, the present invention encompasses the discovery that a provided chemical entity can exhibit low human CYP2D6 inhibition and/or low hERG inhibition while exhibiting potent human NR2B receptor inhibition antagonism, and as such is favorable for application in humans.

In some embodiments, a provided chemical entity has NR2B functional NMDA receptor selectivity versus NR2A ("NR2B selectivity", determined as the ratio NR2A $IC_{50}$/NR2B $IC_{50}$, in which the $IC_{50}$ values are measured according to the procedure of Example 2.1)≥300. In some embodiments, a provided chemical entity has NR2B selectivity ≥250. In some embodiments, a provided chemical entity has NR2B selectivity ≥200. In some embodiments, a provided chemical entity has NR2B selectivity ≥150. In some embodiments, a provided chemical entity has NR2B selectivity ≥100. In some embodiments, a provided chemical entity has NR2B selectivity ≥50.

In some embodiments, a provided chemical entity has hERG activity (determined as hERG $IC_{50}$ measured according to the procedure of Example 2.2)≥5 µM. In some embodiments, a provided chemical entity has hERG $IC_{50}$≥10 µM. In some embodiments, a provided chemical entity has hERG $IC_{50}$≥15 µM. In some embodiments, a provided chemical entity has hERG $IC_{50}$≥20 µM. In some embodiments, a provided chemical entity has hERG $IC_{50}$≥25 µM. In some embodiments, a provided chemical entity has hERG $IC_{50}$≥30 µM.

In some embodiments, a provided chemical entity has NR2B functional antagonist activity (determined as NR2B $IC_{50}$ measured according to the procedure of Example 2.1) ≤100 nM and hERG activity (determined as hERG $IC_{50}$ measured according to the procedure of Example 2.2)≥5 µM. In some embodiments, a provided chemical entity has NR2B $IC_{50}$≤100 nM and hERG $IC_{50}$≥10 µM. In some embodiments, a provided chemical entity has NR2B $IC_{50}$≤100 nM and hERG $IC_{50}$≥15 µM. In some embodiments, a provided chemical entity has NR2B $IC_{50}$≤100 nM and hERG $IC_{50}$≥20 µM. In some embodiments, a provided chemical entity has NR2B $IC_{50}$≤100 nM and hERG $IC_{50}$≥25 µM. In some embodiments, a provided chemical entity has NR2B $IC_{50}$≤100 nM and hERG $IC_{50}$≥30 µM. In some embodiments, a provided chemical entity has NR2B $IC_{50}$≤50 nM and hERG $IC_{50}$≥5 µM. In some embodiments, a provided chemical entity has NR2B $IC_{50}$≤50 nM and hERG $IC_{50}$≥10 µM. In some embodiments, a provided chemical entity has NR2B $IC_{50}$≤50 nM and hERG $IC_{50}$≥15 µM. In some embodiments, a provided chemical entity has NR2B $IC_{50}$≤50 nM and hERG $IC_{50}$≥20 µM. In some embodiments, a provided chemical entity has NR2B $IC_{50}$≤50 nM and hERG $IC_{50}$≥25 µM. In some embodiments, a provided chemical entity has NR2B $IC_{50}$≤50 nM and hERG $IC_{50}$≥30 µM.

In some embodiments, a provided chemical entity has NR2B functional antagonist activity (determined as NR2B $IC_{50}$ measured according to the procedure of Example 2.1) ≤100 nM and CYP2D6 inhibition (measured as CYP2D6 $IC_{50}$ determined according to the procedure of Example 2.3)≥2 µM. In some embodiments, a provided chemical entity has NR2B $IC_{50}$≤100 nM and CYP2D6 $IC_{50}$≥3 µM. In some embodiments, a provided chemical entity has NR2B $IC_{50}$≤100 nM and CYP2D6 $IC_{50}$≥4 µM. In some embodiments, a provided chemical entity has NR2B $IC_{50}$≤100 nM and CYP2D6 $IC_{50}$≥5 µM. In some embodiments, a provided chemical entity has NR2B $IC_{50}$≤100 nM and CYP2D6 $IC_{50}$ of about 5-10 µM. In some embodiments, a provided chemical entity has NR2B $IC_{50}$≤100 nM and CYP2D6 $IC_{50}$≥10 µM. In some embodiments, a provided chemical entity has NR2B $IC_{50}$≤50 nM and CYP2D6 $IC_{50}$≥2 µM. In some embodiments, a provided chemical entity has NR2B $IC_{50}$≤50 nM and CYP2D6 $IC_{50}$≥3 µM. In some embodiments, a provided chemical entity has NR2B $IC_{50}$≤50 nM and CYP2D6 $IC_{50}$≥4 µM. In some embodiments, a provided chemical entity has NR2B $IC_{50}$≤50 nM and CYP2D6 $IC_{50}$≥5 µM. In some embodiments, a provided chemical entity has NR2B $IC_{50}$≤50 nM and CYP2D6 $IC_{50}$ of about 5-10 µM. In some embodiments, a provided chemical entity has NR2B $IC_{50}$≤50 nM and CYP2D6 $IC_{50}$≥10 µM.

Uses, Formulation and Administration, and Pharmaceutically Acceptable Compositions In some embodiments, the invention provides a composition comprising a chemical entity of the invention or a pharmaceutically acceptable derivative thereof and a pharmaceutically acceptable carrier, adjuvant, or vehicle. The amount of chemical entity in compositions of this invention is such that is effective to measurably inhibit NR2B, in a biological sample or in a patient. In some embodiments, the amount of chemical entity in compositions of this invention is such that is effective to measurably inhibit NR2B, in a biological sample or in a patient. In some embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the chemical entity with which it is formulated. Pharmaceutically acceptable carriers, adjuvants or vehicles that may be used in the compositions of this invention include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic ester, salt of an ester or other derivative of a chemical entity of this invention (e.g., a prodrug) that, upon administration to a recipient, is capable of providing, either directly or indirectly, a chemical entity of this invention or an inhibitorily active metabolite or residue thereof.

As used herein, the term "inhibitorily active metabolite or residue thereof" means that a metabolite or residue thereof is also an inhibitor of NR2B.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon a variety of factors, including the host treated and the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Chemical Entities and Pharmaceutically Acceptable Compositions

Human therapeutic applications of NR2B receptor antagonists have been summarized in reviews by Traynelis et al. (S. F. Traynelis et al., *Pharmacology Reviews*, 2010, 62:405-496), Beinat et al. (C. Beinat et al., *Current Medicinal Chemistry*, 2010, 17:4166-4190) and Mony et al. (L. Mony et al., *British J. of Pharmacology*, 2009, 157:1301-1317). Antagonism of NR2B can be useful in the treatment of diseases and disorders including depression, pain, Parkinson's disease, Huntington's disease, Alzheimer's disease, cerebral ischaemia, traumatic brain injury, epilepsy and migraine.

The activity of a chemical entity utilized in this invention as an antagonist of NR2B or a treatment for a disease or disorder of the central nervous system (CNS) may be assayed in vitro or in vivo. An in vivo assessment of the efficacy of the compounds of the invention may be made using an animal model of a disease or disorder of the CNS, e.g., a rodent or primate model. Cell-based assays may be performed using, e.g., a cell line isolated from a tissue that expresses NR2B, or a cell line that recombinantly expresses NR2B. Additionally, biochemical or mechanism-based assays, e.g., measuring cAMP or cGMP levels, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with chemical entities of the invention. Alternate in vitro assays quantify the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an antagonist of NR2B are set forth in the Examples below. The aforementioned assays are exemplary and not intended to limit the scope of the invention. A person skilled in the art can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The chemical entities and compositions, according to the method of the present invention, may be administered using any amount and any route of administration effective for treating or lessening the severity of a CNS disease or disorder.

In some embodiments, the chemical entities and compositions, according to the method of the present invention, may be administered using any amount and any route of administration effective for treating or lessening the severity of a disease or disorder associated with NR2B.

In some embodiments, the chemical entities and compositions, according to the method of the present invention, may be administered using any amount and any route of administration effective for treating or lessening the severity of a CNS disease or disorder.

In some embodiments, the disease or disorder is depression with or without concomitant anxiety disorder, e.g., single episode and recurrent depressive disorder, dysthymic disorder, treatment-resistant depression (TRD, i.e., major depressive disorder that has not responded to other drug therapies).

In some embodiments, the disease or disorder is an acute affective disorder, e.g., selected from bipolar disorders including bipolar I and bipolar II manic disorders.

In some embodiments, the disease or disorder is pain, e.g., selected from pain states arising from a variety of sources including inflammation, nerve damage, diabetic neuropathy and post-herpetic neuralgia. In some embodiments, the disease or disorder is associated with intractable, such as migraine, fibromyalgia, and trigeminal neuralgia.

In some embodiments, the disease or disorder is selected from sleep disorders and their sequelae including insomnia, narcolepsy and idiopathic hypersomnia.

In some embodiments, the disease or disorder is selected from CNS disorders characterized by neuronal hyperexcitablity, such as epilepsy, convulsions and other seizure disorders.

In some embodiments, the disease or disorder is Parkinson's disease.

In some embodiments, the disease or disorder is Huntington's disease.

In some embodiments, the disease or disorder is cognitive dysfunction associated with disorders including schizophrenia, Alzheimer's disease, fronto-temporal dementia, Pick's disease, Lewy body disease, and other senile dementias (e.g., vascular dementia).

In some embodiments, the present invention provides a method of treating a disorder described herein, comprising administering a chemical entity of the invention in conjunction with one or more pharmaceutical agents. Suitable pharmaceutical agents that may be used in combination with the chemical entities of the present invention include selective serotonin reuptake inhibitors (SSRIs), e.g., in the treatment of depression; dopamine replacement therapy regimens and dopamine agonists, e.g., in the treatment of Parkinson's disease; typical antipsychotics; atypical antipsychotics; anticonvulsants; stimulants; Alzheimer's disease therapies; anti-migraine agents; and anxiolytic agents.

Suitable SSRIs include citalopram, dapoxetine, escitalopram, fluoxetine, fluvoxamine, indalpine, paroxetine, sertraline, vilazodone and zimelidine.

Suitable dopamine replacement therapy regimens include replacement of L-DOPA with a DOPA decarboxylase inhibitor such as carbidopa.

Suitable dopamine receptor agonists include aplindore, apomorphine, bromocriptine, cabergoline, ciladopa, dihydroergocryptine, lisuride, pardoprunox, pergolide, piribedil, pramipexole, ropinirole and rotigotine.

Suitable typical antipsychotics include chlorpromazine, thioridazine, mesoridazine, levomepromazine, loxapine, molindone, perphenazine, thiothixene, trifluoperazine, haloperidol, fluphenazine, droperidol, zuclopenthixol, flupentixol and prochlorperazine.

Suitable atypical antipsychotics include amisulpride, aripiprazole, asenapine, blonanserin, clotiapine, clozapine, iloperidone, llurasidone, mosapramine, olanzapine, paliperidone, perospirone, quetiapine, remoxipride, risperidone, sertindole, sulpiride, ziprasidone, zotepine, bifeprunox, pimavanserin and vabicaserin.

Suitable anticonvulsants include carbamazepine, lamotrigine, topiramate and divalproex.

Suitable stimulants include Adderall (amphetamine, dextroamphetamine mixed salts), methylphenidate, dextroamphetamine, dexmethylphenidate and lisdexamfetamine.

Suitable Alzheimer's disease therapies include acetylcholinesterase inhibitors such as rivastigmine, donepezil, galanthamine and huperazine; alpha-7 nicotinic agonists such as encenicline; and drugs that reduce Aβ42 such as BACE inhibitors, gamma secretase modulators and beta amyloid peptide antibodies.

Suitable anti-migraine drugs include ergotamine and 5-HT1D agonist triptans such as sumitriptan.

Suitable anxiolytic drugs include benzodiazepine receptor modulators such as diazepam, alprazolam, lorazepam and clonazepam.

Other suitable agents for use in conjunction with a chemical entity of the invention include memantine and modafinil.

The exact amount required will vary from subject to subject, depending on the species, age, and general condition of the subject, the severity of the infection, the particular agent, its mode of administration, and the like. The chemical entities of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the chemical entities and compositions of the present invention will be decided by the attending physician within the scope of sound medical judgment. The specific effective dose level for any particular patient or organism will depend upon a variety of factors including the disorder being treated and the severity of the disorder; the activity of the specific chemical entity employed; the specific composition employed; the age, body weight, general health, sex and diet of the patient; the time of administration, route of administration, and rate of excretion of the specific chemical entity employed; the duration of the treatment; drugs used in combination or coincidental with the specific chemical entity employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the chemical entities of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a chemical entity of the present invention, it is often desirable to slow the absorption of the chemical entity from subcutaneous or intramuscular injection. This may be accomplished by the use of a liquid suspension of crystalline or amorphous material with poor water solubility. The rate of absorption of the chemical entity then depends upon its rate of dissolution that, in turn, may depend upon crystal size and crystalline form. Alternatively, delayed absorption of a parenterally administered chemical entity form is accomplished by dissolving or suspending the chemical entity in an oil vehicle. Injectable depot forms are made by forming microencapsule matrices of the chemical entity in biodegradable polymers such as polylactide-polyglycolide. Depending upon the ratio of chemical entity to polymer and the nature of the particular polymer employed, the rate of chemical entity release can be controlled. Examples of other biodegradable polymers include poly(orthoesters) and poly(anhydrides). Depot injectable formulations are also prepared by entrapping the chemical entity in liposomes or microemulsions that are compatible with body tissues.

Compositions for rectal or vaginal administration are preferably suppositories which can be prepared by mixing the chemical entities of this invention with suitable non-irritating excipients or carriers such as cocoa butter, polyethylene glycol or a suppository wax which are solid at ambient temperature but liquid at body temperature and therefore melt in the rectum or vaginal cavity and release the active chemical entity.

Solid dosage forms for oral administration include capsules, tablets, pills, powders, and granules. In such solid dosage forms, the active chemical entity is mixed with at least one inert, pharmaceutically acceptable carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active chemical entities can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active chemical entity may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a chemical entity of the invention include ointments, pastes, creams, lotions, gels, powders, solutions, sprays, inhalants or patches. The active chemical entity is admixed under sterile conditions with a pharmaceutically acceptable carrier and any needed preservatives or buffers as may be required. Ophthalmic formulation, ear drops, and eye drops are also contemplated as being within the scope of the invention. Additionally, the present invention contemplates the use of transdermal patches, which have the added advantage of providing controlled delivery of a chemical entity to the body. Such dosage forms can be made by dissolving or dispensing the chemical entity in the proper medium. Absorption enhancers can also be used to increase the flux of the chemical entity across the skin. The rate can be controlled by either providing a rate controlling membrane or by dispersing the chemical entity in a polymer matrix or gel.

As used herein, the term "combination," "combined," and related terms refers to the simultaneous or sequential administration of therapeutic agents in accordance with this invention. For example, a chemical entity of the present invention may be administered with another therapeutic agent simultaneously or sequentially in separate unit dosage forms or together in a single unit dosage form. Accordingly, the present invention provides a single unit dosage form comprising a chemical entity of formula I, an additional therapeutic agent, and a pharmaceutically acceptable carrier, adjuvant, or vehicle.

The amount of both, a provided chemical entity and additional therapeutic agent (in those compositions which comprise an additional therapeutic agent as described above), that may be combined with the carrier materials to produce a single dosage form will vary depending upon the host treated and the particular mode of administration. Preferably, compositions of this invention should be formulated so that a dosage of between 0.01-100 mg/kg body weight/day of a provided chemical entity can be administered.

In those compositions which comprise an additional therapeutic agent, that additional therapeutic agent and the chemical entity of this invention may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one chemical entity of formula I and a pharmaceutically acceptable carrier, adjuvant or vehicle.

In some embodiments, the present invention provides the use of a chemical entity of formula I in the manufacture of a medicament for the treatment of a CNS disease or disorder.

General Synthetic Methods

Chemical entities of formula I can be synthesized according to Scheme 1 or Scheme 2 and/or using methods known in the art.

($OSO_2CF_2CF_2CF_2CF_3$). The alkylation reaction can be conducted in suitable protic (e.g. isopropanol, n-butanol) or aprotic (e.g. $CH_2Cl_2$, DMF, DMSO, $CH_3CN$) solvents at temperatures from ambient to 160° C., preferably between 50° C. and 100° C. (e.g. 40-80° C.) in the presence of a suitable base (e.g. triethylamine, diisopropylethylamine). In the case where intermediates of formula X have Z=H and X', $R^{1'}$, $R^{2'}$ and $R^{3'}$ in the intermediates of formula XI are as defined above for X, $R^1$, $R^2$ and $R^3$, the alkylation products of formula XII are compounds of formula I. Alternatively in

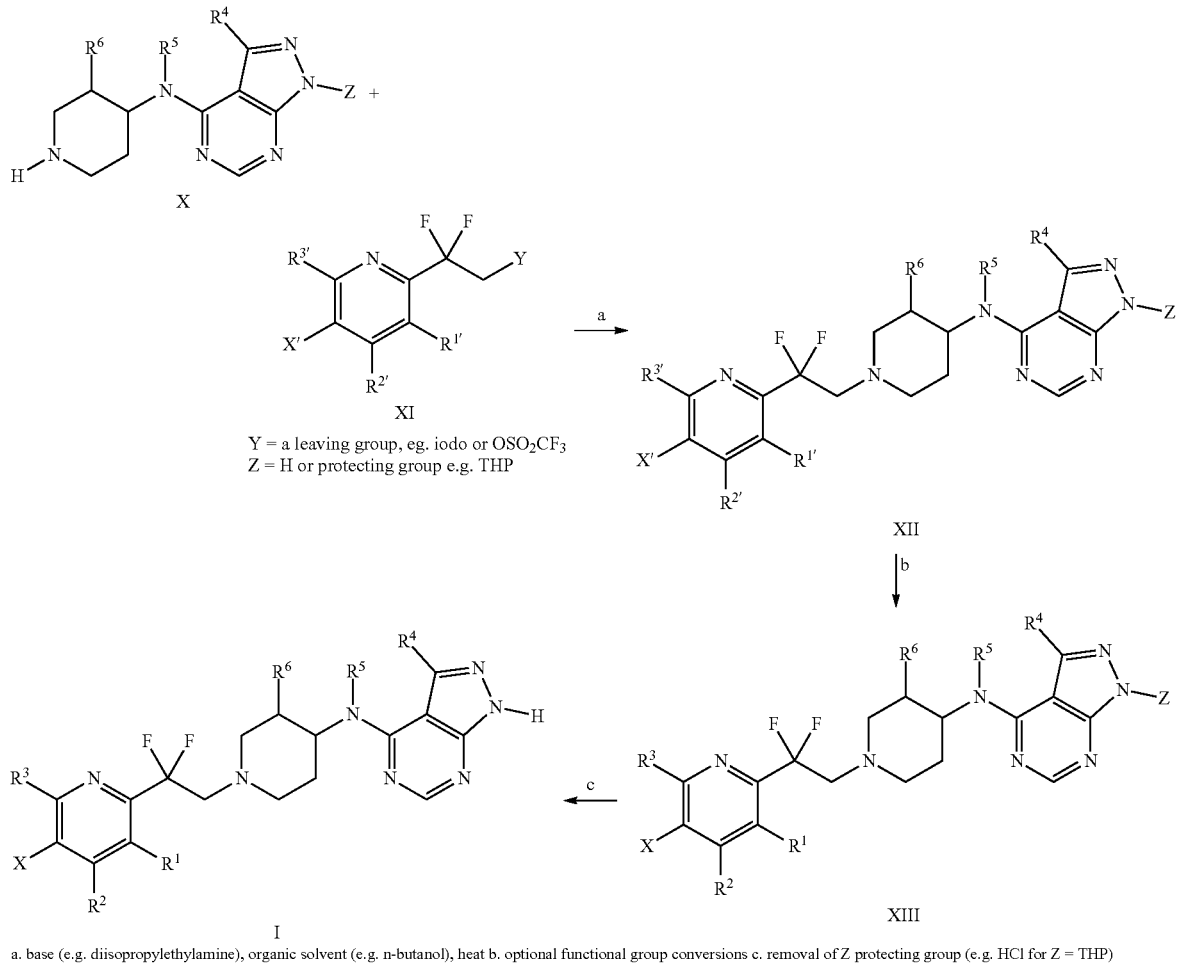

Scheme 1

Y = a leaving group, eg. iodo or $OSO_2CF_3$
Z = H or protecting group e.g. THP a. base (e.g. diisopropylethylamine), organic solvent (e.g. n-butanol), heat b. optional functional group conversions c. removal of Z protecting group (e.g. HCl for Z = THP)

In the method depicted in Scheme 1, in a first step, compounds of formula XII may be prepared by piperidine nitrogen alkylation of intermediates of general formula X, wherein Z is hydrogen or a suitable protecting group (e.g. THP (2-tetrahydropyranyl)) and $R^4$, $R^5$ and $R^6$ are as defined above, with pyridine intermediates of general formula XI wherein X', $R^{1'}$, $R^{2'}$ and $R^{3'}$ are as defined above for X, $R^1$, $R^2$ and $R^3$, or are independently suitably masked equivalents thereof. The Y group in alkylating intermediates of general formula XI represents an anionic leaving group such as halogen (chlorine, bromine or iodine) or a sulfonate group such as mesylate, tosylate, triflate ($OSO_2CF_3$) or nonaflate an optional step or steps, compounds of formula XII containing one or more X', $R^{1'}$, $R^{2'}$ or $R^{3'}$ substituents as suitably masked groups can be converted using methods known in the art to yield compounds of formula XIII wherein X, $R^1$, $R^2$ and $R^3$ are as defined above (e.g. for a compound of formula XII in which X'=$NO_2$, a hydrogenation step yields a compound of formula XIII in which X=$NH_2$). Intermediates of formula XIII in which Z is a protecting group can be converted to compounds of formula I using methods known in the art (e.g. when Z=a THP protecting group, using aqueous HCl in a suitable organic solvent).

An alternate method to synthesizing compounds of formula I is depicted in Scheme 2.

Scheme 2

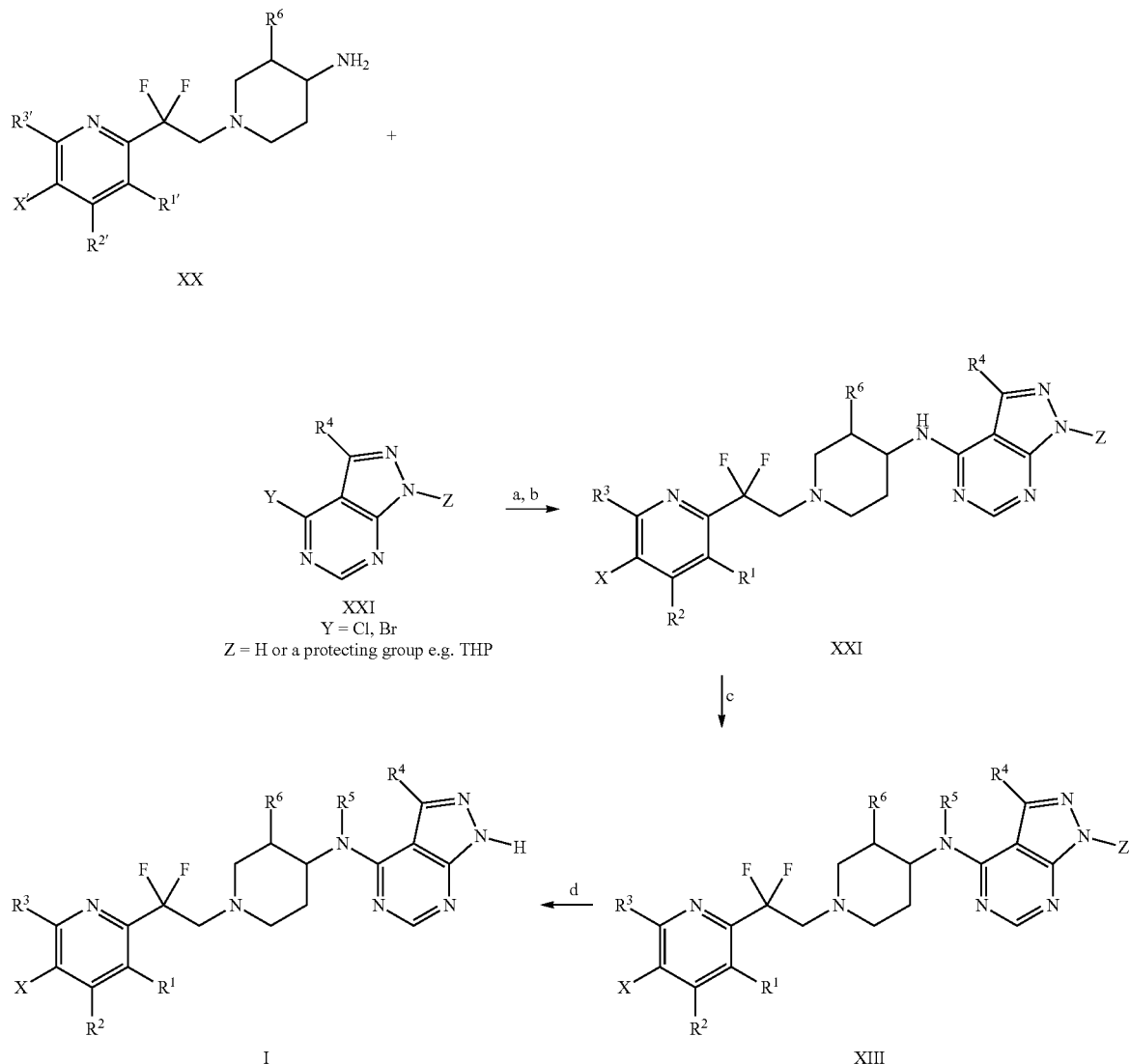

a. base or Buchwald reaction mediated amine coupling reaction conditions b. optimal steps e.g. functional group conversions and removal of Z protecting group c. base, R⁵X d. removal of Z protecting group In a first step, base or Buchwald reaction mediated coupling of intermediates of formula XX, wherein X', R¹', R²' and R³' in the intermediates of formula XI are as defined above for X, R¹, R² and R³, or are independently suitably masked equivalents thereof, with pyrazolopyrimidine intermediates of formula XXI wherein Z is hydrogen or a suitable protecting group, R⁴ is as defined above and Y is suitable leaving group, yields compounds of formula XXII. In certain cases base mediated coupling is suitable and can be conducted in an organic solvent (e.g. NMP, DMF, DMSO, CH₃CN) at temperatures from 50° C. to 180° C., preferably between 70° C. and 120° C. in the presence of a suitable tertiary amine base (e.g. triethylamine, diisopropylethylamine). In certain cases Buchwald conditions using a palladium catalyst can be used for the coupling reaction. To prepare intermediates of formula XIII in which R⁵ is methyl, compounds of formula XXII can be treated with a suitable base (e.g. NaH) in a suitable aprotic organic solvent (e.g. DMF) followed by the addition of a methylating reagent (e.g. methyliodide or dimethylsulfate) at a suitable temperature. Intermediates of formula XIII in which Z is a protecting group can be converted to compounds of formula I using methods known in the art (e.g. when Z=a THP protecting group, using aqueous HCl in a suitable organic solvent).

Intermediate pyridines of general formula XI wherein X', R¹', R²' and R³' are as defined above for X, R¹, R² and R³, or are independently suitably masked equivalents thereof, can be synthesized according to Scheme 3 and/or using methods known in the art.

Scheme 3

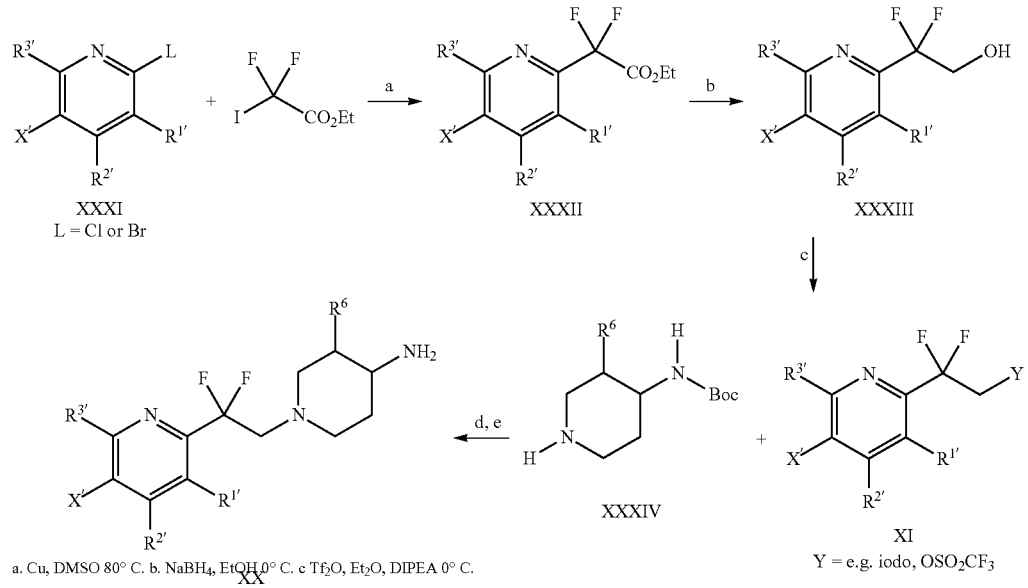

a. Cu, DMSO 80° C. b. NaBH₄, EtOH 0° C. c. Tf₂O, Et₂O, DIPEA 0° C.

Y = e.g. iodo, OSO₂CF₃

Starting 2-bromo or 2-chloropyridines of formula XXXI can be purchased, or synthesized using methods known in the art e.g. by Sandmeyer reaction from the corresponding 2-amino pyridines. Copper mediated coupling of compounds of formula XXXI with ethyl 2,2-difluoro-2-iodoacetate at elevated temperature in dry DMSO yields intermediates of general formula XXXII. Subsequent ester group reduction under appropriate conditions e.g. using sodium borohydride in ethanol yields corresponding alcohols of general formula XXXIII. The alcohol group in compounds of general formula XXXIII can be converted to a suitable leaving group e.g. iodide or trifluoromethanesulfonate using methods known in the art. For example treatment with triflic anhydride in ether solvent with N,N-diisopropylethylamine at 0° C. can be used to prepare trifluoromethane sulfonates of formula XI (Y=OSO₂CF₃). Alkylation of 4-Boc amino piperidines of formula XXXIV with intermediates of formula XI yields compounds of formula XX. The alkylation reaction can be conducted in suitable aprotic (e.g. CH₂Cl₂, DMF, DMSO, CH₃CN) solvents at temperatures from −10° C. to 100° C. (preferably from 0° C. to 80° C.) in the presence of a suitable base (e.g. triethylamine, diisopropylethylamine).

Intermediates of general formula X wherein X', R¹', R²' and R³' are as defined above for X, R¹, R² and R³, or are independently suitably masked equivalents thereof, can be synthesized according to Scheme 4 and/or using methods known in the art.

Scheme 4

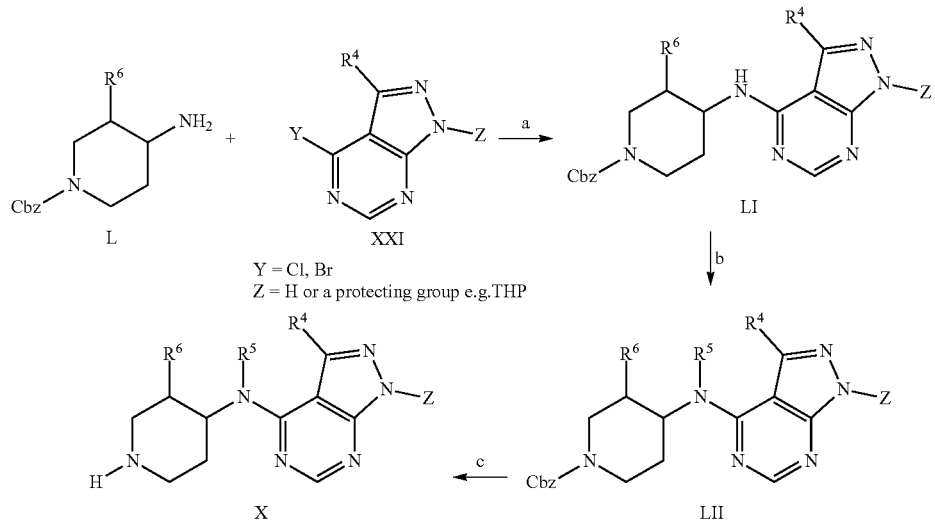

Y = Cl, Br
Z = H or a protecting group e.g. THP a. base or Buchwald reaction mediated amine coupling reaction conditions b. optional introduction of R⁵ group using alkylation conditions e.g. base, R⁵I c. Cbz removal e.g. by catalytic hydrogenation H₂/Pd-C/EtOH In a first step, starting 4-amino-N-benzyloxycarbonyl protected piperidines of formula L can be coupled with intermediates of formula XXI under base or Buchwald reaction conditions to give intermediates of general formula LI. In an optional second step, an $R^5$ group can be introduced by alkylation reaction to give intermediates of general formula LII in which $R^5$ is other than hydrogen. In final step the Cbz protecting group can be removed by catalytic hydrogenation or alternative methods known in the art to give intermediates of general formula X.

Intermediates of general formula XXI wherein $R^4$ is $C_1$-$C_3$ alkyl or cyclopropyl can be synthesized according to Scheme 5 and/or using methods known in the art.

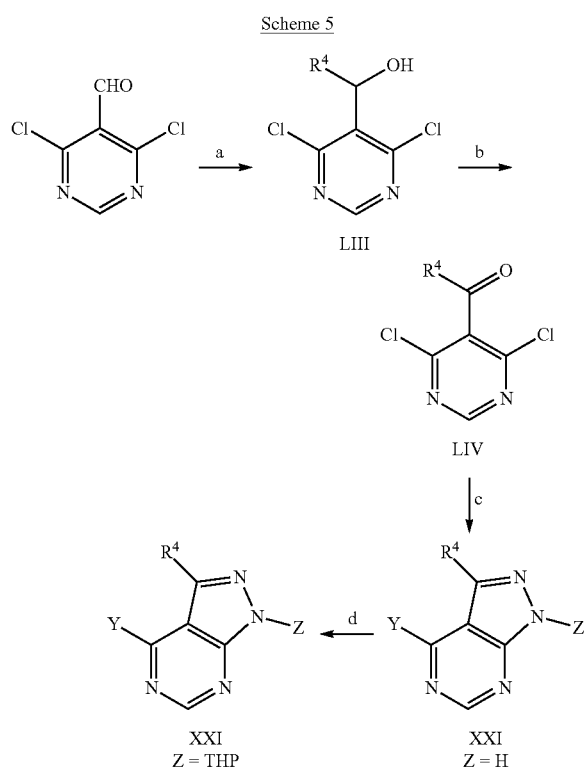

Scheme 5 a. $R^4$MgBr, ether  b. oxidation  c. hydrazine hydrate  d. dihydropyran, $CH_2Cl_2$, p-TsOH In a first step, 4,6-dichloropyrimidine-5-carboxaldehyde is reacted with a Grignard reagent, e.g. $R^4$MgBr, as would be derived from the corresponding bromide $R^4$Br using conditions known in the art, to give alcohols of general formula LIII. Oxidation of intermediates of formula LIII under conditions known in the art for preparing ketones from benzylic secondary alcohols, e.g. using Dess Martin reagent, $MnO_2$ or $CrO_3$ gives intermediates of formula LIV. Treatment of intermediates of formula LIV with hydrazine gives compounds of general formula XXI wherein $R^4$ is $C_1$-$C_3$ alkyl or cyclopropyl and Z is hydrogen. The latter may be treated with dihydropyran in an aprotic organic solvent (e.g. $CH_2Cl_2$) with an acid catalyst (e.g. p-toluenesulfonic acid) to give compounds of general formula XXI wherein $R^4$ is $C_1$-$C_3$ alkyl or cyclopropyl and Z is a tetrahydropyranyl protecting group.

EXAMPLES

As depicted in the Examples below, in certain exemplary embodiments, chemical entities are prepared according to the following procedures. It will be appreciated that, although the general methods depict the synthesis of certain chemical entities of the present invention, the following methods, and other methods known to persons skilled in the art, can be applied to all chemical entities and subclasses and species of each of these chemical entities, as described herein.

Temperatures are given in degrees centigrade. If not mentioned otherwise, all evaporations are performed under reduced pressure, preferably between 15 mm Hg and 100 mm Hg. The structures of intermediates and final products are confirmed by standard analytical methods, for example, mass spectrometry and NMR spectroscopy.

Abbreviations
aq aqueous
Boc t-butoxycarbonyl
Cbz benzyloxycarbonyl
DCM dichloromethane
DCE 1,2-dichloroethane
DIPEA N,N-diisopropylethylamine
DMF N,N-dimethylformamide
DMSO dimethyl sulfoxide
$Et_2O$ diethyl ether ("ether")
EtOAc ethyl acetate
EtOH ethanol
eq equivalents
h hours
HPLC high performance liquid chromatography
LC liquid chromatography
Me methyl
MS mass spectrometry
MS (ESI) mass spectrometry electrospray ionization
NMP N-methyl-2-pyrrolidone
NMR nuclear magnetic resonance
PEG polyethylene glycol
rt room temperature
Tf triflate
$Tf_2O$ triflic anhydride
TFAA trifluoroacetic anhydride
THF tetrahydrofuran
TLC thin layer chromatography Example 1

Chemical Entities

Example 1.A

Intermediates

Example 1.A.1

Intermediate 1

4-chloro-1H-pyrazolo[3,4-d]pyrimidine

To a suspension of allopurinol (2.0 g, 15 mmol) in toluene (20 mL) was added POCl₃ (7 mL, 74 mmol) and DIPEA (6 mL, 32 mmol). The mixture was heated to 85° C. with stirring for 2 hrs. The mixture was allowed to cool, concentrated to half of the volume and poured into 2M K₂HPO₄ (200 mL). The mixture was stirred overnight at room temperature and filtered. The filter mass was washed with EtOAc, and the filtrate was extracted with EtOAc. The combined organic phases were washed with brine, dried over Na₂SO₄ and concentrated to afford the title compound as pale orange powder (1.6 g, 70%). MS (ESI) calcd for C₅H₃ClN₄: 154.0; found: 155 [M+H]. ¹H NMR (400 MHz, DMSO) δ 14.47 (brs, 1H), 8.82 (s, 1H), 8.43 (s, 1H).

Example 1.A.2

Intermediate 2

4-chloro-1-(tetrahydro-2H-pyran-2-yl)-1H-pyrazolo[3,4-d]-pyrimidine

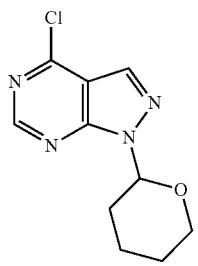 [SMILES: Clc1ncnc2c1cnn2C1CCCCO1]

To a solution of 4-chloro-1H-pyrazolo[3,4-d]pyrimidine (35 g, 226 mmol) in THF (1 L) was added dihydropyran (31 mL, 340 mmol) and p-TsOH.H₂O (4.3 g, 22.6 mmol). The solution was heated to reflux. After stirring for 1 h, another batch of dihydropyran (16 mL, 175 mmol) was added. After stirring for additional 1 h, the solution was concentrated and purified by column chromatography over silica gel (DCM/EtOAc=2%~10%) to afford the title compound as a white powder (50 g, 90%). MS (ESI) calcd for C₁₀H₁₁ClN₄O: 238; found: 239 [M+H]. ¹H NMR (400 MHz, CDCl₃) δ 8.80 (s, 1H), 8.20 (s, 1H), 6.11-5.99 (m, 1H), 4.16-4.05 (m, 1H), 3.85-3.74 (m, 1H), 2.69-2.57 (m, 1H), 2.24-2.11 (m, 1H), 2.05-1.94 (m, 1H), 1.87-1.71 (m, 2H), 1.71-1.59 (m, 1H).

Example 1.A.3

Intermediate 3

N-(piperidin-4-yl)-1-(tetrahydro-2H-pyran-2-yl)-1H-pyrazolo[3,4-d]-pyrimidin-4-amine

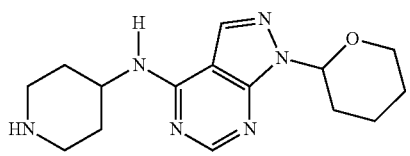

Step 1: benzyl 4-(1-(tetrahydro-2H-pyran-2-yl)-1H-pyrazolo[3,4-d]pyrimidin-4-ylamino)-piperidine-1-carboxylate

A mixture of 4-chloro-1-(tetrahydro-2H-pyran-2-yl)-1H-pyrazolo[3,4-d]pyrimidine (5.0 g, 21 mmol), benzyl 4-aminopiperidine-1-carboxylate (5.9 g, 25 mmol) and DIPEA (7.5 g, 43 mmol) in isopropanol (100 mL) was heated to 85° C. under N₂ atmosphere. After stirring overnight at 85° C., the resulting solution was cooled to rt and concentrated. The concentrate was purified by column chromatography over silica gel (25% of DCM/EtOAc) to afford the title compound as a white powder (6.4 g, 70%). MS (ESI) calcd for C₂₃H₂₈N₆O₃: 436; found: 437 [M+H]. ¹H NMR (400 MHz, CDCl₃) δ 8.41 (s, 1H), 7.93 (s, 1H), 7.41-7.29 (m, 5H), 5.99-5.91 (m, 1H), 5.32 (s, 1H), 5.14 (s, 2H), 4.41-4.15 (m, 3H), 4.15-4.08 (m, 1H), 3.83-3.75 (m, 1H), 3.04 (m, 2H), 2.62-2.51 (m, 1H), 2.17-2.07 (m, 3H), 1.97-1.89 (m, 1H), 1.82-1.72 (m, 2H), 1.55-1.43 (m, 2H).

Step 2: N-(piperidin-4-yl)-1-(tetrahydro-2H-pyran-2-yl)-1H-pyrazolo[3,4-d]-pyrimidin-4-amine

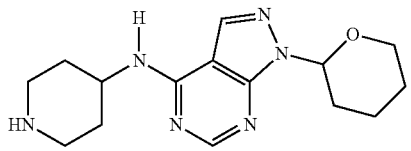 [SMILES: c1nc(NC2CCNCC2)c2cnn(C3CCCCO3)c2n1]

To a solution of benzyl 4-(1-(tetrahydro-2H-pyran-2-yl)-1H-pyrazolo[3,4-d]pyrimidin-4-ylamino)piperidine-1-carboxylate (7.76 g, 17.8 mmol) in 10% of MeOH/THF (100 mL) was added 10% Pd/C. The mixture was hydrogenated for 36 hours at 30° C. The mixture was filtered concentrated to afford the title compound as an off-white powder (5.3 g, 100%). MS (ESI) calcd for C₁₅H₂₂N₆O: 302; found: 303 [M+H]. ¹H NMR (400 MHz, CDCl₃) δ 8.39 (s, 1H), 7.92 (s, 1H), 5.99-5.91 (m, 1H), 5.48-5.14 (m, 1H), 4.33-4.15 (m, 1H), 4.14-4.08 (m, 1H), 3.83-3.74 (m, 1H), 3.19-3.09 (m, 2H), 2.83-2.73 (m, 2H), 2.63-2.49 (m, 1H), 2.16-2.06 (m, 3H), 1.97-1.89 (m, 1H), 1.79-1.72 (m, 2H), 1.71-1.65 (m, 1H), 1.64-1.56 (m, 1H), 1.54-1.42 (m, 2H).

Example 1.1

N-(1-(2,2-difluoro-2-(pyridin-2-yl)ethyl)piperidin-4-yl)-1H-pyrazolo[3,4-d]pyrimidin-4-amine (C-1)

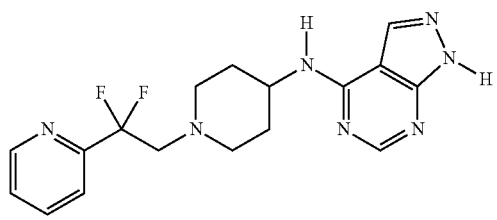 [SMILES: FC(F)(CN1CCC(Nc2ncnc3[nH]ncc23)CC1)c1ccccn1]

Step 1: ethyl 2,2-difluoro-2-(pyridin-2-yl)acetate

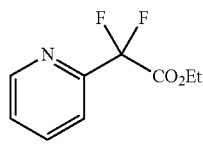 [SMILES: CCOC(=O)C(F)(F)c1ccccn1]

To a solution of 2-bromopyridine (1.0 g, 6.3 mmol) and ethyl 2-bromo-2,2-difluoroacetate (1.2 mL, 1.5 mmol) in DMSO (10 mL) was added copper powder (800 mg, 12.6 mmol). The mixture was heated to 90° C., and stirred overnight. The mixture was poured into water, and stirred for 1 h at room temperature. The final suspension was filtered through a pad of celite, and the filter mass was washed with EtOAc. The combined organic phases were washed with water and brine, dried over $Na_2SO_4$ and concentrated in vacuo to afford the crude title compound as yellow oil (1.1 g, 86%) which was used directly in the next step.

Step 2: 2,2-difluoro-2-(pyridin-2-yl)ethanol

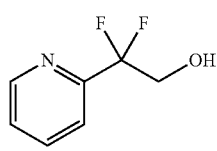 [SMILES: OCC(F)(F)c1ccccn1]

To a solution of ethyl 2,2-difluoro-2-(pyridin-2-yl)acetate (1.1 g, 5.78 mmol) in ethanol (25 mL) was added $NaBH_4$ (330 mg, 8.67 mmol) at room temperature. After stirring for 30 min, the mixture was quenched with aqueous 1M HCl at ice bath temperature. The mixture was basified with aqueous 1M NaOH, and extracted with EtOAc. The combined EtOAc phases were washed with brine, dried over $Na_2SO_4$ and concentrated in vacuo. The crude product was purified by column chromatography over silica gel (hexane/EtOAc=2/1) to afford the title compound as white solid (520 mg, 60%). $^1$H NMR (400 MHz, $CDCl_3$) δ 8.61 (d, J=4.7 Hz, 1H), 7.88 (td, J=7.8, 1.7 Hz, 1H), 7.73 (d, J=7.8 Hz, 1H), 7.43 (dd, J=7.2 and 4.7 Hz, 1H), 4.26 (dt, J=7.0 and 12.4 Hz, 2H), 3.50 (t, J=7.0 Hz, 1H).

Step 3: 2,2-difluoro-2-(pyridin-2-yl)ethyl trifluoromethanesulfonate

To a solution of 2,2-difluoro-2-(pyridin-2-yl)ethanol (220 mg, 1.25 mmol) and DIPEA (0.35 mL, 1.88 mmol) in dry ether (10 mL) was added $Tf_2O$ (0.25 mL, 1.50 mmol) dropwise at 0° C. under nitrogen atmosphere. The pink suspension thus obtained was stirred for 2 hours at room temperature. The suspension was filtered through a pad of ceilite. The filtrate was concentrated in vacuo, and purified by column chromatography over silica gel (hexane/EtOAc=10/1) to afford the title compound as a colorless oil (320 mg, 87%). $^1$H NMR (400 MHz, $CDCl_3$) δ 8.67 (d, J=4.3 Hz, 1H), 7.89 (td, J=7.8 and 1.6 Hz, 1H), 7.75 (d, J=7.8 Hz, 1H), 7.47 (dd, J=7.8 and 4.3 Hz, 1H), 5.12 (t, J=12.0 Hz, 2H).

Step 4: N-(1-(2,2-difluoro-2-(pyridin-2-yl)ethyl)piperidin-4-yl)-1-(tetrahydro-2H-pyran-2-yl)-1H-pyrazolo[3,4-d]pyrimidin-4-amine

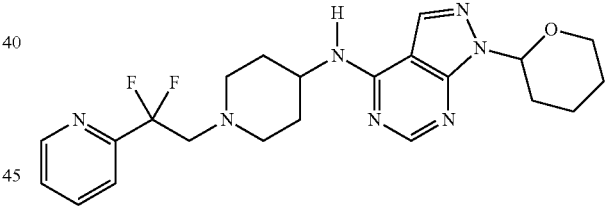

A solution of 2,2-difluoro-2-(pyridin-2-yl)ethyl trifluoromethanesulfonate (320 mg, 1.1 mmol), N-(piperidin-4-yl)-1-(tetrahydro-2H-pyran-2-yl)-1H-pyrazolo[3,4-d]pyrimidin-4-amine (330 mg, 1.1 mmol) and DIPEA (0.3 mL, 1.65 mmol) in DCM (5 mL) was heated to 40° C. After stirring overnight, the mixture was concentrated in vacuo and purified by column chromatography over silica gel (EtOAc) to afford the title compound as a white powder (406 mg, 83%). MS (ESI) calcd for $C_{22}H_{27}F_2N_7O$: 443.3; found: 444.3 [M+H]. $^1$H NMR (400 MHz, $CDCl_3$) δ 8.67 (d, J=4.3 Hz, 1H), 8.37 (s, 1H), 7.89 (s, 1H), 7.81 (td, J=7.7 and 1.6 Hz, 1H), 7.67 (d, J=7.7 Hz, 1H), 7.37 (dd, J=7.7 and 4.3 Hz, 1H), 5.95 (dd, J=10.6 and 2.0 Hz, 1H), 4.15-4.07 (m, 1H), 3.83-3.75 (m, 1H), 3.68-3.63 (m, 1H), 3.28 (t, J=14.5 Hz, 2H), 3.14-3.07 (m, 1H), 2.98-2.90 (m, 2H), 2.56-2.49 (m, 2H), 2.14-2.07 (m, 1H), 2.03-1.95 (m, 2H), 1.94-1.88 (m, 1H), 1.81-1.72 (m, 2H), 1.71-1.57 (m, 3H).

Step 5: N-(1-(2,2-difluoro-2-(pyridin-2-yl)ethyl) piperidin-4-yl)-1H-pyrazolo[3,4-d]pyrimidin-4-amine

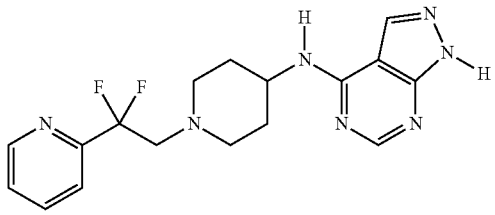 [SMILES: FC(F)(CN1CCC(Nc2ncnc3[nH]ncc23)CC1)c1ccccn1]

To a solution of N-(1-(2,2-difluoro-2-(pyridin-2-yl)ethyl) piperidin-4-yl)-1-(tetrahydro-2H-pyran-2-yl)-1H-pyrazolo [3,4-d]pyrimidin-4-amine (406 mg, 0.92 mol) in DCM (5 mL) was added the saturated HCl/Et$_2$O (5 mL). After stirred overnight at room temperature, the THP group was removed. The suspension was concentrated in vacuo, and basified with aqueous 1M NaOH. The basic aqueous mixture was extracted with DCM. The combined DMC phases were washed with brine, dried over Na$_2$SO$_4$ and concentrated in vacuo to give the title compound as a white powder (219 mg, 66%). MS (ESI) calcd for C$_{17}$H$_{19}$F$_2$N$_7$: 359.2; found: 360.3 [M+H]. $^1$H NMR (400 MHz, CD$_3$OD) δ 8.64 (d, J=4.6 Hz, 1H), 8.20 (s, 1H), 8.09 (s, 1H), 8.00-7.93 (m, 1H), 7.74 (d, J=7.9 Hz, 1H), 7.52 (dd, J=7.9 and 4.6 Hz, 1H), 4.05-3.95 (m, 1H), 3.16 (t, J=14.4 Hz, 2H), 2.88-2.82 (m, 2H), 2.43-2.35 (m, 2H), 1.86-1.76 (m, 2H), 1.51-1.40 (m, 2H).

Example 1.1a (HCl salt)

N-(1-(2,2-difluoro-2-(pyridin-2-yl)ethyl)piperidin-4-yl)-1H-pyrazolo[3,4-d]pyrimidin-4-amine hydrochloride (C-1.HCl)

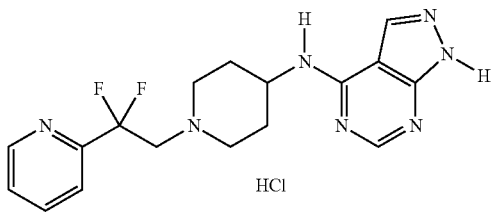 [SMILES: FC(F)(CN1CCC(Nc2ncnc3[nH]ncc23)CC1)c1ccccn1 ; Cl]

To a solution of N-(1-(2,2-difluoro-2-(pyridin-2-yl)ethyl) piperidin-4-yl)-1H-pyrazolo[3,4-d]-pyrimidin-4-amine (105 mg, 0.29 mmol) in MeOH (5 mL) was added a 2.0M methanolic solution of HCl (0.15 mL, 0.30 mmol). After stirring for 30 min, the solution was concentrated to afford the title compound as a white powder (115 mg, 100%). MS (ESI) calcd for C$_{17}$H$_{19}$F$_2$N$_7$: 359.2; found: 360.3 [M+H]. $^1$H NMR (400 MHz, CD$_3$OD) δ 8.62 (d, J=4.5 Hz, 1H), 8.44 (brs, 2H), 7.98-7.94 (m, 1H), 7.75 (d, J=7.9 Hz, 1H), 7.52 (dd, J=7.9 and 4.5 Hz, 1H), 4.51-4.35 (m, 1H), 4.16-4.00 (m, 2H), 3.72-3.60 (m, 2H), 3.32-3.20 (m, 2H), 2.30-2.20 (m, 2H), 2.07-1.95 (m, 2H).

Example 1.4

N-(1-(2,2-difluoro-2-(5-methylpyridin-2-yl)ethyl) piperidin-4-yl)-1H-pyrazolo[3,4-d]pyrimidin-4-amine (C-4)

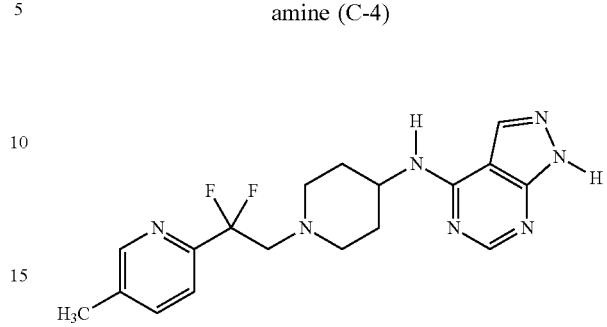

Step 1: ethyl 2,2-difluoro-2-(5-methylpyridin-2-yl)acetate

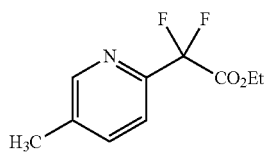

To a solution of ethyl 2-bromo-5-methylpyridine (4.0 g, 24 mmol) and ethyl 2-bromo-2, 2-difluoroacetate (4.8 g, 24 mmol) in DMSO (80 mL) was added Cu powder (3.0 g, 47 mmol). The mixture was heated to 50° C. overnight. The reaction mixture was filtered through celite and washed with ethyl acetate. The filtrate was extracted with ethyl acetate and washed with brine. The ethyl acetate layer was dried over sodium sulfate, filtered, and concentrated. The concentrate was purified by column chromatography over silica gel (hexane/ethyl acetate=100:1) to afford the title compound as a colorless liquid (3.7 g, 74%) $^1$H NMR (400 MHz, CDCl$_3$) δ 8.47 (s, 1H), 7.69-7.57 (m, 2H), 4.37 (q, J=7.1 Hz, 2H), 2.40 (s, 3H), 1.33 (t, J=7.1 Hz, 3H).

Step 2: 2,2-difluoro-2-(5-methylpyridin-2-yl)ethanol

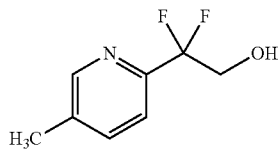

To a solution of ethyl 2, 2-difluoro-2-(5-methylpyridin-2-yl) acetate (2.0 g, 9.3 mmol) in ethanol (45 mL) was added NaBH$_4$ (500 mg, 13.4 mmol) slowly. The mixture was stirred for 30 min at rt. After 30 min, the reaction mixture was quenched with 1N HCl in ice-water bath, concentrated and extracted with ethyl acetate. The ethyl acetate layer was washed with water and brine, then dried and concentrated to afford the title compound as a white solid (1.6 g, 100%). $^1$H NMR (400 MHz, CDCl$_3$) δ 8.44 (s, 1H), 7.71 (d, J=8 Hz, 1H), 7.64 (d, J=8.0 Hz, 1H), 4.22 (t, J=12.4 Hz, 2H), 3.03 (brs, 1H), 2.41 (s, 3H).

Step 3: 2, 2-difluoro-2-(5-methylpyridin-2-yl) ethyl trifluoromethanesulfonate

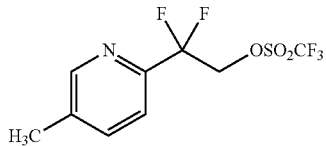

To a solution of 2,2-difluoro-2-(5-methylpyridin-2-yl) ethanol (800 mg, 4.6 mmol) and DIPEA (2.8 ml, 13.8 mmol) in anhydrous ether (40 ml) was added Tf$_2$O (1.5 ml, 9.2 mmol) at 0° C. After stirring for 1 hr at rt, the white suspension was filtered through celite, and the filtered mass was washed with ether. The filtrate was concentrated and purified by column chromatography over silica get(hexane) to afford the title compound as a colorless liquid (1.0 g, 70%). $^1$H NMR (400 MHz, CDCl$_3$) δ 8.47 (s, 1H), 7.65 (m, 2H), 5.10 (t, J=12.0 Hz, 2H), 2.42 (s, 3H).

Step 4: tert-buty 1 1-(2,2-difluoro-2-(5-methylpyridin-2-yl)ethyl)piperidin-4-yl-carbamate

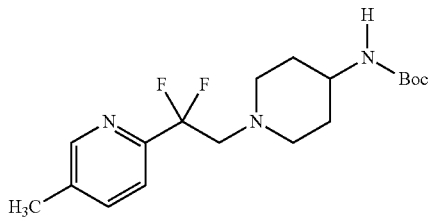 [SMILES: Cc1ccc(C(F)(F)CN2CCC(NC(=O)OC(C)(C)C)CC2)nc1]

A mixture of 2,2-difluoro-2-(5-methylpyridin-2-yl)ethyl trifluoromethanesulfonate (1.0 g, 3.3 mmol), tert-butyl piperidin-4-ylmethylcarbamate (1.3 g, 6.6 mmol) and DIPEA (2.0 ml, 9.9 mmol) in DCM (16 ml) was heated to 40° C. with stirring. After stirring overnight at 40° C., the mixture was concentrated to dryness. The concentrate was purified by column chromatography over silica gel (hexane/ethyl acetate=10/1) to afford the title compound as a yellow solid (1.0 g, 83%). MS (ESI) calcd for C$_{18}$H$_{27}$F$_2$N$_3$O$_2$: 355.2; found: 356.2[M+H]. $^1$H NMR (400 MHz, CDCl$_3$) δ 8.46 (s, 1H), 7.60-7.50 (m, 2H), 3.72-3.61 (m, 1H), 3.40 (brs, 1H), 3.19 (t, J=14.7 Hz, 2H), 2.85-2.80 (m, 2H), 2.38 (s, 3H), 2.32-3.40 (m, 2H), 1.82-1.78 (m, 2H), 1.43 (s, 9H), 1.25-1.30 (m, 2H).

Step 5: 1-(2,2-difluoro-2-(5-methylpyridin-2-yl)ethyl)piperidin-4-amine

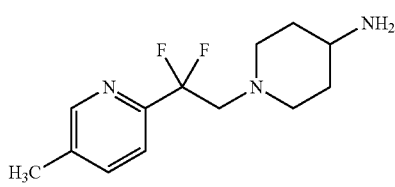 [SMILES: Cc1ccc(C(F)(F)CN2CCC(N)CC2)nc1]

To a solution of tert-butyl 1-(2, 2-difluoro-2-(5-methyl-pyridin-2-yl) ethyl) piperidin-4-ylcarbamate (1.0 g, 2.8 mmol) in DCM (15 ml) was added TFA (12.5 ml) at 0° C. After stirring for 30 min at rt., the mixture was concentrated. The concentrate was basified with 1 N NaOH and extracted with ethyl acetate. The organic phase was washed with brine, dried over Na$_2$SO$_4$, and concentrated to afford the title compound as an off-white powder (400 mg, 60%). MS (ESI) calcd for C$_{13}$H$_{19}$F$_2$N$_3$: 255.2; found: 256.2 [M+H]. $^1$H NMR (400 MHz, CDCl$_3$) δ 8.47 (s, 1H), 7.59-7.52 (m, 2H), 3.18 (t, J=14.6 Hz, 2H), 2.85-2.82 (m, 2H), 2.64-2.54 (m, 1H), 2.38 (s, 3H), 2.35-2.28 (m, 2H), 1.69-1.66 (m, 2H), 1.32-1.26 (m, 2H).

Step 6: N-(1-(2,2-difluoro-2-(5-methylpyridin-2-yl)ethyl)piperidin-4-yl)-1-(tetrahydro-2H-pyran-2-yl)-1H-pyrazolo[3,4-d]pyrimidin-4-amine

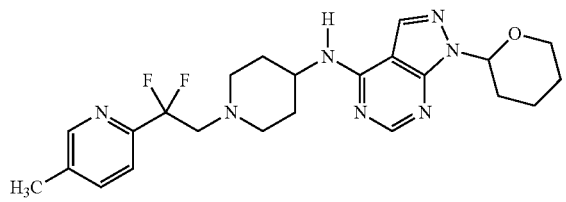 [SMILES: Cc1ccc(C(F)(F)CN2CCC(Nc3ncnc4c3cnn4C3CCCCO3)CC2)nc1]

A mixture of 1-(2, 2-difluoro-2-(5-methylpyridin-2-yl) ethyl) piperidin-4-amine (260 mg, 1.02 mmol), 4-chloro-1-(tetrahydro-2H-pyran-2-yl)-1H-pyrazolo[4, 3-c] pyridine (200 mg, 0.85 mmol) and DIPEA (0.35 ml, 1.7 mmol) in n-BuOH was stirred at 130° C. overnight. The orange solution was concentrated. The concentrate was taken up in ethylacetate and washed with water. The concentrate was purified by column chromatography over silica gel (hexane/ethyl acetate=4/1) to afford the title compound as a white solid (190 mg, 40%). MS (ESI) calcd for C$_{23}$H$_{29}$F$_2$N$_7$O: 457.3; found: 458.3 [M+H]. $^1$H NMR (400 MHz, CDCl$_3$) δ 8.48 (s, 1H), 8.38 (s, 1H), 7.88 (s, 1H), 7.64-7.53 (m, 2H), 5.97-5.94 (m, 1H), 4.16-4.07 (m, 1H), 3.84-3.75 (m, 1H), 3.26 (t, J=14.6 Hz, 2H), 2.95-2.92 (m, 2H), 2.55-2.49 (m, 2H), 2.39 (s, 3H), 2.11 (d, J=5.3 Hz, 1H), 2.02-1.99 (m, 2H), 1.94-1.92 (m, 1H), 1.84-1.70 (m, 2H), 1.54-1.51 (m, 2H), 1.31-1.25 (m, 4H).

Step 7: N-(1-(2,2-difluoro-2-(5-methylpyridin-2-yl)ethyl)piperidin-4-yl)-1H-pyrazolo[3,4-d]pyrimidin-4-amine

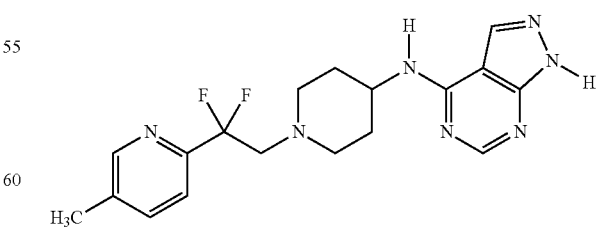

To a mixture of N-(1-(2,2-difluoro-2-(5-methylpyridin-2-yl)ethyl)piperidin-4-yl)-1-(tetrahydro-2H-pyran-2-yl)-1H-pyrazolo[3,4-d]pyrimidin-4-amine (190 mg, 0.41 mmol) in MeOH (3.5 ml) was added HCl/Et$_2$O (2M, 2.6 ml, 0.31 mmol) at rt. After stirring for 4 h, the mixture was concentrated and neutralized with 1N NaOH. The mixture was extracted with ethylacetate, washed with water and concentrated to give the title compound as white solid (145 mg, 98%). MS (ESI) calcd for $C_{18}H_{21}F_2N_7O$: 373.2; found: 374.3 [M+H]. $^1$H NMR (400 MHz, $CD_3OD$) δ 8.49 (s, 1H), 8.21 (s, 1H), 8.11 (s, 1H), 7.80 (d, J=8.0 Hz, 1H), 7.64 (d, J=8.0 Hz, 1H), 4.14-4.11 (m, 1H), 3.25 (t, J=14.4 Hz, 2H), 2.96-2.93 (m, 2H), 2.51-2.45 (m, 2H), 2.43 (s, 3H), 1.95-1.92 (m, 2H), 1.63-1.50 (m, 2H).

Example 1.4a (HCl salt)

N-(1-(2,2-difluoro-2-(5-methylpyridin-2-yl)ethyl) piperidin-4-yl)-1H-pyrazolo[3,4-d]pyrimidin-4-amine hydrochloride (C-4.HCl)

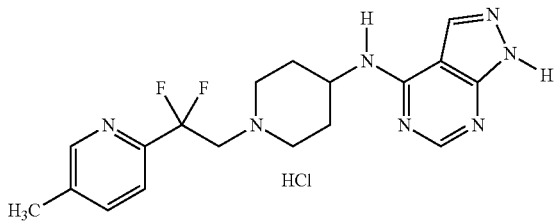

To the solution of N-(1-(2, 2-difluoro-2-(5-methylpyridin-2-yl) ethyl) piperidin-4-yl)-1H-pyrazolo[3,4-d] pyrimidin-4-amine (132 mg, 0.3 mmol) in MeOH(1.5 ml) was added HCl/$Et_2O$ (2M, 0.15 ml, 0.30 mmol).After stirring for 15 min, the mixture was concentrated to afford the title compound as an off-white powder (145 mg, 96%). MS (ESI) calcd for $C_{18}H_{21}F_2N_7O$: 373.2; found: 374.3 [M+H]. $^1$H NMR (400 MHz, $CD_3OD$) δ 8.56 (s, 1H), 8.37 (m, 2H), 7.88 (d, J=8.1 Hz, 1H), 7.74 (d, J=8.1 Hz, 1H), 4.43 (s, 1H), 4.04 (s, 2H), 3.64 (m, 2H), 3.26 (s, 3H), 2.31-2.27 (m, 2H), 2.14-1.90 (m, 2H), 1.35-1.31 (m, 2H).

Example 1.5

N-(1-(2,2-difluoro-2-(5-(trifluoromethyl)pyridin-2-yl)ethyl)piperidin-4-yl)-1H-pyrazolo[3,4-d]pyrimidin-4-amine (C-5)

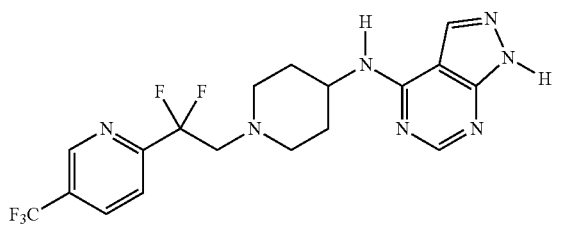 [SMILES: FC(F)(F)c1ccc(C(F)(F)CN2CCC(Nc3ncnc4[nH]ncc34)CC2)nc1]

Step 1: ethyl 2,2-difluoro-2-(5-(trifluoromethyl) pyridin-2-yl)acetate

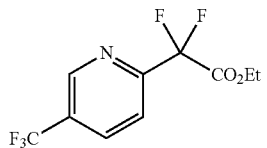

To a solution of ethyl 2,2-difluoro-2-iodoacetate (5.5 g, 22 mmol) and 2-bromo-5-trifluoromethyl-pyridine (5.0 g, 22 mmol) in DMSO (110 mL) was added Cu powder (2.8 g, 44 mmol). The mixture was heated to 80° C. for 20 hours. The reaction mixture was filtered through celite and the solid cake was washed with ethyl acetate. The filtrate was extracted with ethyl acetate. The ethyl acetate layers were combined, dried over sodium sulfate, filtered, and concentrated. The concentrate was purified by column chromatography over silica gel (hexane/ethyl acetate=100:1) to afford the title compound as a colorless liquid (2.5 g, 42%). $^1$H NMR (400 MHz, $CDCl_3$) δ 8.93 (s, 1H), 8.13 (d, J=7.9 Hz, 1H), 7.90 (d, J=8.1 Hz, 1H), 4.39 (q, J=7.1 Hz, 2H), 1.34 (t, J=7.1 Hz, 3H).

Step 2: 2,2-difluoro-2-(5-(trifluoromethyl)pyridin-2-yl)ethanol

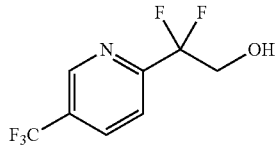

To a solution of ethyl 2, 2-difluoro-2-(5-(trifluoromethyl) pyridin-2-yl) acetate (1.0 g, 3.7 mmol) in ethanol (19 mL) was added $NaBH_4$ (200 mg, 5.3 mmol) slowly. The mixture was stirred for 30 min at rt. The stirred reaction mixture was cooled, quenched with 1N HCl, concentrated and extracted with ethyl acetate. The ethyl acetate layer was washed with water and brine, dried over sodium sulfate and concentrated to afford the title compound as a white solid (850 mg) which was used in the next step without further purification. $^1$H NMR (400 MHz, $CDCl_3$) δ 8.92 (s, 1H), 8.13 (d, J=8.0 Hz, 1H), 7.88 (d, J=8.0 Hz, 1H), 4.28 (t, J=12 Hz, 2H), 2.42 (s, 1H).

Step 3: 2, 2-difluoro-2-(5-(trifluoromethyl) pyridin-2-yl)ethyl trifluoromethanesulfonate

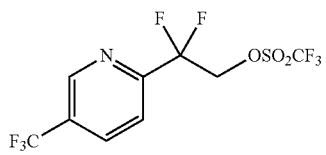

To a solution of 2, 2-difluoro-2-(5-(trifluoromethyl)pyridin-2-yl)ethanol (750 mg, 3.3 mmol) and DIPEA (2.0 ml, 9.9 mmol) in anhydrous ether (33 mL) was added $Tf_2O$ (1.1 ml, 6.6 mmol) at 0° C. After stirring for 1 hr at rt, the white suspension was filtered through celite. The solid mass was washed with ether. The filtrate was concentrated and purified by column chromatography over silica gel (hexane) to afford the title compound as a colorless liquid (760 mg, 75%). ¹H NMR (400 MHz, CDCl₃) δ 8.95 (s, 1H), 8.16 (d, J=8.2, 1H), 7.91 (d, J=8.2 Hz, 1H), 5.14 (t, J=11.8 Hz, 2H).

Step 4: tert-butyl-1-(2,2-difluoro-2-(5-(trifluoromethyl)pyridin-2-yl)ethyl)piperidin-4-ylcarbamate

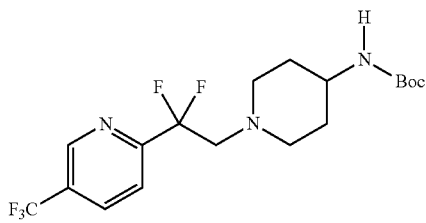

The mixture of 2,2-difluoro-2-(5-(trifluoromethyl)pyridin-2-yl)ethyl trifluoromethane-sulfonate (1.04 g, 2.9 mmol), tert-butyl piperidin-4-ylcarbamate (1.16 g, 5.8 mmol) and DIPEA (1.5 mL, 8.7 mmol) in DCM (20 mL) was heated to 40° C. After stirring overnight at 40° C., the mixture was concentrated and extracted with EtOAc. The organic layer was washed with water and brine, dried and concentrated. The concentrate was purified by column chromatography over silica gel (hexane/EtOAc=5:1) to afford the title compound as white solid (1.05 g, 92%). MS (ESI) calcd for C₁₈H₂₄F₅N₃O₂: 409.2; found: 410.2 [M+H]. ¹H NMR (400 MHz, CDCl₃) δ 8.91 (s, 1H), 8.05 (d, J=8.2 Hz, 1H), 7.78 (d, J=8.2 Hz, 1H), 4.34 (brs, 1H), 3.39 (m, 1H), 3.22 (t, J=14.2 Hz, 2H), 2.83-2.78 (m, 2H), 2.41-2.35 (m, 2H), 1.81-1.77 (m, 2H), 1.42 (s, 9H), 1.20-1.30 (m, 2H), Step 5: 1-(2,2-difluoro-2-(5-(trifluoromethyl)pyridin-2-yl)ethyl)piperidin-4-amine

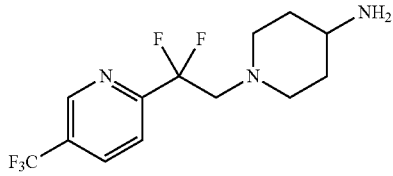

To the solution of tert-butyl 1-(2,2-difluoro-2-(5-(trifluoromethyl)pyridin-2-yl)ethyl)-piperidin-4-ylcarbamate (300 mg, 0.73 mmol) in DCM (8 mL) was added TFA (4.4 mL) at ice-water bath temperature. After stirring for 15 min at r.t., the mixture was concentrated.

The concentrate was basified with 1N NaOH, and extracted with EtOAc. The organic phase was washed with brine, dried over Na₂SO₄, and concentrated to afford the title compound as pale yellow oil (226 mg) which was used directly in the next step. MS (ESI) calcd for C₁₃H₁₆F₅N₃: 309.1; found: 310.3[M+H]. ¹H NMR (400 MHz, CDCl₃) δ 8.92 (s, 1H), 8.04 (d, J=8.2 Hz, 1H), 7.79 (d, J=8.2 Hz, 1H), 3.22 (t, J=14.1 Hz, 2H), 2.82-2.79 (m, 2H), 2.64-2.54 (m, 1H), 2.35-2.29 (m, 2H), 1.68-1.65 (m, 2H), 1.29-1.23 (m, 2H), 1.21-1.18 (m, 2H).

Step 6: N-(1-(2,2-difluoro-2-(5-(trifluoromethyl)pyridin-2-yl)ethyl)piperidin-4-yl)-1H-pyrazolo[3,4-d]pyrimidin-4-amine

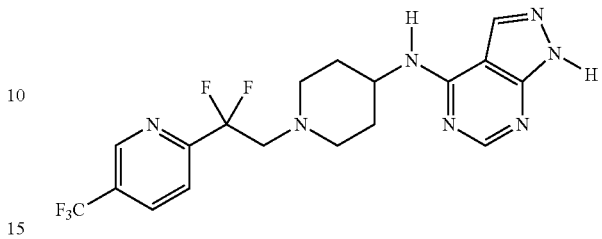

A mixture of 1-(2,2-difluoro-2-(5-(trifluoromethyl)pyridin-2-yl)ethyl)piperidin-4-amine (226 mg, 0.73 mmol), 4-chloro-1H-pyrazolo[3,4-d]pyrimidine (276 mg, 1.17 mmol) and DIPEA (0.35 mL, 1.95 mmol) in n-butyl alcohol (3 mL) was heated to 130° C. After stirring overnight at 130° C., the reaction mixture was concentrated and extracted with EtOAc. The organic layers were washed with water and brine, dried and concentrated. The concentrate was purified by column chromatography over silica gel (DCM/MeOH=25/1) to afford the title compound as a white solid (105 mg, 34% overall 2 step yield). MS (ESI) calcd for C₁₈H₁₈F₅N₇: 427.2; found: 428.2 [M+H]. ¹H NMR (400 MHz, CD₃OD) δ 9.01 (s, 1H), 8.32 (d, J=8.3, 1H), 8.21 (s, 1H), 8.09 (s, 1H), 7.96 (d, J=8.3 Hz, 1H), 4.08 (s, 1H), 2.97-2.92 (m, 2H), 2.51-2.46 (m, 2H), 1.96-1.91 (m, 2H), 1.56-1.48 (m, 2H).

Example 1.5a (HCl salt)

N-(1-(2,2-difluoro-2-(5-(trifluoromethyl)pyridin-2-yl)ethyl)piperidin-4-yl)-1H-pyrazolo[3,4-d]pyrimidin-4-amine hydrochloride (C-5.HCl)

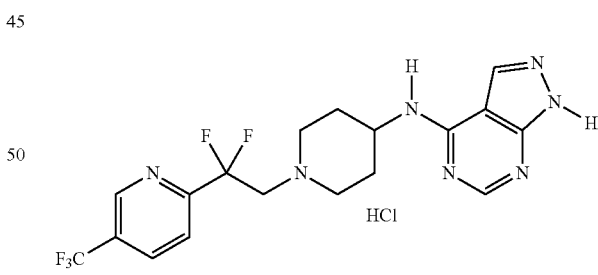

To the solution of N-(1-(2,2-difluoro-2-(5-(trifluoromethyl)pyridin-2-yl)ethyl)piperidin-4-yl)-1H-pyrazolo[3,4-d]pyrimidin-4-amine (100 mg, 0.234 mmol) in MeOH (3 mL) was added HCl/MeOH (2M, 0.13 mL, 0.234 mmol) at rt. After stirring for 10 min, the mixture was concentrated to afford the product as a light yellow solid (113 mg, 100%). MS (ESI) calcd for C₁₈H₁₈F₅N₇: 427.2 found: 428.2 [M+H]. ¹H NMR (400 MHz, CD₃OD) δ 9.06 (s, 1H), 8.45-8.32 (m, 3H), 8.05 (d, J=8.3 Hz, 1H), 4.40 (s, 1H), 3.94 (s, 2H), 3.52-3.48 (m, 2H), 3.20-3.05 (m, 2H), 2.42-2.22 (m, 2H), 1.95-1.85 (m, 2H).

Example 1.15

N-(1-(2-(3,5-difluoropyridin-2-yl)-2,2-difluoroethyl)piperidin-4-yl)-1H-pyrazolo[3,4-d]-pyrimidin-4-amine (C-15)

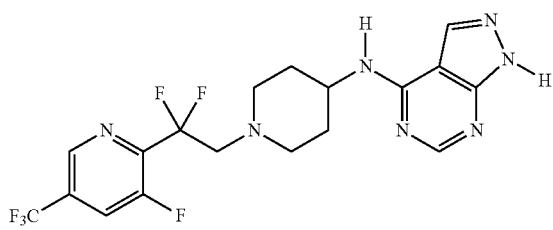

Step 1: 2-bromo-3,5-difluoropyridine

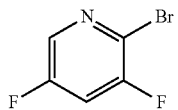

3,5-difluoropyridin-2-amine (2.0 g, 15 mmol) was slowly added to 48% HBr solution (10 mL) with stirring at 0° C. To the resulting mixture Br$_2$ (2.36 mL, 46 mmol) was then added over 20 minutes at 0° C. The reaction mixture was cooled to −10° C. A solution of NaNO$_2$ (2.65 g, 38 mmol) in water (10 mL) was added over 1.5 hours, and the mixture stirred for additional 30 minutes. A solution of NaOH (5.5 g, 138 mmol) in water (20 mL) was added over 30 minutes. and the mixture was allowed to warm to room temperature. The mixture was extracted with ether (3×100 mL). The combined organic phases were washed with brine, dried over sodium sulfate, filtered, and concentrated to afford the title compound as pale yellow solid (2.77 g, 92%) which was used directly without further purification. $^1$H NMR (400 MHz, CDCl$_3$) δ 8.12 (d, J=2.4 Hz, 1H), 7.35 (dt, J=2.4 and 7.6 Hz, 1H).

Step 2: ethyl 2-(3,5-difluoropyridin-2-yl)-2,2-difluoroacetate

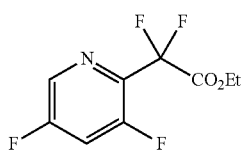

To the solution of 2-bromo-3,5-difluoropyridine (1.0 g, 5.2 mmol) and ethyl 2-bromo-2,2-difluoroacetate (1.05 g, 5.16 mmol) in DMSO (20 mL) was added Cu powder (6.6 g, 10.3 mmol). The mixture was stirred overnight at 50° C. The reaction mixture was poured into a solution of dibasic potassium hydrogen phosphate, trihydrate (10 g, 50 mmol) in water (100 mL) with vigorous stirring. The suspension was filtered and the solid was rinsed with EtOAc. The filtrate was added to brine and extracted with EtOAc (100 mL×2). The combined organics were washed with brine, dried over sodium sulfate, filtered, and concentrated. The concentrate was purified by column chromatography over silica gel (hexane/EtOAc=50:1) to afford the title compound as a colorless oil (890 mg, 73%). $^1$H NMR (400 MHz, CDCl$_3$) δ 8.35 (d, J=1.8 Hz, 1H), 7.44-7.31 (m, 1H), 4.42 (q, J=6.8 Hz, 2H), 1.36 (t, J=6.8 Hz, 3H).

Step 3: 2-(3,5-difluoropyridin-2-yl)-2,2-difluoroethanol

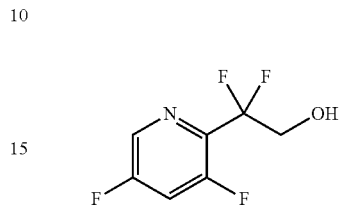

To the solution of ethyl 2-(3,5-difluoropyridin-2-yl)-2,2-difluoroacetate (800 mg, 3.37 mmol) in ethanol (20 mL) was added NaBH$_4$ (140 mg, 3.71 mmol) slowly at 0° C. The mixture was stirred for 1 hour at r.t. The reaction mixture was quenched with 1N HCl at ice-water bath temperature. The mixture was concentrated and extracted with EtOAc. The organic layer was washed with water and brine, dried and concentrated to afford the title compound as a white solid (535 mg, 81%). $^1$H NMR (400 MHz, CDCl$_3$) δ 8.33 (d, J=2.2 Hz, 1H), 7.38 (m, 1H), 4.27 (dt, J=7.6 and 12.4 Hz, 2H), 2.87 (t, J=7.6 Hz, 1H).

Step 4: 2-(3,5-difluoropyridin-2-yl)-2,2-difluoroethyl trifluoromethanesulfonate

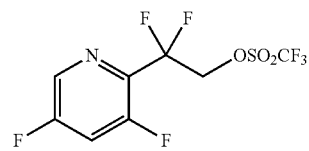

To the solution of 2-(3,5-difluoropyridin-2-yl)-2,2-difluoroethanol (485 mg, 2.49 mmol) and DIPEA (1.3 mL, 7.5 mmol) in anhydrous ether (25 mL) was added Tf$_2$O (0.84 mL, 4.98 mmol) slowly at 0° C. The reaction mixture was allowed to warm to rt. After 15 min at r.t., the suspension was filtered through celite and the solid was washed with ether. The filtrate was concentrated to afford the crude title compound as pale yellow oil (1.1 g, 100%) which was used directly without further purification.

Step 5: tert-butyl (1-(2-(3,5-difluoropyridin-2-yl)-2,2-difluoroethyl)piperidin-4-yl)-carbamate

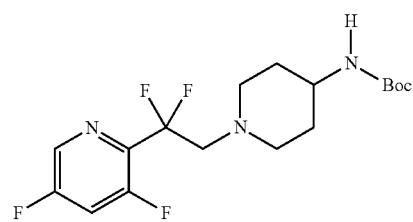 [SMILES: CC(C)(C)OC(=O)NC1CCN(CC(F)(F)c2ncc(F)cc2F)CC1]

A mixture of 2-(3,5-difluoropyridin-2-yl)-2,2-difluoroethyl trifluoromethanesulfonate (1.1 g, 2.72 mmol), tert-butyl piperidin-4-ylcarbamate (1.09 g, 5.44 mmol) and DIPEA (1.43 mL, 8.16 mmol) in DCM (15 mL) was heated to 40° C. After stirring overnight at 40° C., the mixture was concentrated and extracted with EtOAc. The organic layer was washed with water and brine, dried and concentrated. The concentrate was purified by column chromatography over silica gel (hexane/EtOAc=10:1) to afford the title compound as a white solid (754 mg, 74%). MS (ESI) calcd for $C_{17}H_{23}F_4N_3O_2$: 377.2; found: 378.3[M+H]. $^1$H NMR (400 MHz, CDCl$_3$) δ 8.36 (d, J=2.2 Hz, 1H), 7.29 (m, 1H), 4.34 (s, 1H), 3.39 (s, 1H), 3.19 (t, J=14.4 Hz, 2H), 2.88-2.82 (m, 2H), 2.44-2.33 (m, 2H), 1.82-1.75 (m, 2H), 1.43 (s, 9H), 1.33-1.20 (m, 2H).

Step 6: 1-(2-(3,5-difluoropyridin-2-yl)-2,2-difluoroethyl)piperidin-4-amine

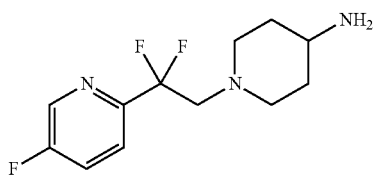 [SMILES: NC1CCN(CC(F)(F)c2ccc(F)cn2)CC1]

To the solution of tert-butyl (1-(2-(3,5-difluoropyridin-2-yl)-2,2-difluoroethyl)piperidin-4-yl)carbamate (750 mg, 1.99 mmol) in DCM (10 mL) was added TFA (5 mL) under ice-water bath cooling. After stirring for 15 min at r.t., the mixture was concentrated. The concentrate was basified with 1N NaOH, and extracted with EtOAc. The organic phase was washed with brine, dried over Na$_2$SO$_4$, and concentrated to afford the title compound as a pale yellow oil (514 mg, 93%) which was used directly without further purification. MS (ESI) calcd for $C_{12}H_{15}F_4N_3$: 277.1; found: 278.3[M+H]. $^1$H NMR (400 MHz, CDCl$_3$) δ 8.36 (s, 1H), 7.35-7.26 (m, 1H), 3.19 (t, J=14.4 Hz, 2H), 2.88-2.82 (m, 2H), 2.64-2.58 (m, 1H), 2.36-2.28 (m, 2H), 1.68-1.62 (m, 2H), 1.28-1.18 (m, 2H).

Step 7: N-(1-(2-(3,5-difluoropyridin-2-yl)-2,2-difluoroethyl)piperidin-4-yl)-1H-pyrazolo[3,4-d]-pyrimidin-4-amine

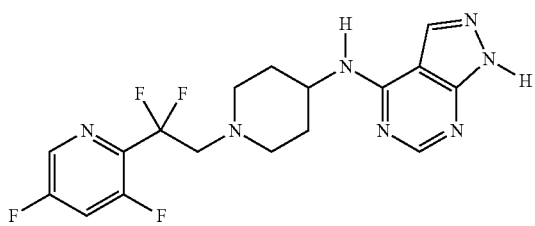 [SMILES: Fc1cnc(C(F)(F)CN2CCC(Nc3ncnc4[nH]ncc34)CC2)c(F)c1]

A mixture of 1-(2-(3,5-difluoropyridin-2-yl)-2,2-difluoroethyl)piperidin-4-amine (150 mg, 0.54 mmol), 4-chloro-1H-pyrazolo[3,4-d]pyrimidine (84 mg, 0.54 mmol) and DIPEA (0.19 mL, 1.1 mmol) in i-PrOH (3 mL) was heated to 85° C. After stirring overnight at 85° C., the reaction solution was concentrated and extracted with EtOAc. The organic layers were washed with water and brine, dried and concentrated. The concentrate was purified by column chromatography over silica gel (hexane/EtOAc=1/3) to afford the title compound as a white solid (110 mg, 52%). MS (ESI) calcd for $C_{17}H_{17}F_4N_7$: 395.2; found: 396.2[M+H]. $^1$H NMR (400 MHz, CD$_3$OD) δ 8.47 (d, J=2.2 Hz, 1H), 8.22 (s, 1H), 8.10 (s, 1H), 7.79-7.73 (m, 1H), 4.10 (brs, 1H), 3.28 (t, J=13.6 Hz, 2H), 3.05-2.98 (m, 2H), 2.54-2.48 (m, 2H), 1.98-1.92 (m, 2H), 1.60-1.50 (m, 2H).

Example 1.15a (HCl salt)

N-(1-(2-(3,5-difluoropyridin-2-yl)-2,2-difluoroethyl)piperidin-4-yl)-1H-pyrazolo[3,4-d]-pyrimidin-4-amine hydrochloride (C-15.HCl)

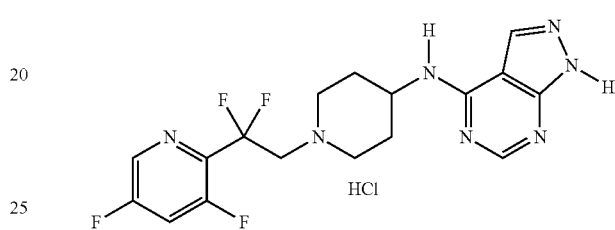

To the solution of N-(1-(2-(3,5-difluoropyridin-2-yl)-2,2-difluoroethyl)piperidin-4-yl)-1H-pyrazolo[3,4-d]-pyrimidin-4-amine (48.7 mg, 0.123 mmol) in MeOH (2 mL) was added HCl/MeOH (2M, 62 µL, 0.124 mmol) at rt. After stirring for 10 min, the mixture was concentrated to afford the title compound as white solid (55.2 mg, 100%). MS (ESI) calcd for $C_{17}H_{17}F_4N_7$: 395.2; found: 396.2[M+H]. $^1$H NMR (400 MHz, CD$_3$OD) δ 8.52 (s, 1H), 8.41 (s, 2H), 7.92-7.85 (m, 1H), 4.45-4.36 (m, 1H), 4.05-3.96 (m, 2H), 3.62-3.56 (m, 2H), 3.18-3.12 (m, 2H), 2.28-2.22 (m, 2H), 1.98-1.92 (m, 2H).

Example 1.16

N-(1-(2-(5-chloro-3-fluoropyridin-2-yl)-2,2-difluoroethyl)piperidin-4-yl)-1H-pyrazolo[3,4-d]pyrimidin-4-amine (C-16)

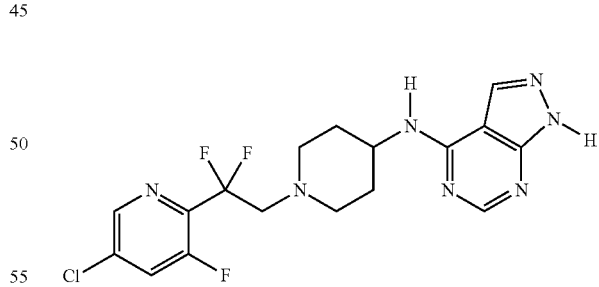

Step 1: 2-bromo-5-chloro-3-fluoropyridine

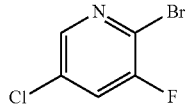

5-chloro-3-fluoropyridin-2-amine (5.0 g, 34 mmol) was slowly added to 48% HBr solution (20 mL) with stirring at 0° C. To the resulting mixture Br$_2$ (5.24 mL, 102.3 mmol) was then added over 20 minutes at 0° C. The reaction mixture was cooled to −10° C. A solution of NaNO$_2$ (5.88 g, 85.3 mmol) in water (20 mL) was added over 1.5 hours, and the mixture stirred for additional 30 minutes. A solution of NaOH (12 g, 306 mmol) in water (20 mL) was added over 30 minutes. and the mixture was allowed to warm to room temperature. The mixture was extracted with ether (3×100 mL). The combined organic phases were washed with brine, dried over sodium sulfate, filtered, and concentrated to afford the title compound as pale yellow solid (6.43 g, 90%). $^1$H NMR (400 MHz, CDCl$_3$) δ 8.23 (d, J=2.1 Hz, 1H), 7.48 (dd, J=7.1, 2.1 Hz, 1H).

Step 2: ethyl 2-(5-chloro-3-fluoropyridin-2-yl)-2,2-difluoroacetate

To the solution of 2-bromo-5-chloro-3-fluoropyridine (2.0 g, 9.5 mmol) and ethyl 2-bromo-2,2-difluoroacetate (1.93 g, 9.5 mmol) in DMSO (40 mL) was added Cu powder (1.21 g, 19 mmol). The mixture was heated to 80° C. for 20 hours and poured into a solution of dibasic potassium hydrogen phosphate trihydrate (21 g, 95 mmol) in water (200 mL) with vigorous stirring. The reaction mixture was filtered through celite and the solid cake was washed with ethyl acetate. The filtrate was extracted with ethyl acetate. The ethyl acetate layers were combined, dried over sodium sulfate, filtered, and concentrated. The concentrate was purified by column chromatography over silica gel (hexane/ethyl acetate=50:1) to afford the title compound as a colorless liquid (2.08 g, 86%). MS (ESI) calcd for C$_9$H$_7$ClF$_3$NO$_2$: 253.0; found: 254.2[M+H]. $^1$H NMR (400 MHz, CDCl$_3$) δ 8.42 (d, J=1.8 Hz, 1H), 7.61 (dd, J=9.4, 1.8 Hz, 1H), 4.46-4.39 (q, J=7.1 Hz, 2H), 1.37 (t, J=7.1 Hz, 3H).

Step 3: 2-(5-chloro-3-fluoropyridin-2-yl)-2,2-difluoroethanol

To the solution of ethyl 2-(5-chloro-3-fluoropyridin-2-yl)-2,2-difluoroacetate (2.1 g, 8.2 mmol) in ethanol (40 mL) was added NaBH$_4$ (341 mg, 9.02 mmol) slowly at 0° C. The mixture was stirred for 1 hour at room temperature. The stirred reaction mixture was cooled, quenched with 1N HCl, concentrated and extracted with ethyl acetate. The ethyl acetate layer was washed with water and brine, dried over sodium sulfate and concentrated to afford the title compound as a white solid (1.72 g, 99%). MS (ESI) calcd for C$_7$H$_5$ClF$_3$NO: 211.0; found: 212.2[M+H]. $^1$H NMR (400 MHz, CDCl$_3$) δ 8.40 (d, J=1.3 Hz, 1H), 7.63 (dd, J=9.5, 1.3 Hz, 1H), 4.26 (m, 2H).

Step 4: 2-(5-chloro-3-fluoropyridin-2-yl)-2,2-difluoroethyl trifluoromethanesulfonate

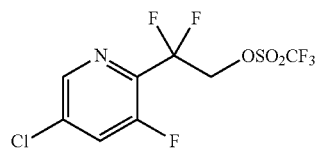

To the solution of 2-(5-chloro-3-fluoropyridin-2-yl)-2,2-difluoroethanol (1.0 g, 4.7 mmol) and DIPEA (2.5 mL, 14 mmol) in anhydrous ether (45 mL) was added Tf$_2$O (1.6 mL, 9.5 mmol) slowly at 0° C. The reaction mixture was allowed to warm to rt and stirred for 1 h. The orange suspension was filtered through celite, and the solid was washed with ether. The filtrate was concentrated to afford the crude title compound as pale yellow oil (1.65 g, 100%). The compound was used directly in the next step without further purification.

Step 5: tert-butyl 1-(2-(5-chloro-3-fluoropyridin-2-yl)-2,2-difluoroethyl)piperidin-4-ylcarbamate

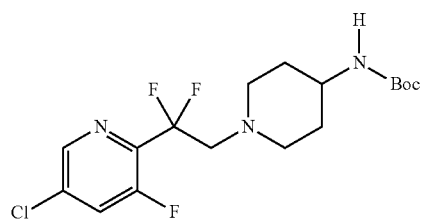 [SMILES: CC(C)(C)OC(=O)NC1CCN(CC(F)(F)c2ncc(Cl)cc2F)CC1]

A mixture of 2-(5-chloro-3-fluoropyridin-2-yl)-2,2-difluoroethyl trifluoromethane-sulfonate (1.65 g, 4.7 mmol), tert-butyl piperidin-4-ylcarbamate (1.92 g, 9.6 mmol) and DIPEA (2.5 mL, 14 mmol) in DCM (25 mL) was heated to 40° C. After stirring overnight at 40° C., the mixture was concentrated and extracted with EtOAc. The organic layer was washed with water and brine, dried and concentrated. The concentrate was purified by column chromatography over silica gel (hexane/EtOAc=10:1) to afford the title compound as pale yellow solid (1.64 g, 87%). MS (ESI) calcd for C$_{17}$H$_{23}$ClF$_3$N$_3$O$_2$: 393.1; found: 394.2[M+H]. $^1$H NMR (400 MHz, CDCl$_3$) δ 8.43 (s, 1H), 7.54 (dd, J=9.8, 1.8 Hz, 1H), 4.34 (s, 1H), 3.38 (s, 1H), 3.18 (t, 2H), 2.91-2.80 (m, 2H), 2.42-2.35 (m, 2H), 1.85-1.75 (m, 2H), 1.31-1.22 (m, 2H).

Step 6: 1-(2-(5-chloro-3-fluoropyridin-2-yl)-2,2-difluoroethyl)piperidin-4-amine

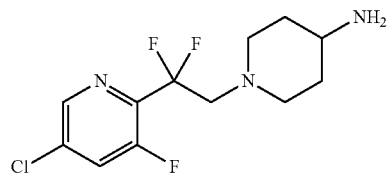 [SMILES: NC1CCN(CC(F)(F)c2ncc(Cl)cc2F)CC1]

To the solution of tert-butyl 1-(2-(5-chloro-3-fluoropyridin-2-yl)-2,2-difluoroethyl)piperidin-4-ylcarbamate (1.64 g, 4.16 mmol) in DCM (20 mL) was added TFA (10 mL) at 0° C. After stirring for 15 min at r.t., the mixture was concentrated. The concentrate was basified with 1N NaOH, and extracted with EtOAc. The organic phase was washed with brine, dried over $Na_2SO_4$, and concentrated to afford the crude title compound as pale yellow oil (1.43 g, 100%) which was used directly in the next step without further purification. MS (ESI) calcd for $C_{12}H_{15}ClF_3N_3$: 293.1; found: 294.2[M+H]. $^1$H NMR (400 MHz, $CDCl_3$) δ 8.43 (s, 1H), 7.54 (dd, J=9.8, 1.7 Hz, 1H), 3.18 (t, J=14.4 Hz, 2H), 2.88-2.84 (m, 2H), 2.66-2.54 (m, 1H), 2.36-2.28 (m, 2H), 1.70-1.64 (m, 2H), 1.29-1.15 (m, 2H).

Step 7: N-(1-(2-(5-chloro-3-fluoropyridin-2-yl)-2,2-difluoroethyl)piperidin-4-yl)-1H-pyrazolo[3,4-d]pyrimidin-4-amine

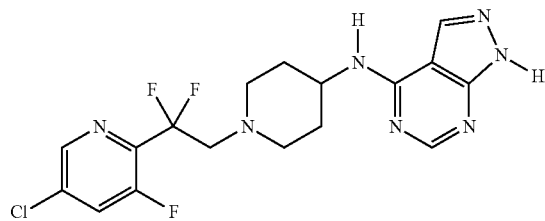 [SMILES: Fc1cc(Cl)cnc1C(F)(F)CN1CCC(Nc2ncnc3[nH]ncc23)CC1]

A mixture of 1-(2-(5-chloro-3-fluoropyridin-2-yl)-2,2-difluoroethyl)piperidin-4-amine (200 mg, 0.68 mmol), 4-chloro-1H-pyrazolo[3,4-d]pyrimidine (88 mg, 0.57 mmol) and DIPEA (0.2 mL, 1.1 mmol) in i-PrOH (3 mL) was heated to 85° C. After stirring overnight at 85° C., the reaction solution was concentrated and extracted with EtOAc. The organic layers were washed with water and brine, dried and concentrated. The concentrate was purified by column chromatography over silica gel (hexane/EtOAc=1/3) to afford the title compound as white solid (96.5 mg, 35%). MS (ESI) calcd for $C_{17}H_{17}ClF_3N_7$: 411.1; found: 412.2[M+H]. $^1$H NMR (400 MHz, $CD_3OD$) δ 8.52 (d, J=1.8 Hz, 1H), 8.22 (s, 1H), 8.10 (s, 1H), 7.97 (dd, J=10.3, 1.8 Hz, 1H), 4.15-4.04 (m, 1H), 3.27 (t, J=14.4 Hz, 2H), 3.10-2.98 (m, 2H), 2.51-2.45 (m, 2H), 1.98-1.92 (m, 2H), 1.61-1.46 (m, 2H).

Example 1.16a (HCl salt)

N-(1-(2-(5-chloro-3-fluoropyridin-2-yl)-2,2-difluoroethyl)piperidin-4-yl)-1H-pyrazolo[3,4-d]pyrimidin-4-amine hydrochloride (C-16.HCl)

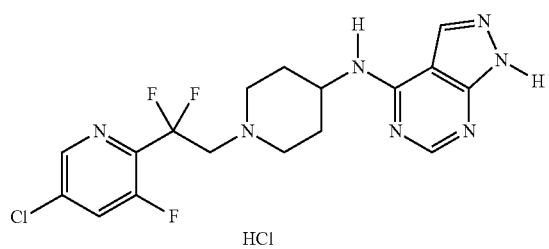 [SMILES: Fc1cc(Cl)cnc1C(F)(F)CN1CCC(Nc2ncnc3[nH]ncc23)CC1 ; Cl]

To the solution of N-(1-(2-(5-chloro-3-fluoropyridin-2-yl)-2,2-difluoroethyl)piperidin-4-yl)-1H-pyrazolo[3,4-d]pyrimidin-4-amine (96 mg, 0.23 mmol) in MeOH (1.5 mL) was added HCl/MeOH (2M, 0.12 mL, 0.23 mmol) at rt. After stirring for 10 min, the mixture was concentrated to afford the product as a white solid (104 mg, 100%). MS (ESI) calcd for $C_{17}H_7ClF_3N_7$: 411.1; found: 412.2[M+H]. $^1$H NMR (400 MHz, $CD_3OD$) δ 8.57 (s, 1H), 8.40 (s, 2H), 8.07 (d, J=10.2 Hz, 1H), 4.37 (s, 1H), 3.90 (s, 2H), 3.50 (s, 2H), 3.11 (m, 2H), 2.20 (d, J=8.3 Hz, 2H), 1.88 (m, 2H).

Example 1.17

N-(1-(2,2-difluoro-2-(3-fluoro-5-methylpyridin-2-yl)ethyl)piperidin-4-yl)-1H-pyrazolo[3,4-d]pyrimidin-4-amine (C-17)

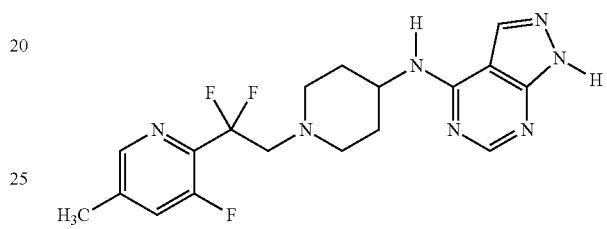

Step 1: ethyl 2,2-difluoro-2-(3-fluoro-5-methylpyridin-2-yl)acetate

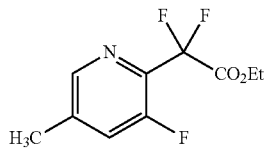

To a solution of 2-bromo-3-fluoro-5-methylpyridine (1.8 g, 9.5 mmol) and ethyl 2-bromo-2,2-difluoroacetate (1.8 mL, 14.2 mmol) in DMSO (30 mL) was added copper powder (1.2 g, 18.9 mmol). After stirring overnight to 50° C., the mixture was diluted with EtOAc. The mixture was poured into water, and stirred for 30 min. The suspension was filtered through a pad of Ceilite. The organic phase was washed with water and brine, dried over $Na_2SO_4$ and concentrated. The concentrate was purified by column chromatography over silica gel (hexane) to afford the title compound as white solid (1.6 g, 70%). $^1$H NMR (400 MHz, $CDCl_3$) δ 8.26 (s, 1H), 7.36 (d, J=10.6 Hz, 1H), 4.42 (q, J=7.1 Hz, 2H), 2.42 (s, 3H), 1.36 (t, J=7.1 Hz, 3H).

Step 2: 2,2-difluoro-2-(3-fluoro-5-methylpyridin-2-yl)ethanol

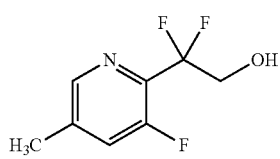

To a solution of ethyl 2,2-difluoro-2-(3-fluoro-5-methyl-pyridin-2-yl)acetate (1.68 g, 7.22 mmol) in ethanol (30 mL) was added the NaBH$_4$ (410 mg, 10.8 mmol) at room temperature. The solid NaBH$_4$ was gradually dissolved to form a clear solution. After stirred for 30 min, the reaction mixture was quenched with aqueous 1N HCl at 0° C. The mixture was extracted with EtOAc. The combined organic phases were washed with brine, dried over Na$_2$SO$_4$ and concentrated to afford the product as white powder (1.3 g, 100%). $^1$H NMR (400 MHz, CDCl$_3$) δ 8.22 (s, 1H), 7.39 (d, J=10.8 Hz, 1H), 4.32-4.20 (m, 2H), 3.45-3.35 (m, 1H), 2.43 (s, 3H).

Step 3: 2,2-difluoro-2-(3-fluoro-5-methylpyridin-2-yl)ethyl trifluoromethanesulfonate

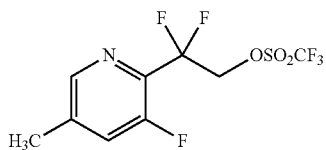

To a solution of 2,2-difluoro-2-(3-fluoro-5-methylpyridin-2-yl)ethanol (120 mg, 0.63 mmol) and DIPEA (0.15 mL, 0.95 mmol) in dried ether (5 mL) was added by dropwise Tf$_2$O (0.15 mL, 0.76 mmol) at 0° C. under N$_2$ atmosphere. After stirred for 1 h, the suspension was filtered, and the filtrate was concentrate to afford the crude title compound (200 mg) which was used directly without further purification in the next step.

Step 4: N-(1-(2,2-difluoro-2-(3-fluoro-5-methylpyridin-2-yl)ethyl)piperidin-4-yl)-1-(tetrahydro-2H-pyran-2-yl)-1H-pyrazolo[3,4-d]pyrimidin-4-amine

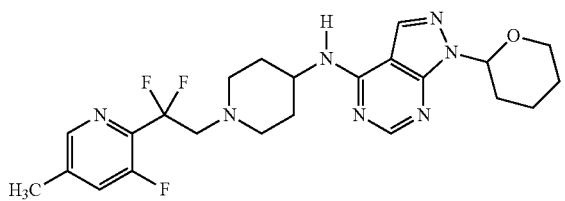 [SMILES: Cc1cnc(C(F)(F)CN2CCC(Nc3ncnc4c3cnn4C3CCCCO3)CC2)c(F)c1]

A mixture of 2,2-difluoro-2-(3-fluoro-5-methylpyridin-2-yl)ethyl trifluoromethane-sulfonate (200 mg, 0.62 mmol), N-(piperidin-4-yl)-1-(tetrahydro-2H-pyran-2-yl)-1H-pyrazolo[3,4-d]pyrimidin-4-amine (230 mg, 0.76 mmol) and DIPEA (0.20 mL, 1.25 mmol) in DCM (5 mL) was heated to 40° C. After stirring overnight, the solution was concentrated and purified by column chromatography over silica gel (100% EtOAc) to afford the title compound as a white powder (250 mg, 69%). MS (ESI) calcd for C$_{23}$H$_{28}$F$_3$N$_7$O: 475.2; found: 476.3 [M+H]. $^1$H NMR (400 MHz, CDCl$_3$) δ 8.37 (s, 1H), 8.28 (s, 1H), 7.90 (s, 1H), 7.30 (d, J=10.1 Hz, 1H), 5.94 (d, J=8.6 Hz, 1H), 4.15-4.07 (m, 1H), 3.83-3.75 (m, 1H), 3.71-3.61 (m, 2H), 3.25 (t, J=14.4 Hz, 2H), 3.10 (q, J=7.5 Hz, 1H), 3.03-2.94 (m, 2H), 2.58-2.48 (m, 3H), 2.41 (s, 3H), 2.03-1.88 (m, 3H), 1.82-1.70 (m, 2H), 1.62-1.52 (m, 2H).

Step 5: N-(1-(2,2-difluoro-2-(3-fluoro-5-methylpyridin-2-yl)ethyl)piperidin-4-yl)-1H-pyrazolo[3,4-d]pyrimidin-4-amine

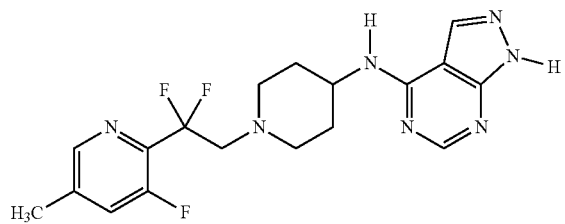 [SMILES: Cc1cnc(C(F)(F)CN2CCC(Nc3ncnc4[nH]ncc34)CC2)c(F)c1]

To a solution of N-(1-(2,2-difluoro-2-(3-fluoro-5-methylpyridin-2-yl)-ethyl)piperidin-4-yl)-1-(tetrahydro-2H-pyran-2-yl)-1H-pyrazolo[3,4-d]pyrimidin-4-amine (380 mg, 0.8 mmol) in 50% of DCM/MeOH (5 mL) was added the HCl solution in ether. The solution was quickly changed into white suspension. After stirred for 2 hrs at 30° C., the THP group was removed thoroughly. The suspension was concentrated, and partitioned into DCM and aqueous NaOH. The organic phase was washed with brine, dried over Na$_2$SO$_4$ and concentrated. The concentrated was washed with 30% of EtOAc in hexane to afford the free base as white powder (199 mg, 63%). MS (ESI) calcd for C$_{18}$H$_{20}$F$_3$N$_7$: 391.2; found: 392.2 [M+H]. $^1$H NMR (400 MHz, MeOD) δ 8.30 (s, 1H), 8.20 (s, 1H), 8.09 (s, 1H), 7.59 (d, J=11.7 Hz, 1H), 4.15-4.01 (m, 1H), 3.24 (t, J=14.4 Hz, 2H), 3.04-2.96 (m, 2H), 2.53-2.45 (m, 2H), 2.44 (s, 3H), 1.97-1.89 (m, 2H), 1.61-1.47 (m, 2H).

Example 1.17a (HCl salt)

N-(1-(2,2-difluoro-2-(3-fluoro-5-methylpyridin-2-yl)ethyl)piperidin-4-yl)-1H-pyrazolo[3,4-d]pyrimidin-4-amine hydrochloride (C-17.HCl)

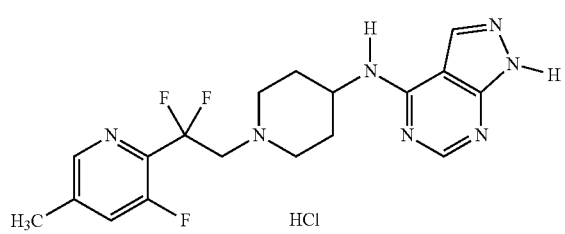 [SMILES: Cc1cnc(C(F)(F)CN2CCC(Nc3ncnc4[nH]ncc34)CC2)c(F)c1 ; Cl]

To a solution of N-(1-(2,2-difluoro-2-(3-fluoro-5-methyl-pyridin-2-yl)ethyl)-piperidin-4-yl)-1H-pyrazolo[3,4-d]pyrimidin-4-amine (198 mg, 0.50 mmol) in DCM/MeOH (1/1, 10 mL) was added 2.0M methanolic HCl (0.25 mL, 0.50 mmol). After stirring for 30 min, the solution was concentrated to afford the title compound as pale brown powder (215 mg, 100%). MS (ESI) calcd for C$_{18}$H$_{20}$F$_3$N$_7$: 391.2; found: 392.2 [M+H]. $^1$H NMR (400 MHz, MeOD) δ 8.46-8.26 (m, 3H), 7.68 (d, J=11.5 Hz, 1H), 4.51-4.36 (m, 1H), 4.17-3.97 (m, 2H), 3.73-3.59 (m, 2H), 3.28-3.17 (m, 2H), 2.47 (s, 3H), 2.33-2.21 (m, 2H), 2.07-1.91 (m, 2H).

Example 1.18

N-(1-(2,2-difluoro-2-(3-fluoro-5-(trifluoromethyl)pyridin-2-yl)-ethyl)piperidin-4-yl)-1H-pyrazolo[3,4-d]pyrimidin-4-amine (C-18)

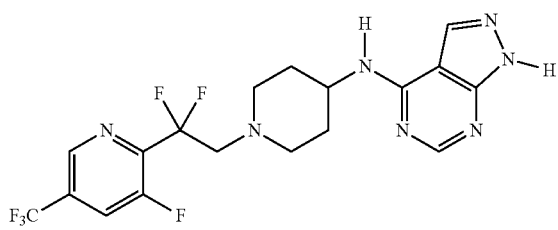 [SMILES: Fc1cc(C(F)(F)F)cnc1C(F)(F)CN1CCC(Nc2ncnc3[nH]ncc23)CC1]

Step 1: ethyl 2,2-difluoro-2-(3-fluoro-5-(trifluoromethyl)pyridin-2-yl)acetate

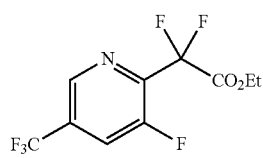

To the solution of ethyl 2-bromo-2,2-difluoroacetate (1.0 g, 4.8 mmol) and 2-bromo-3-fluoro-5-(trifluoromethyl)pyridine (1.1 g, 4.4 mmol) in DMSO (20 mL) was added Cu powder (568 mg, 8.8 mmol). The mixture was heated to 80° C. for 20 hours. The reaction mixture was filtered through celite and washed with ethyl acetate. The ethyl acetate layer was washed with brine, dried over sodium sulfate, filtered, and concentrated. The concentrate was purified by column chromatography over silica gel (hexane/ethyl acetate=100:1) to afford the title compound as a colorless oil (980 mg, 83%). $^1$H NMR (400 MHz, CDCl$_3$) δ 8.73 (s, 1H), 7.81 (d, J=9.6 Hz, 1H), 4.45 (q, J=7.2 Hz, 2H), 1.38 (t, J=7.2 Hz, 3H).

Step 2: 2,2-difluoro-2-(3-fluoro-5-(trifluoromethyl)pyridin-2-yl)ethanol

To the solution of 2,2-difluoro-2-(3-fluoro-5-(trifluoromethyl)pyridin-2-yl)acetate (980 mg, 3.41 mmol) in ethanol (20 mL) was added NaBH$_4$ (194 mg, 5.12 mmol) slowly at ice bath temperature and the mixture stirred for 30 min. The reaction mixture was quenched with 1N HCl, concentrated and extracted with ethyl acetate. The ethyl acetate layer was washed with water and brine, then dried and concentrated to afford the title compound as a white solid (780 mg, 93%). $^1$H NMR (400 MHz, CDCl$_3$) δ 8.72 (s, 1H), 7.84 (d, J=9.2 Hz, 1H), 4.30 (t, J=12.4 Hz, 2H), 2.86 (brs, 1H).

Step 3: 2,2-difluoro-2-(3-fluoro-5-(trifluoromethyl)pyridin-2-yl)ethyl trifluoromethane-sulfonate

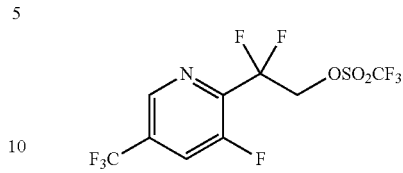

To the solution of 2,2-difluoro-2-(3-fluoro-5-(trifluoromethyl)pyridin-2-yl)ethanol (780 mg, 3.18 mmol) and DIPEA (1.6 mL, 9.6 mmol) in dried ether (15 ml) was added Tf$_2$O (0.9 mL, 6.36 mmol) at 0° C. After stirring for 1 hrs at rt, the white suspension was filtered through celite, and the filter mass was washed with ether. The filtrate was concentrated and purified by column chromatography over silica gel (hexane) to afford the title compound as a colorless oil (870 mg) which was used for the next step directly.

Step 4: tert-butyl 1-(2,2-difluoro-2-(3-fluoro-5-(trifluoromethyl)pyridin-2-yl)ethyl)-piperidin-4-ylcarbamate

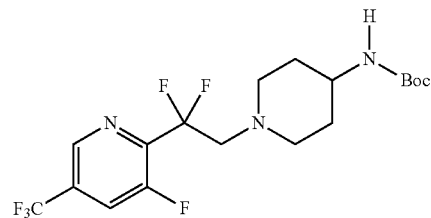

A mixture of 2,2-difluoro-2-(3-fluoro-5-(trifluoromethyl)pyridin-2-yl)ethyl trifluoro-methanesulfonate (870 mg), tert-butyl piperidin-4-ylmethylcarbamate (700 mg, 3.5 mmol) and DIPEA (1.06 ml, 6.38 mmol) in DCM (20 mL) was heated to 40° C. After stirring overnight at 40° C., the mixture was concentrated to dryness. The concentrate was purified by column chromatography over silica gel (hexane/ethyl acetate=10/1) to afford the title compound as a white solid (870 mg, 64%). $^1$H NMR (400 MHz, CDCl$_3$) δ 8.73 (s, 1H), 7.74 (d, J=10.0 Hz, 1H), 4.35 (s, 1H), 3.39 (s, 1H), 3.22 (t, J=14.0 Hz, 2H), 2.85-2.88 (m, 2H), 2.39 (t, J=10.0 Hz, 2H), 1.84-1.76 (m, 2H), 1.42 (s, 9H), 1.19-1.31 (m, 3H).

Step 5: 1-(2,2-difluoro-2-(3-fluoro-5-(trifluoromethyl)pyridin-2-yl)-ethyl)piperidin-4-amine

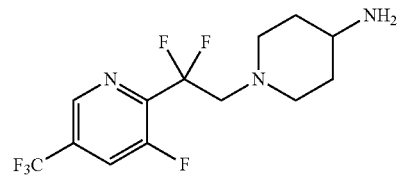 [SMILES: NC1CCN(CC(F)(F)c2ncc(C(F)(F)F)cc2F)CC1]

To a solution of tert-butyl 1-(2,2-difluoro-2-(3-fluoro-5-(trifluoromethyl)pyridin-2-yl)-ethyl)piperidin-4-ylcarbamate (870 mg, 2.03 mmol) in DCM (5 ml) was added TFA (5 ml) under ice-water bath. After stirred for 30 min at rt, the mixture was concentrated. The concentrate was basified with 1 N NaOH, and extracted with ethyl acetate. The organic phase was washed with brine, dried Na$_2$SO$_4$, and concentrated to afford the title compound as an off-white powder (600 mg, 100%). $^1$H NMR (400 MHz, CDCl$_3$) δ 8.72 (s, 1H), 7.76 (d, J=9.6 Hz, 1H), 6.40 (s, 2H), 3.24 (t, J=14.0 Hz, 2H), 2.98-2.95 (m, 3H), 2.35 (t, J=11.2 Hz, 2H), 1.86-1.80 (m, 2H), 1.49-1.41 (m, 2H).

Step 6: N-(1-(2,2-difluoro-2-(3-fluoro-5-(trifluoromethyl)pyridin-2-yl)-ethyl)piperidin-4-yl)-1H-pyrazolo[3,4-d]pyrimidin-4-amine

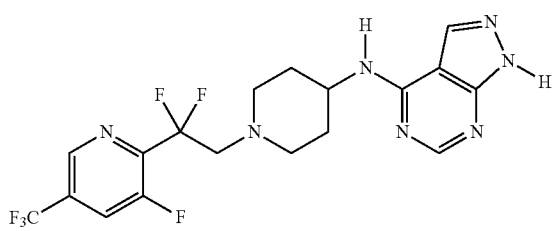 [SMILES: Fc1cc(C(F)(F)F)cnc1C(F)(F)CN1CCC(Nc2ncnc3[nH]ncc23)CC1]

A mixture of 1-(2,2-difluoro-2-(3-fluoro-5-(trifluoromethyl)pyridin-2-yl)ethyl)piperidin-4-amine (320 mg, 0.95 mmol), 4-chloro-1H-pyrazolo[3,4-d]pyrimidine (130 mg, 0.80 mmol) and DIPEA (0.3 mL, 1.7 mmol) in n-butyl alcohol (5 mL) was heated to 90° C. After stirring overnight at 90° C., the orange solution was concentrated. The concentrate was purified by column chromatography over silica gel (DCM/MeOH=30:1) to afford the title compound as a white powder (190 mg, 47%). MS (ESI) calcd for C$_{18}$H$_{17}$F$_6$N$_7$: 445.2; found: 446.7[M+H]. $^1$H NMR (400 MHz, CD$_3$OD) δ 8.84 (s, 1H), 8.21 (d, J=10.4 Hz, 1H), 8.19 (s, 1H), 8.08 (s, 1H), 4.11-4.05 (m, 1H), 3.38-3.35 (m, 2H), 3.05-2.95 (m, 2H), 2.52-2.45 (m, 2H), 1.95-1.88 (m, 2H), 1.45-1.53 (m, 2H).

Example 1.18a (HCl salt)

N-(1-(2,2-difluoro-2-(3-fluoro-5-(trifluoromethyl)pyridin-2-yl)-ethyl)-piperidin-4-yl)-1H-pyrazolo[3,4-d]pyrimidin-4-amine hydrochloride (C-18.HCl)

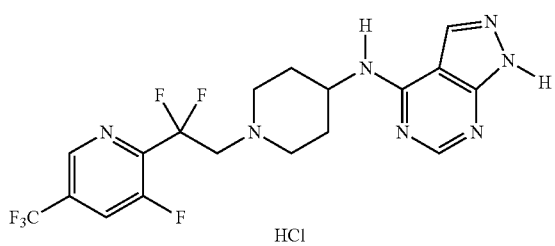 [SMILES: Fc1cc(C(F)(F)F)cnc1C(F)(F)CN1CCC(Nc2ncnc3[nH]ncc23)CC1 ; Cl]

To a solution of N-(1-(2,2-difluoro-2-(3-fluoro-5-(trifluoromethyl)pyridin-2-yl)-ethyl)piperidin-4-yl)-1H-pyrazolo[3,4-d]pyrimidin-4-amine (120 mg, 0.27 mmol) in MeOH (3.0 mL) was added HCl/MeOH (2M, 0.14 mL) at rt. After stirring for 15 min, the mixture was concentrated to afford the title compound as an off-white powder (127 mg, 98%). MS (ESI) calcd for C$_{18}$H$_{21}$ClF$_2$N$_6$: 445.2; found: 446.7[M+H]. $^1$H NMR (400 MHz, CD$_3$OD) δ 8.78 (s, 1H), 8.36 (brs, 1H), 8.35 (brs, 1H), 8.22 (d, J=10.0 Hz, 1H), 4.35-4.28 (m, 1H), 3.84-3.87 (m, 2H), 3.42-3.46 (m, 2H), 3.01-3.07 (m, 2H), 2.15-2.05 (m, 2H), 1.81-1.91 (m, 2H).

Example 1.24

N-(1-(2-(3,5-dichloropyridin-2-yl)-2,2-difluoroethyl)piperidin-4-yl)-1H-pyrazolo[3,4-d]pyrimidin-4-amine (C-24)

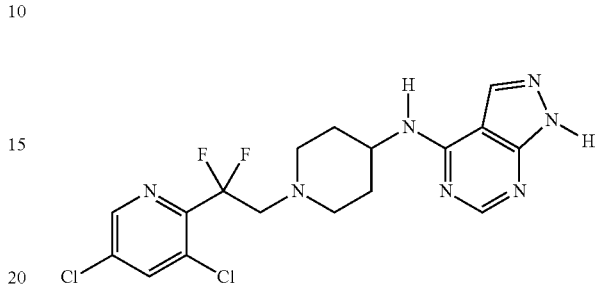

Step 1: 2-bromo-3,5-dichloropyridine

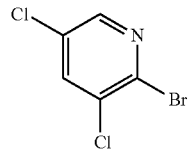

To a solution of 3,5-dichloropyridin-2-amine (1.0 g, 6.2 mmol) in 40% aqueous HBr (8 mL) was added dropwise bromine (2.8 g, 17 mmol) at −20° C. The orange suspension was stirred for 2 hrs at −20° C., and followed by addition of the aqueous NaNO$_2$ (1.1 g, 17 mmol) at −20° C. The mixture thus obtained was stirred for an additional 2 hours at ambient temperature. The brown mixture was basified with 30% aqueous NaOH to pH ~12 at 0° C. The pale yellow mixture was extracted with ether. The combined organic phases were washed with brine, dried over Na$_2$SO$_4$ and concentrated to afford the title compound as yellow solid (730 mg, 52%). $^1$H NMR (400 MHz, CDCl$_3$) δ 8.27 (d, J=2.3 Hz, 1H), 7.77 (d, J=2.3 Hz, 1H).

Step 2: ethyl 2-(3,5-dichloropyridin-2-yl)-2,2-difluoroacetate

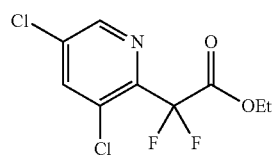 [SMILES: CCOC(=O)C(F)(F)c1ncc(Cl)cc1Cl]

To a solution of 2-bromo-3,5-dichloropyridine (450 mg, 2.0 mmol) and ethyl 2-bromo-2,2-difluoroacetate (0.40 mL, 1.5 mmol) in DMSO (10 mL) was added copper powder (250 mg, 4.0 mmol). The mixture thus obtained was heated to 90° C., and stirred overnight. The mixture was poured into water, and stirred for additional 1 h at room temperature. The final suspension was filtered through a pad of celite, and the filter mass was washed with EtOAc. The combined organic phases were washed with water and brine, dried over $Na_2SO_4$ and concentrated in vacuo to afford the crude title compound as a yellow oil (410 mg, 77%).

Step 3: 2-(3,5-dichloropyridin-2-yl)-2,2-difluoroethanol

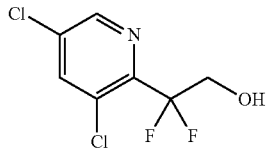 [SMILES: OCC(F)(F)c1ncc(Cl)cc1Cl]

To a solution of ethyl 2-(3,5-dichloropyridin-2-yl)-2,2-difluoroacetate (600 mg, 2.2 mmol) in ethanol (10 mL) was added $NaBH_4$ (130 mg, 3.3 mmol) at room temperature. After stirring for 30 min, the ester was consumed, and the mixture was quenched with aqueous 1M HCl at ice bath temperature. The mixture was basified with aqueous 1M NaOH, and extracted with EtOAc. The combined EtOAc phases were washed with brine, dried over $Na_2SO_4$ and concentrated in vacuo. The crude product was purified by column chromatography over silica gel (hexane/EtOAc=3/1) to afford the title compound as a white solid (250 mg, 50%). $^1$H NMR (400 MHz, $CDCl_3$) δ 8.44 (d, J=1.8 Hz, 1H), 7.90 (d, J=1.8 Hz, 1H), 4.33-4.22 (m, 2H), 3.01 (t, J=7.6 Hz, 1H).

Step 4: 2-(3,5-dichloropyridin-2-yl)-2,2-difluoroethyl trifluoromethanesulfonate

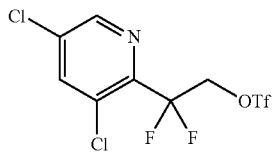 [SMILES: O=S(=O)(OCC(F)(F)c1ncc(Cl)cc1Cl)C(F)(F)F]

To a solution of 2-(3,5-dichloropyridin-2-yl)-2,2-difluoroethanol (250 mg, 1.1 mmol) and DIPEA (0.30 mL, 1.65 mmol) in dry ether (5 mL) was added the $Tf_2O$ (0.22 mL, 1.32 mmol) dropwise at 0° C. under nitrogen atmosphere. The pink suspension thus obtained was stirred for 2 hours at room temperature. After the alcohol was consumed, the suspension was filtered through a pad of celite. The filtrate was concentrated in vacuo, and purified by column chromatography over silica gel (hexane/EtOAc=4/1) to afford the title compound as a colorless oil (210 mg, 53%). $^1$H NMR (400 MHz, $CDCl_3$) δ 8.45 (d, J=1.8 Hz, 1H), 7.90 (d, J=1.8 Hz, 1H), 5.19 (t, J=12.1 Hz, 2H).

Step 5: N-(1-(2-(3,5-dichloropyridin-2-yl)-2,2-difluoroethyl)piperidin-4-yl)-1-(tetrahydro-2H-pyran-2-yl)-1H-pyrazolo[3,4-d]pyrimidin-4-amine

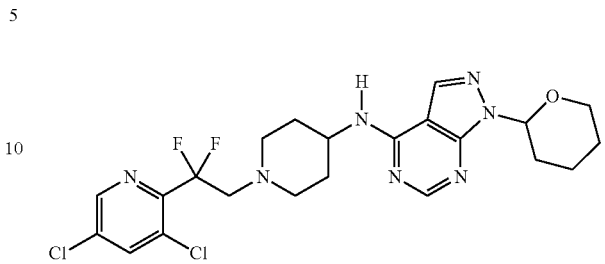

A solution of 2-(3,5-dichloropyridin-2-yl)-2,2-difluoroethyl trifluoromethanesulfonate (210 mg, 0.55 mmol), N-(piperidin-4-yl)-1-(tetrahydro-2H-pyran-2-yl)-1H-pyrazolo[3,4-d]pyrimidin-4-amine (185 mg, 0.61 mmol) and DIPEA (0.15 mL, 0.84 mmol) in DCM (5 mL) was heated to 40° C. After stirring overnight, the mixture was concentrated in vacuo and purified by column chromatography over silica gel (100% EtOAc) to afford the title compound as a white powder (185 mg, 65%). MS (ESI) calcd for $C_{22}H_{25}Cl_2F_2N_7O$: 511.2; found: 512.2 [M+H]. $^1$H NMR (400 MHz, $CDCl_3$) δ 8.50 (d, J=1.9 Hz, 1H), 8.38 (s, 1H), 7.88 (s, 1H), 7.83 (d, J=1.9 Hz, 1H), 5.95 (d, J=8.8 Hz, 1H), 4.22-3.97 (m, 2H), 3.85-3.72 (m, 1H), 3.33 (t, J=14.5 Hz, 2H), 3.07-2.94 (m, 2H), 2.62-2.48 (m, 3H), 2.10 (m, 1H) 2.05 (m, 2H), 1.89 (m, 1H), 1.83-1.70 (m, 2H), 1.59-1.43 (m, 2H), 1.30 (m, 2H).

Step 6: N-(1-(2-(3,5-dichloropyridin-2-yl)-2,2-difluoroethyl)piperidin-4-yl)-1H-pyrazolo[3,4-d]pyrimidin-4-amine

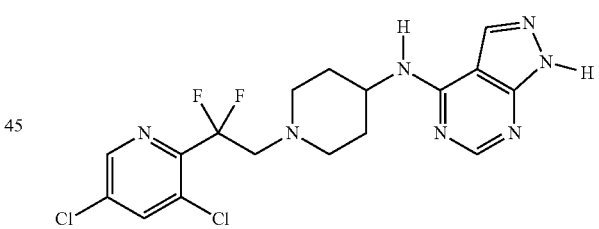

To a solution of N-(1-(2-(3,5-dichloropyridin-2-yl)-2,2-difluoroethyl)piperidin-4-yl)-1-(tetrahydro-2H-pyran-2-yl)-1H-pyrazolo[3,4-d]pyrimidin-4-amine (185 mg, 0.36 mmol) in DCM (5 mL) was added a saturated $HCl/Et_2O$ solution (5 mL). After stirring overnight at room temperature, the suspension was concentrated in vacuo, and basified with aqueous 1M NaOH. The basic aqueous mixture was extracted with DCM. The combined DCM phases were washed with brine, dried over $Na_2SO_4$ and concentrated in vacuo to give the title compound as a white powder (120 mg, 79%). MS (ESI) calcd for $C_{17}H_{17}Cl_2F_2N_7$: 427.1; found: 428.2 [M+H]. $^1$H NMR (400 MHz, $CD_3OD$) δ 8.48 (d, J=2.0 Hz, 1H), 8.10 (s, 1H), 8.05 (d, J=2.0 Hz, 1H), 7.99 (s, 1H), 4.04-3.92 (m, 1H), 3.31-3.22 (t, J=14.4 Hz, 2H), 2.97-2.90 (m, 2H), 2.45-2.31 (m, 2H), 1.87-1.79 (m, 2H), 1.50-1.36 (m, 2H).

Example 1.24a (HCl salt)

N-(1-(2-(3,5-dichloropyridin-2-yl)-2,2-difluoroethyl)piperidin-4-yl)-1H-pyrazolo[3,4-d]pyrimidin-4-amine hydrochloride (C-24 HCl)

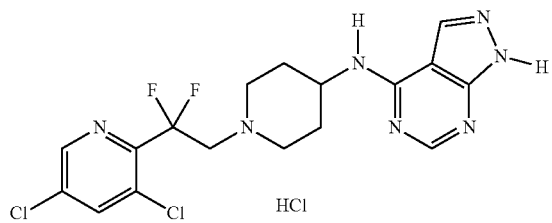 [SMILES: FC(F)(CN1CCC(Nc2ncnc3[nH]ncc23)CC1)c1ncc(Cl)cc1Cl ; Cl]

To a solution of N-(1-(2-(3,5-dichloropyridin-2-yl)-2,2-difluoroethyl)piperidin-4-yl)-1H-pyrazolo[3,4-d]pyrimidin-4-amine (87 mg, 0.20 mmol) in MeOH (5 mL) was added a methanolic solution of HCl (0.1 mL, 2.0 M, 0.20 mmol). After stirring for 30 min, the solution was concentrated to afford the title compound white powder (92 mg, 98%). MS (ESI) calcd for $C_{17}H_7Cl_2F_2N_7$: 427.1; found: 428.2 [M+H]. $^1$H NMR (400 MHz, $CD_3OD$) δ 8.66 (d, J=1.9 Hz, 1H), 8.50-8.37 (m, 2H), 8.30 (d, J=1.9 Hz, 1H), 4.55-4.40 (m, 1H), 4.28-4.09 (m, 2H), 3.82-3.66 (m, 2H), 3.32-3.22 (m, 2H), 2.37-2.24 (m, 2H), 2.12-1.96 (m, 2H).

Example 1.33

N-(1-(2,2-difluoro-2-(5-(trifluoromethyl)pyridin-2-yl)ethyl)piperidin-4-yl)-3-methyl-1H-pyrazolo[3,4-d]pyrimidin-4-amine (C-33)

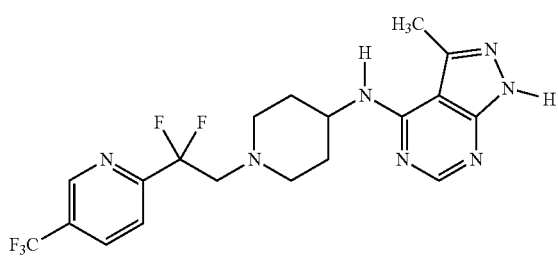 [SMILES: Cc1n[nH]c2ncnc(NC3CCN(CC(F)(F)c4ccc(C(F)(F)F)cn4)CC3)c12]

A mixture of 1-(2,2-difluoro-2-(5-(trifluoromethyl)pyridin-2-yl)ethyl)piperidin-4-amine (130 mg, 0.42 mmol), 4-chloro-3-methyl-1H-pyrazolo[3,4-d]pyrimidine (60 mg, 0.356 mmol) and DIPEA (0.14 ml, 0.84 mmol) in butyl alcohol (3 ml) was heated to 85° C. After stirring overnight at 85° C., the orange solution was concentrated. The concentrate was purified by column chromatography over silica gel (DCM/MeOH=30:1) to afford the title compound as white powder (98 mg, 62%). MS (ESI) calcd for $C_{19}H_{20}F_5N_7$: 441.2; found: 442.2[M+H]. $^1$H NMR (400 MHz, $CD_3OD$) δ 9.01 (s, 1H), 8.31 (d, J=8.4 Hz, 1H), 8.18 (s, 1H), 7.96 (d, J=8.4 Hz, 1H), 4.25-4.11 (m, 1H), 3.29-3.36 (m, 2H), 2.60 (s, 3H), 2.55-2.44 (m, 2H), 1.98-1.83 (m, 2H), 1.68-1.52 (m, 2H).

Example 1.33a (HCl salt)

N-(1-(2,2-difluoro-2-(5-(trifluoromethyl)pyridin-2-yl)ethyl)-piperidin-4-yl)-7H-pyrrolo[2,3-d]pyrimidin-4-amine hydrochloride (C-33.HCl)

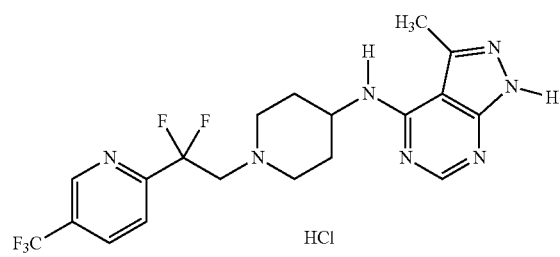 [SMILES: Cc1n[nH]c2ncnc(NC3CCN(CC(F)(F)c4ccc(C(F)(F)F)cn4)CC3)c12 ; Cl]

To a solution of N-(1-(2,2-difluoro-2-(5-(trifluoromethyl)pyridin-2-yl)ethyl)piperidin-4-yl)-3-methyl-1H-pyrazolo[3,4-d]pyrimidin-4-amine (83 mg, 0.188 mmol) in MeOH (3.0 ml) was added HCl/MeOH (2M, 0.094 ml, 0.188 mmol) at rt. After stirring for 15 min, the mixture was concentrated to afford the title compound as an off-white powder (89 mg, 100%). MS (ESI) calcd for $C_{19}H_{20}F_5N_7$: 441.2; found: 442.2[M+H]. $^1$H NMR (400 MHz, $CD_3OD$) δ 9.07 (s, 1H), 8.48-8.37 (m, 2H), 8.06 (d, J=8.3 Hz, 1H), 4.58 (m, 1H), 3.98 (m, 2H), 3.64-3.50 (m, 2H), 3.19-3.04 (m, 2H), 2.77 (s, 3H), 2.25-2.14 (m, 2H), 2.14-2.00 (m, 2H).

Example 1.127

N-(1-(2,2-difluoro-2-(6-(trifluoromethyl)pyridin-3-yl)ethyl)piperidin-4-yl)-1H-pyrazolo[3,4-d]pyrimidin-4-amine (C-127)

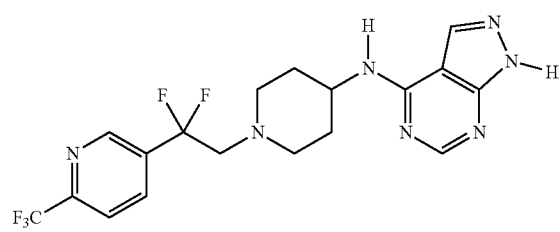 [SMILES: FC(F)(F)c1ccc(C(F)(F)CN2CCC(Nc3ncnc4[nH]ncc34)CC2)cn1]

Step 1: N-(1-(2,2-difluoro-2-(6-(trifluoromethyl)pyridin-3-yl)ethyl)piperidin-4-yl)-1-(tetrahydro-2H-pyran-2-yl)-1H-pyrazolo[3,4-d]pyrimidin-4-amine

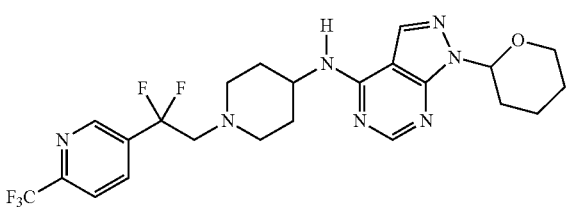 [SMILES: FC(F)(F)c1ccc(C(F)(F)CN2CCC(Nc3ncnc4c3cnn4C3CCCCO3)CC2)cn1]

The mixture of 1-(2,2-difluoro-2-(6-(trifluoromethyl)pyridin-3-yl)ethyl)piperidin-4-amine (309 mg, 1.0 mmol), 4-chloro-1-(tetrahydro-2H-pyran-2-yl)-1H-pyrazolo[4,3-c]

pyridine (200 mg, 0.84 mmol) and DIPEA (0.3 mL, 1.6 mmol) in i-PrOH was stirred at 85° C. overnight. The orange solution was concentrated. The concentrate was extracted with EtOAc and washed with water. The concentrate was purified by column chromatography over silica gel (hexane/ethyl acetate=4/1) to afford the title compound as a white solid (160 mg, 38%). MS (ESI) calcd for $C_{23}H_{26}F_5N_7$: 511.2; found: 512.5 [M+H]. $^1$H NMR (400 MHz, CDCl$_3$) δ 8.93 (s, 1H), 8.39 (s, 1H), 8.04 (d, J=8.1 Hz, 1H), 7.91 (s, 1H), 7.77 (d, J=8.1 Hz, 1H), 5.97-5.94 (m, 1H), 4.15-4.10 (m, 2H), 3.83-3.73 (m, 1H), 3.07 (t, J=12.8 Hz, 2H), 2.84-2.81 (m, 2H), 2.61-2.48 (m, 3H), 2.15-2.10 (m, 1H), 2.04-2.00 (m, 2H), 1.95-1.92 (m, 1H), 1.81-1.73 (m, 2H), 1.52-1.47 (m, 2H).

Step 2: N-(1-(2,2-difluoro-2-(6-(trifluoromethyl) pyridin-3-yl)ethyl)piperidin-4-yl)-1H-pyrazolo[3,4-d]pyrimidin-4-amine

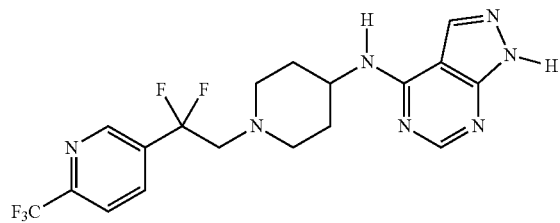

To a mixture of N-(1-(2,2-difluoro-2-(6-(trifluoromethyl) pyridin-3-yl)ethyl)piperidin-4-yl)-1-(tetrahydro-2H-pyran-2-yl)-1H-pyrazolo[3,4-d]pyrimidin-4-amine(160 mg, 0.31 mmol) in MeOH (2.6 mL) was added HCl/Et$_2$O (2M, 2.6 mL, 0.31 mmol) at rt. After stirring for 4 h, the mixture was concentrated and a solution of 1N NaOH was added. The mixture was extracted with EtOAc and washed with water. The organic layer was dried and concentrated to give the title compound as a white solid (130 mg, 98%). MS (ESI) calcd for $C_{18}H_{18}F_5N_7$: 427.15; found: 428.4 [M+H]. $^1$H NMR (400 MHz, CDCl$_3$) δ 12.75 (brs, 1H), 8.94 (s, 1H), 8.44 (s, 1H), 8.05 (d, J=8.1 Hz, 1H), 7.96 (s, 1H), 7.78 (d, J=8.1 Hz, 1H), 5.34 (brs, 1H), 4.13-4.10 (m, 1H), 3.05 (t, J=13.2 Hz, 2H), 2.86-2.83 (m, 2H), 2.57-2.52 (m, 2H), 2.07-2.05 (m, 2H), 1.84-1.78 (m, 1H), 1.30-1.18 (m, 2H).

Example 1.127a (HCl salt)

N-(1-(2,2-difluoro-2-(6-(trifluoromethyl)pyridin-3-yl)ethyl)piperidin-4-yl)-1H-pyrazolo[3,4-d]pyrimidin-4-amine hydrochloride (C-127.HCl)

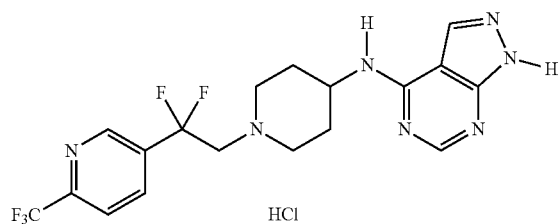

To the solution of N-(1-(2,2-difluoro-2-(6-(trifluoromethyl)pyridin-3-yl)ethyl)piperidin-4-yl)-1H-pyrazolo[3,4-d] pyrimidin-4-amine (130 mg, 0.3 mmol) in MeOH (1.5 mL) was added HCl/Et$_2$O (2M, 0.15 mL, 0.30 mmol). After stirring for 15 min, the mixture was concentrated to afford the title compound as an off-white powder (140 mg, 96%). MS (ESI) calcd for $C_{18}H_{18}F_5N_7$:427.2; found: 428.4 [M+H]. $^1$H NMR (400 MHz, CD$_3$OD) δ 9.01 (s, 1H), 8.58-8.51 (m, 2H), 8.33 (d, J=8.0 Hz, 1H), 8.02 (d, J=8.0 Hz, 1H), 4.46 (s, 1H), 3.72-3.68 (m, 2H), 3.44 (s, 1H), 3.37 (s, 1H), 3.08-2.95 (m, 2H), 2.21-2.18 (m, 2H), 2.00-1.90 (m, 2H).

Example 1.142

N-(1-(2,2-difluoro-2-(6-(trifluoromethyl)pyridin-3-yl)ethyl)piperidin-4-yl)-3-methyl-1H-pyrazolo[3,4-d]pyrimidin-4-amine (C-142)

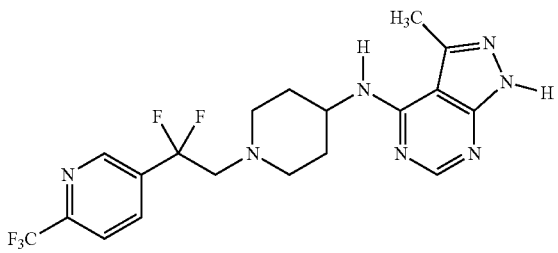 [SMILES: Cc1n[nH]c2ncnc(NC3CCN(CC(F)(F)c4ccc(C(F)(F)F)nc4)CC3)c12]

Step 1: 5-iodo-2-(trifluoromethyl)pyridine

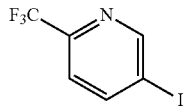

A solution of 6-(trifluoromethyl)pyridin-3-amine (9.96 g, 0.062 mol) in 5N HCl (70 mL) was cooled to −5° C. and sodium nitrite (6.39 g, 0.093 mol) in 30 mL of water was added dropwise while maintaining the internal temperature below 5° C. After 10 min, KI (22.5 g, 0.136 mol) in 30 mL of water was added dropwise at −5° C. while maintaining the internal temperature below 10° C. over the course of the addition. The reaction mixture was warmed to rt and 250 mL of EtOAc was added. The pH of the aqueous layer was adjusted to 11 by the addition of 50 mL of 6N NaOH, the layers were separated, and the organic layer was washed with 120 mL of 0.3M Na$_2$S$_2$O$_3$. The EtOAc layer was concentrated and the concentrate was purified by column chromatography over silica gel (hexane/EtOAc=25/1) to afford the title compound as a white solid (14.6 g, 87%). MS (ESI) calcd for $C_6H_3F_3IN$: 273.0; found: 274.0[M+H]. $^1$H NMR (400 MHz, CDCl$_3$) δ 8.96 (s, 1H), 8.22 (d, J=8.2 Hz, 1H), 7.47 (d, J=8.2 Hz, 1H).

Step 2: ethyl 2,2-difluoro-2-(6-(trifluoromethyl)pyridin-3-yl)acetate

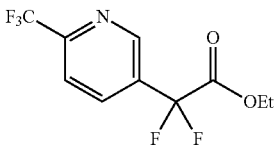 [SMILES: CCOC(=O)C(F)(F)c1ccc(C(F)(F)F)nc1]

To a solution of 5-iodo-2-(trifluoromethyl)pyridine (14.5 g, 53.2 mmol) and ethyl 2-bromo-2,2-difluoroacetate (10.8 g, 53.2 mmol) in DMF (250 mL) was added Cu powder (6.76 g, 106.4 mmol). The mixture was heated to 80° C. for 20 hours. After 20 hours, the reaction mixture was poured into a solution of dibasic potassium hydrogen phosphate, trihydrate (121 g, 532 mmol) in water (1500 mL) with vigorous stirring. The suspension was filtered and the solid was rinsed with ether. The filtrate was added to brine and extracted with ether (2×). The combined organics were washed with brine, dried over sodium sulfate, filtered, and concentrated. The concentrate was purified by column chromatography over silica gel (hexane/EtOAc=50:1) to afford the title compound as a colorless liquid (8.96 g, 63%). MS (ESI) calcd for $C_{10}H_8F_5NO_2$: 269.2; found: 270.3[M+H]. $^1$H NMR (400 MHz, CDCl$_3$) δ 8.98 (s, 1H), 8.14 (d, J=8.2 Hz, 1H), 7.81 (d, J=8.2 Hz, 1H), 4.35 (q, J=7.1 Hz, 2H), 1.34 (t, J=7.1 Hz, 3H).

Step 3: 2,2-difluoro-2-(6-(trifluoromethyl)pyridin-3-yl)ethanol

To the solution of ethyl 2,2-difluoro-2-(6-(trifluoromethyl)pyridin-3-yl)acetate (8.86 g, 32.9 mmol) in ethanol (165 mL) was added NaBH$_4$ (1.79 g, 47.4 mmol) slowly at rt. The mixture was stirred for 30 min at rt. After 30 min, the reaction mixture was quenched with 1N HCl at ice-water bath temperature. The mixture was concentrated and extracted with EtOAc. The EtOAc layer was washed with water and brine, then dried and concentrated to afford the title compound as a white solid (6.13 g, 82%). MS (ESI) calcd for $C_8H_6F_5NO$: 227.0; found: 228.2[M+H]. $^1$H NMR (400 MHz, CDCl$_3$) δ 8.91 (s, 1H), 8.06 (d, J=8.2 Hz, 1H), 7.79 (d, J=8.2 Hz, 1H), 4.06 (td, J=12.4, 7.0 Hz, 2H), 2.16 (t, J=7.0 Hz, 1H).

Step 4: 2,2-difluoro-2-(6-(trifluoromethyl)pyridin-3-yl)ethyl trifluoromethanesulfonate

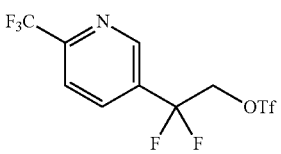 [SMILES: O=S(=O)(OCC(F)(F)c1ccc(C(F)(F)F)nc1)C(F)(F)F]

To the solution of 2,2-difluoro-2-(6-(trifluoromethyl)pyridin-3-yl)ethanol (1.0 g, 4.4 mmol) and DIPEA (2.39 ml, 13.2 mmol) in dry ether (44 ml) was added Tf$_2$O (1.48 ml, 8.8 mmol) at 0° C. After stirring for 1 hr at rt, the orange suspension was filtered by through celite, and the filter mass was washed with ether. The filtrate was concentrated, and purified by column chromatography to afford the title compound as pale yellow solid (1.47 g, 93%). $^1$H NMR (400 MHz, CDCl$_3$) δ 8.92 (s, 1H), 8.07 (d, J=8.2 Hz, 1H), 7.86 (d, J=8.2 Hz, 1H), 4.78 (t, J=11.2 Hz, 2H).

Step 5: tert-butyl 1-(2,2-difluoro-2-(6-(trifluoromethyl)pyridin-3-yl)ethyl)piperidin-4-yl-carbamate

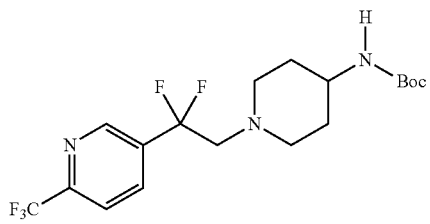 [SMILES: CC(C)(C)OC(=O)NC1CCN(CC(F)(F)c2ccc(C(F)(F)F)nc2)CC1]

The mixture of 2,2-difluoro-2-(6-(trifluoromethyl)pyridin-3-yl)ethyl trifluoromethane-sulfonate (1.46 g, 4.07 mmol), tert-butyl piperidin-4-ylcarbamate (1.63 g, 8.13 mmol) and DIPEA (2.2 ml, 12.2 mmol) in DCM (20 ml) was heated to 40° C. After stirring overnight at 40° C., the mixture was concentrated to dryness. The concentrate was purified by column chromatography over silica gel (hexane/EtOAc=10/1) to afford the title compound as a white solid (1.37 g, 83%). MS (ESI) calcd for $C_{18}H_{24}F_5N_3O_2$: 409.2; found: 410.4[M+H]. $^1$H NMR (400 MHz, CDCl$_3$) δ 8.89 (s, 1H), 8.01 (d, J=8.2 Hz, 1H), 7.75 (d, J=8.2 Hz, 1H), 4.37 (s, 1H), 3.40 (s, 1H), 2.97 (t, J=13.2 Hz, 2H), 2.72 (m, 2H), 2.38 (m, 2H), 1.83 (m, 2H), 1.43 (s, 9H), 1.36-1.23 (m, 2H).

Step 6: 1-(2,2-difluoro-2-(6-(trifluoromethyl)pyridin-3-yl)ethyl)piperidin-4-amine

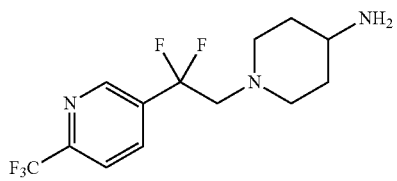 [SMILES: NC1CCN(CC(F)(F)c2ccc(C(F)(F)F)nc2)CC1]

To the solution of tert-butyl 1-(2,2-difluoro-2-(6-(trifluoromethyl)pyridin-3-yl)ethyl)-piperidin-4-ylcarbamate (1.36 g, 3.32 mmol) in DCM (16 ml) was added TFA (8 ml) at ice-water bath temperature. After stirring for 30 mins at rt, the starting material was consumed, and the mixture was concentrated. The concentrate was basified with 1M NaOH, and extracted with EtOAc. The organic phase was washed with brine, dried Na$_2$SO$_4$, and concentrated to afford the title compound as a white solid (1.0 g, 100%). MS (ESI) calcd for $C_{13}H_{16}F_5N_3$: 309.1; found: 310.3[M+H]. $^1$H NMR (400 MHz, CD$_3$OD) δ 8.92 (s, 1H), 8.24 (d, J=8.2 Hz, 1H), 7.95 (d, J=8.2 Hz, 1H), 3.16 (t, J=13.5 Hz, 2H), 3.06-2.94 (m, 1H), 2.87 (m, 2H), 2.43 (m, 2H), 1.88 (m, 2H), 1.50 (m, 2H), 1.33 (m, 2H).

Step 7: N-(1-(2,2-difluoro-2-(6-(trifluoromethyl)
pyridin-3-yl)ethyl)piperidin-4-yl)-3-methyl-1-(tetra-
hydro-2H-pyran-2-yl)-1H-pyrazolo[3,4-d]pyrimidin-
4-amine

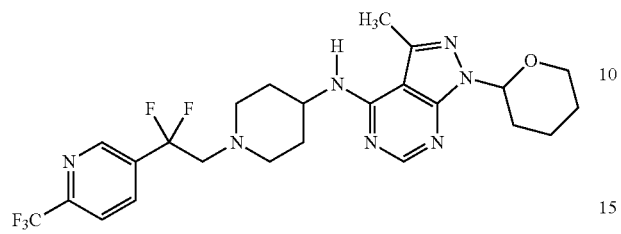

To a solution of 1-(2,2-difluoro-2-(6-(trifluoromethyl)
pyridin-3-yl)ethyl)piperidin-4-amine (300 mg, 0.97 mmol)
in i-PrOH (4 mL) was added 4-chloro-3-methyl-1-(tetra-
hydro-2H-pyran-2-yl)-1H-pyrazolo[3,4-d]pyrimidine (204
mg, 0.81 mmol), and DIPEA (0.28 ml, 1.62 mmol) under
nitrogen. The mixture was heated to 85° C. overnight. The
solution was concentrated and purified by column chroma-
tography over silica gel (hexane/EtOAc=2/1) to afford the
title compound as a white solid (366 mg, 86%). MS (ESI)
calcd for $C_{24}H_{28}F_5N_7O$: 525.2; found: 526.6[M+H]. $^1$H
NMR (400 MHz, $CDCl_3$) δ 8.95 (s, 1H), 8.35 (s, 1H), 8.04
(d, J=8.1 Hz, 1H), 7.77 (d, J=8.1 Hz, 1H), 5.90-5.85 (m, 1H),
4.98 (d, J=7.8 Hz, 1H), 4.26-4.16 (m, 1H), 3.84-3.72 (m,
1H), 3.03 (t, J=13.2 Hz, 2H), 2.84-2.78 (m, 2H), 2.62 (s,
3H), 2.58-2.47 (m, 3H), 2.10-2.00 (m, 3H), 1.88-1.82 (m,
1H), 1.81-1.70 (m, 2H), 1.50-1.45 (m, 3H).

Step 8: N-(1-(2,2-difluoro-2-(6-(trifluoromethyl)
pyridin-3-yl)ethyl)piperidin-4-yl)-3-methyl-1H-pyra-
zolo[3,4-d]pyrimidin-4-amine

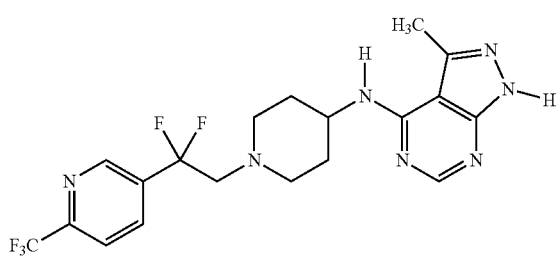 [SMILES: Cc1n[nH]c2ncnc(NC3CCN(CC(F)(F)c4ccc(C(F)(F)F)nc4)CC3)c12]

To the solution of N-(1-(2,2-difluoro-2-(6-(trifluorom-
ethyl)pyridin-3-yl)ethyl)piperidin-4-yl)-3-methyl-1-(tetra-
hydro-2H-pyran-2-yl)-1H-pyrazolo[3,4-d]pyrimidin-4-
amine (366 mg, 0.70 mmol) in MeOH (25 mL) was added
HCl/$Et_2O$ (2 M, 10 mL) at rt. After stirring for 4 hours, the
mixture was concentrated and taken up in EtOAc. The
organic phase was washed with saturated sodium bicarbon-
ate and brine, dried over anhydrous $Na_2SO_4$ and concen-
trated under reduced pressure to afford the title compound as
a white solid (279 mg, 98%). MS (ESI) calcd for
$C_{19}H_{20}F_5N_7$: 441.2; found: 442.5[M+H]. $^1$H NMR (400
MHz, $CD_3OD$) δ 8.96 (s, 1H), 8.26 (d, J=8.2 Hz, 1H), 8.19
(s, 1H), 7.95 (d, J=8.2 Hz, 1H), 4.25-4.15 (m, 1H), 3.17 (t,
J=13.6 Hz, 2H), 2.95-2.86 (m, 2H), 2.62 (s, 3H), 2.55-2.46
(m, 2H), 1.96-1.90 (m, 2H), 1.72-1.62 (m, 2H).

Example 1.142a (HCl salt)

N-(1-(2,2-difluoro-2-(6-(trifluoromethyl)pyridin-3-
yl)ethyl)-piperidin-4-yl)-3-methyl-1H-pyrazolo[3,4-
d]pyrimidin-4-amine hydrochloride (C-142.HCl)

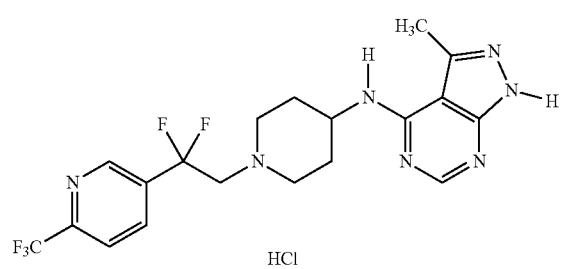 [SMILES: Cc1n[nH]c2ncnc(NC3CCN(CC(F)(F)c4ccc(C(F)(F)F)nc4)CC3)c12 ; Cl]

To the solution of N-(1-(2,2-difluoro-2-(6-(trifluorom-
ethyl)pyridin-3-yl)ethyl)piperidin-4-yl)-3-methyl-1H-pyra-
zolo[3,4-d]pyrimidin-4-amine (265 mg, 0.60 mmol) in
MeOH (3.0 mL) was added HCl/$Et_2O$ (2 M, 0.30 mL, 0.60
mmol) at rt. After stirring for 15 min, the mixture was
concentrated to afford the title compound as a white solid
(289 mg, 100%). MS (ESI) calcd for $C_{19}H_{20}F_5N_7$: 441.2;
found: 442.5[M+H]. $^1$H NMR (400 MHz, $CD_3OD$) δ 8.85
(s, 1H), 8.26 (s, 1H), 8.15 (d, J=8.1 Hz, 1H), 7.85 (d, J=8.1
Hz, 1H), 4.26 (brs, 1H), 3.16 (m, 2H), 2.92-2.88 (m, 2H),
2.62 (s, 3H), 2.55-2.48 (m, 2H), 1.90-1.86 (m, 2H), 1.75-
1.68 (m, 2H).

Example 2

Assays

Example 2.1

NR2B Antagonist Activity

HEK293 cell lines stably expressing cloned human NR1/
NR2B and NR1/NR2A, respectively, were established
according to standard previously described methods (Han-
sen et al., *Comb. Chem High Throughput Screen.* 11:304,
2008). Activation of the NR2A or NR2B subtype of NMDA
receptor with glutamate as an agonist and glycine co-agonist
on these cells results in calcium influx, which can be
monitored with fluorescent indicator Fluo-4. A cell based
assay has been implemented to evaluate the effect of a
compound on NR2A and NR2B receptors by measuring the
fluorescent changes (Hansen et al., *Comb. Chem High
Throughput Screen.* 11:304, 2008).

HEK293 cells stably expressing NR2A or NR2B recep-
tors were cultured at 37° C. in a humidified $CO_2$ incubator
in DMEM supplemented with 10% fetal bovine serum
(FBS) (Hyclone), 10 μM MK801 (Sigma-Aldrich) and 50
μM AP-5 (Tocris). For experiments, the cells were seeded
onto poly-D-lysine-coated 96-well black plates with clear
bottom (Corning) at a density of ~50,000 cells/well. After
overnight culture, the growth medium was removed from
the wells and the cells were incubated at 37° C. for 60 min
in Hanks buffer containing 4 μM fluo-4-AM (Invitrogen)
and 0.1% bovine serum albumin (BSA). After dye-loading,
the cells were washed three times with Hanks buffer and
incubated for 10 min at room temperature with various
concentrations of test compounds prepared in Hanks buffer
with 0.1% BSA. The cell plates were placed onto FDSS µCell fluorescence reader (Hamamatsu). After 20 sec reading of background fluorescence, agonist glutamate at final 100 µM and co-agonist glycine at final 50 µM were added to the cells to activate the receptor, and the resulting fluorescence changes were recorded and quantified. Based on the changes in fluorescence intensity, the pharmacological effect of test compounds were analyzed and the $IC_{50}$ values derived from a non-linear least squares fitting of the concentration-dependent response to a standard logistic equation using Prism (Graphpad, Inc):

Amplitude=Max Amplitude/(1+(IC50/[antagonist])$^n$).

Results are shown in the table below.

| compound | NR2B $IC_{50}$ | NR2A $IC_{50}$ |
|---|---|---|
| C-1 | 178 nM | >10 µM |
| C-3 | 26 nM | >10 µM |
| C-4 | 52 nM | >10 µM |
| C-5 | 32 nM | >10 µM |
| C-6 | 34 nM | >10 µM |
| C-7 | 43 nM | >10 µM |
| C-11 | 28 nM | >10 µM |
| C-12 | 23 nM | >10 µM |
| C-15 | 93 nM | >10 µM |
| C-16 | 30 nM | >10 µM |
| C-17 | 48 nM | >10 µM |
| C-18 | 59 nM | >10 µM |
| C-24 | 52 nM | >10 µM |
| C-33 | 110 nM | >10 µM |
| C-127 | 38 nM | >10 µM |
| C-142 | 89 nM | >10 µM |

Example 2.2 hERG Channel Inhibition

The assay was performed on hERG channel stably expressed in HEK293 cells. The cells were cultured at 37° C. in a humidified $CO_2$ incubator in the growth medium consisting of DMEM, 10% fetal bovine serum and antibiotics. Prior to the assay, the cells were seeded onto a 12 mm PDL-coated glass coverslip and cultured in a 35 mm Petri dish. After 16 to 40 hr culture, the cover slip was transferred into the chamber of OctaFlow perfusion system (ALA Instrument) and under a constant flow of extracellular solution (140 mM NaCl, 4 M KCl, 1 mM $MgCl_2$, 1 mM $CaCl_2$, 10 mM HEPES, 10 mM D-glucose, pH 7.35, osmolarity 290). Whole cell patch clamping was performed with a glass micropipette filled with intracellular solution (120 mM KCl, 1.75 mM $MgCl_2$, 10 mM HEPES, 10 mM EGTA, and 4 mM ATP-$K_2$, PH 7.2, osmolarity 300). Giga-seal was maintained during the test. The voltage control and current measurement were carried out using Axon amplifier 700B, Digidata 1440A and CLAMPEX10 software (Molecular Devices). Whole-cell hERG currents were recorded following the Petroski protocol: the cell was held at −80 mV, and the voltage step jumped from −80 to 30 mV and stay for 2 sec with a 20 ms prepulse at −40 mV. After depolarization, the voltage was decreased to −40 mV and stay for 2 sec, and returned back to −80 mV. Test compound was applied by quartz capillary tubes tip (200 µm inner diameter), and the flow rate was controlled at 2-3 ml/min with OctaFlow perfusion system. Different concentrations of the compound were applied to the cells for 5 min and the hERG current was measured three times before, during and after compound treatment. The data were analyzed using Clampfit 10 software (Molecular Devices). Results are shown in the table below.

| compound | NR2B $IC_{50}$ | hERG $IC_{50}$ |
|---|---|---|
| LX-1 | 24 nM | 4.5 µM |
| C-5 | 32 nM | 31 µM |
| C-16 | 30 nM | 13 µM |
| C-18 | 59 nM | 12 µM |
| C-33 | 89 nM | >30 µM |
| C-127 | 38 nM | 23 µM |

Example 2.3

CYP P450 Enzyme Inhibition

Inhibitory activities of test compounds on 5 major isoforms of CYP P450 were evaluated by using pooled human liver microsome (HLM, purchased from BD Gentest) and selective substrates for those isoforms. Those CYP isoforms and their corresponding probe substrates are as follows: CYP1A2 (phenacetin, 30 µM), CYP2C9 (tolutamide, 100 µM), CYP2C19 (S-mephenytoin, 40 µM), CYP2D6 (dextromethorphan, 5 µM) and CYP3A4 (midazolam, 1 µM). All probe substrates were used at concentrations near or below their $K_{ms}$. For experiment, a reaction mixture of test compound at 10 uM or in serial dilution, CYP probe substrate described above and 0.2 mg/mL pooled HLM in phosphate buffer, pH 7.4 in a final volume of 200 µL was pre-incubated at 37° C. for 10 minutes in triplicate. The reaction was initiated by addition of NADPH at final concentration of 1 mM. The reaction was terminated after 10 minutes (CYP1A2, CYP2D6 and CYP3A4) or 30 minutes (CYP2C9 and CYP2C19) by addition of 100 µL ice-cold acetonitrile with internal standard (IS). The samples were then centrifuged at 13,000 rpm and the supernatants were injected to LC-MS/MS (Agilent Technologies) to quantify the concentration of the specific metabolites of the probe substrates formed by individual CYP450 isoforms. The inhibition ratio is calculated as:

$(M_t-M_0)/M_{water} \times 100\%$ in which $M_t$ and $M_0$ represent the concentrations of the specific probe substrate metabolite, which was formed by individual CYP450 isoform, at the beginning and end of the reaction in the presence of test compound; while $M_{water}$ represents the concentration of the specific metabolite at the end of the reaction in the absence of test compound. Data are presented as mean±SD (n=3). For titration of test compound activity on a specific CYP450 isoform, the concentration-dependent response was plotted and an $IC_{50}$ value calculated. Results are shown in the table below.

| compound | NR2B $IC_{50}$ | CYP 2D6 $IC_{50}$ |
|---|---|---|
| LX-1 | 24 nM | 1.0 µM |
| C-16 | 30 nM | 10.0 µM |
| C-18 | 59 nM | 11.5 µM |
| C-127 | 38 nM | 2.4 µM |

Example 2.4

Forced Swim Test

The forced swim test was used to evaluate antidepressant activity (Porsolt et al., 1977 *Arch. Int. Pharmacodyn.* 229:

327-336). Mice that are forced to swim in a situation from which they cannot escape, rapidly become immobile. Drugs with antidepressant activity, such as imipramine, reduce the amount of time spent in the immobile state. Therefore, the amount of immobility time during a test conducted after drug administration represents a useful indicator of antidepressant activity (Lucki et el., 2001, *Psychopharmacology* 155:315-322).

Male mice (strain NLMN) weighing 25-35 g were used for testing. All animals were housed in a temperature (22-24° C.) and humidity (50-60%) controlled environment with free access to food and water on a 12-hour light-dark cycle. Test compounds were dissolved in 0.5% dimethylsulfoxide, 4% hydroxypropyl-b-cyclodextrin water to generate the appropriate dosing solution. Drugs were administered by intraperitoneal injection at a dose volume of 10 mL/kg. Testing was initiated 20-60 minutes after dosing. Testing for antidepressant activity was conducted as described by Darci et al. (Darci et al., 2004, *Eur. J. Pharmacol.* 499:135-146). Mice were placed in a white plastic cylinder 20 cm high with a diameter of 21 cm containing 10 cm of water at 25±2° C. The mice were videotaped for 6 minutes, and the last 4 minutes of video were analyzed by a blinded observer off-line. The observer judged the animal to be immobile when it ceased all activity (struggling, swimming, jumping etc.) and floated passively atop the water. The amount of time each animal spent in the immobile state was recorded and used for statistical analysis of compound effect. Group differences were evaluated by student's t-test or one-way ANOVA followed by post-hoc Dunnett's test.

Figure 2:
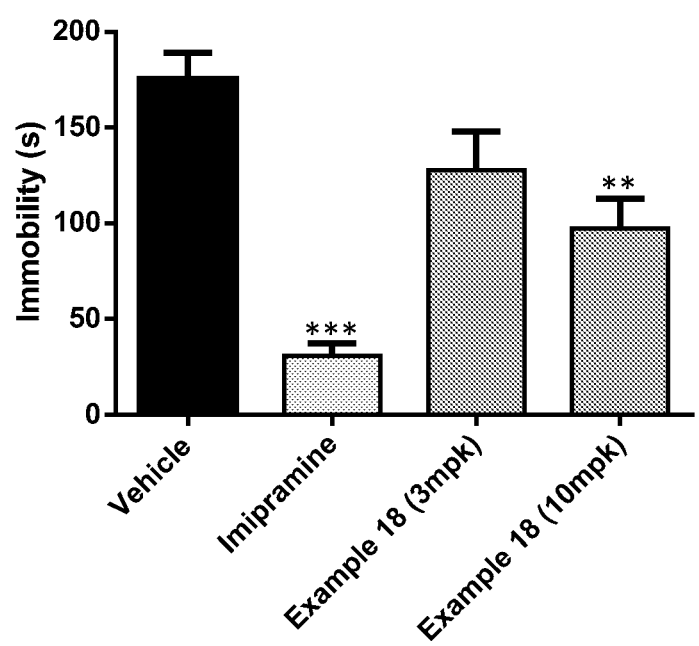
FIG. 2 shows the results of the forced swim test as described in Example 2.4.2.

In both Examples 2.4.1 and 2.4.2, the positive control compound, imipramine (32 mg/kg, IP) showed the expected antidepressant activity (see FIGS. 1 and 2). These results indicate that provided compounds exhibit antidepressant activity when tested in a standard model for human depression.

Example 2.4.1

Compound C-5

Compound C-5 significantly reduced immobility from 188±6.6 seconds observed in the vehicle group to 111±18.3 and 89±14.4 seconds observed in the groups treated with 3 mg/kg (n=10, p<0.05) and 10 mg/kg (n=9, p<0.01) respectively. Results are shown in FIG. 1 (in which C-5 is labeled "Example 5"): Bars represent the mean±SEM immobility time for each dose group (n=10, */: different from vehicle group, p<0.001/0.01 respectively, One-way ANOVA, Dunnett's post-test). Doses are given as milligram per kilogram (mpk). The dose of imipramine was 32 mpk.

Example 2.4.2

Compound C-18

Compound C-18 was effective in the forced swim test when administered at 10 mg/kg 20 minutes after IP dosing (immobility time=97±16 seconds versus 175±14 seconds in the vehicle group, n=10, p<0.01). Results are shown in FIG. 2 (in which C-18 is labeled "Example 18"): Bars represent the mean±SEM immobility time for each study group (n=10, */: different from vehicle group, p<0.001/0.01 respectively, One-way ANOVA, Dunnett's post-test). Doses are given as milligram per kilogram (mpk). The dose of imipramine was 32 mpk.

What is claimed is:

1. A chemical entity of formula I:

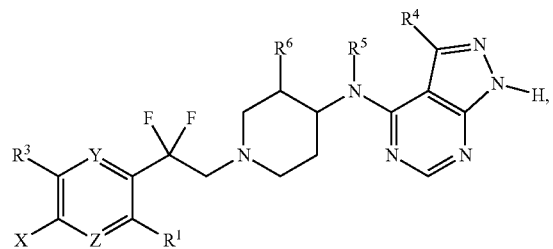

I wherein:

one of Y and Z is N, and the other is $C(R^2)$;

X is hydrogen, halogen, $C_1$-$C_6$ alkyl, $C_3$-$C_6$ cycloalkyl, $C_1$-$C_4$ alkoxy, —$CO_2R^7$, —CN, —$SR^7$, —$S(O)_2R^7$, —$NO_2$, or —$N(R^7)(R^8)$, wherein said $C_1$-$C_6$ alkyl is optionally substituted with one to six fluorine atoms and said $C_1$-$C_4$ alkoxy is optionally substituted with one to six fluorine atoms;

$R^1$ is hydrogen, halogen, $C_1$-$C_4$ alkyl, $C_1$-$C_4$ alkoxy, —CN, —$NO_2$, —$N(R^7)(R^8)$, —$CO_2R^7$, —$C(O)N(R^7)(R^8)$ or $C_3$-$C_6$ cycloalkyl, wherein said $C_1$-$C_4$ alkyl is optionally substituted with one to three fluorine atoms and said $C_1$-$C_4$ alkoxy is optionally substituted with one to three fluorine atoms;

$R^2$ is hydrogen, halogen, $C_1$-$C_4$ alkyl, cyclopropyl or $C_1$-$C_4$ alkoxy wherein said $C_1$-$C_4$ alkyl is optionally substituted with one to three fluorine atoms and said $C_1$-$C_4$ alkoxy is optionally substituted with one to three fluorine atoms;

$R^3$ is hydrogen, —F, —Cl, —$CH_3$, —$CF_3$ or —$OCH_3$;

$R^4$ is hydrogen, —F, —Cl, $C_1$-$C_3$ alkyl or cyclopropyl, wherein said $C_1$-$C_3$ alkyl is optionally substituted with one to three fluorine atoms;

$R^5$ is hydrogen or —$CH_3$;

$R^6$ is hydrogen, —F or —$CH_3$;

each instance of $R^7$ independently is $C_1$-$C_4$ alkyl; and each instance of $R^8$ independently is hydrogen or $C_1$-$C_4$ alkyl.

2. The chemical entity of claim 1, which is a chemical entity selected from formulae (II), (III), IV, V, VI and VII:

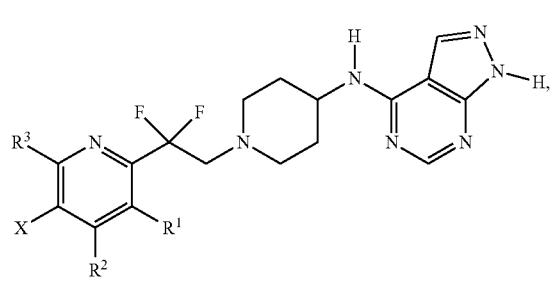

II

-continued

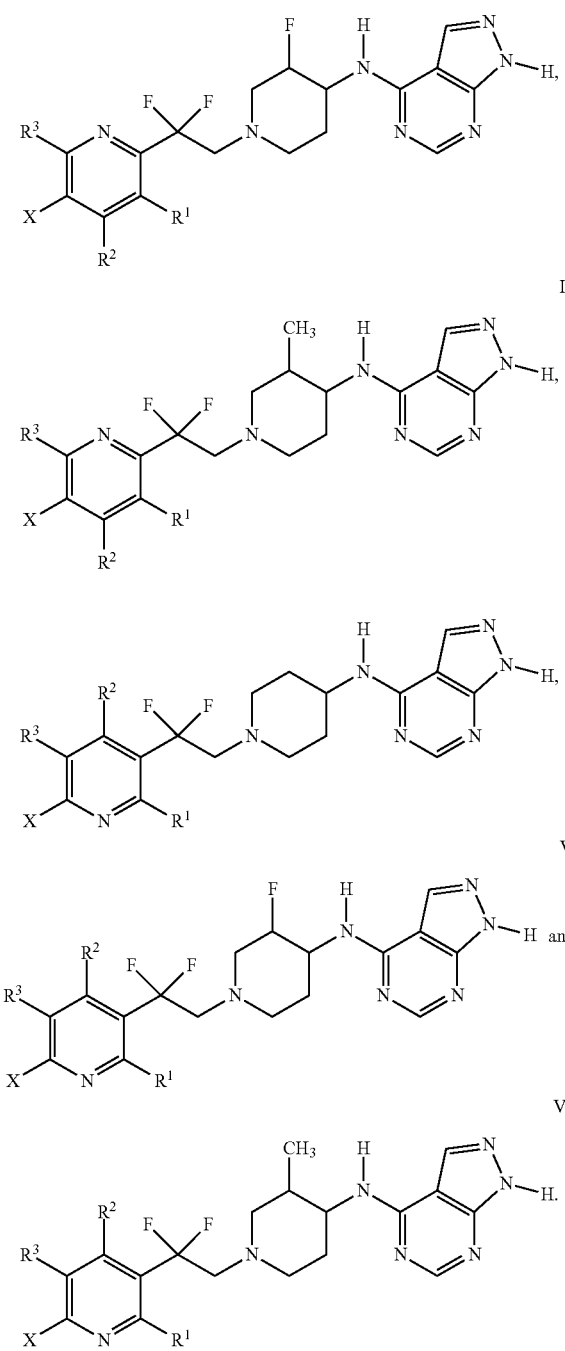

3. The chemical entity of claim 2, wherein:

X is hydrogen, —CN, —SCH₃, —SO₂CH₃, —SO₂CF₃, —NO₂, —N(CH₃)₂, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, —OCH₃, —OCF₃, —OCHF₂, —OCFH₂ or cyclopropyl;

R¹ is hydrogen, —F, —Cl, —CH₃, —CH₂CH₃, —CH(CH₃)₂, —CF₃, —OCH₃, —OCF₃, —OCHF₂, —OCFH₂, —CN, —NO₂, —CO₂CH₃, —CO₂CH₂CH₃, —C(O)N(CH₃)₂, —C(O)NH(CH₃) or cyclopropyl;

R² is hydrogen, —F, —Cl, —CH₃, —CH₂CH₃, —CH(CH₃)₂, —CF₃, cyclopropyl, —OCH₃, —OCF₃, —OCHF₂ or —OCFH₂; and R³ is hydrogen —F, —Cl, —CH₃, —CF₃ or —OCH₃.

4. The chemical entity of claim 1, which is a chemical entity selected from formulae (IIa), (IIIa), (IIIb), (IVa) and (IVb):

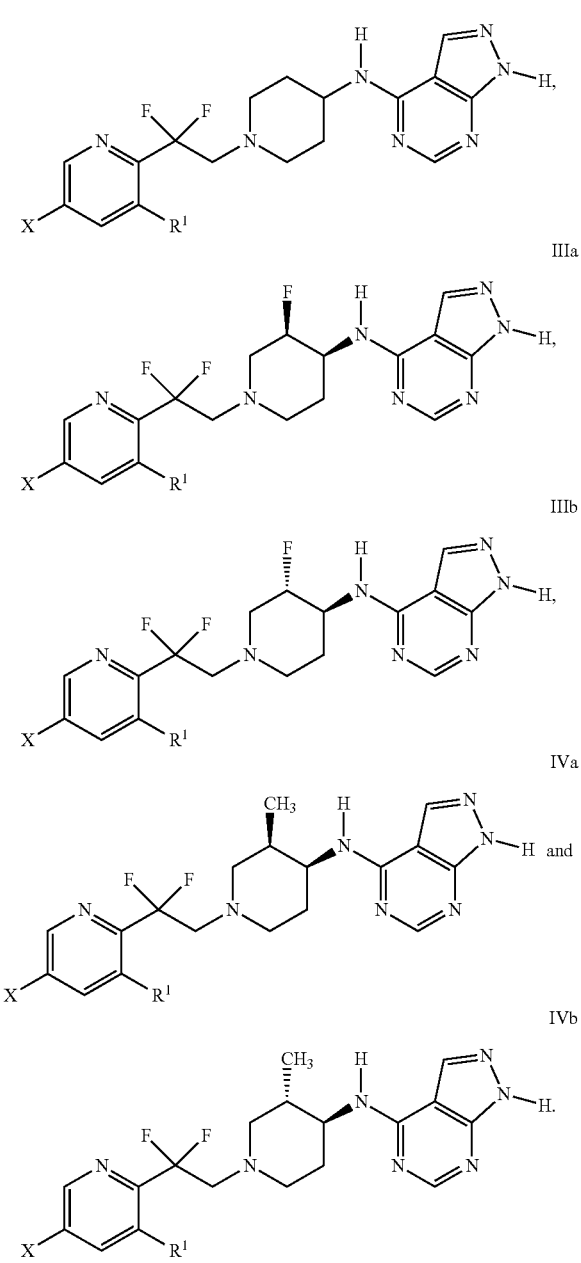

5. The chemical entity of claim 4, wherein:

X is hydrogen, —CN, —SCH₃, —SO₂CH₃, —SO₂CF₃, —NO₂, —N(CH₃)₂, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, —OCH₃, —OCF₃, —OCHF₂, —OCFH₂ or cyclopropyl; and R¹ is hydrogen, —F, —Cl, —CH₃, —CH₂CH₃, —CH(CH₃)₂, —CF₃, —OCH₃, —OCF₃, —OCHF₂, —OCFH₂, —CN, —NO₂, —CO₂CH₃, —CO₂CH₂CH₃, —C(O)N(CH₃)₂, —C(O)NH(CH₃) or cyclopropyl.

6. The chemical entity of claim 1, which is a chemical entity selected from formulae (Va), (VIa), (VIb), (VIIa) and (VIIb):

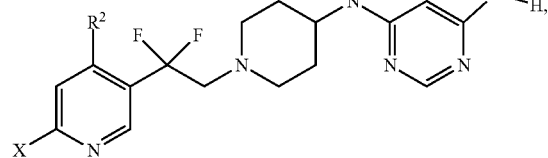

Va

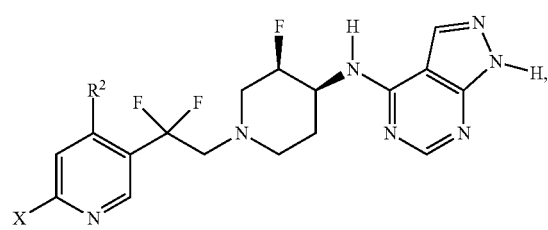

VIa

VIb

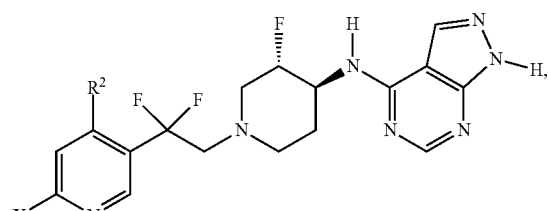

VIIa

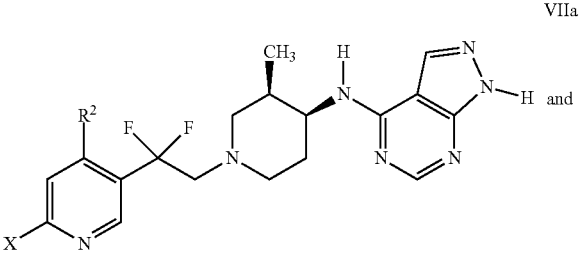

and

VIIb

7. The chemical entity of claim 6, wherein:

X is hydrogen, —CN, —SCH₃, —SO₂CH₃, —SO₂CF₃, —NO₂, —N(CH₃)₂, —F, —Cl, —CH₃, —CH₂CH₃, —CH(CH₃)₂, —CF₃, —CHF₂, —CH₂F, —CF₂CF₃, —CH(CF₃)₂, —CH₂CF₂CF₃, —OCH₃, —OCF₃, —OCHF₂, —OCFH₂ or cyclopropyl; and R² is hydrogen, —F, —Cl, —CH₃, —CH₂CH₃, —CH(CH₃)₂, —CF₃, cyclopropyl, —OCH₃, —OCF₃, —OCHF₂ or —OCFH₂.

8. The chemical entity of claim 1 selected from the group consisting of:

TABLE 1.C

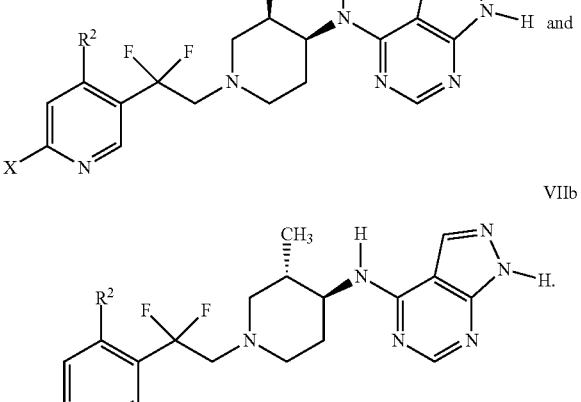

| compound | X | R¹ |
|---|---|---|
| C-1 | H | H |
| C-2 | F | H |
| C-3 | Cl | H |
| C-4 | CH₃ | H |
| C-5 | CF₃ | H |
| C-6 | CF₂H | H |
| C-7 | CH₂F | H |
| C-8 | CH₂CH₃ | H |
| C-9 | cyclopropyl | H |
| C-10 | CH₃O | H |
| C-11 | CF₃O | H |
| C-12 | CHF₂O | H |
| C-13 | SCH₃ | H |
| C-14 | CN | H |
| C-15 | F | F |
| C-16 | Cl | F |
| C-17 | CH₃ | F |
| C-18 | CF₃ | F |
| C-19 | CF₂H | F |
| C-20 | CH₂F | F |
| C-21 | CH₂CH₃ | F |
| C-22 | cyclopropyl | F |
| C-23 | F | Cl |
| C-24 | Cl | Cl |
| C-25 | CH₃ | Cl |
| C-26 | CF₃ | Cl |
| C-27 | cyclopropyl | Cl |
| C-28 | F | CH₃ |
| C-29 | Cl | CH₃ |
| C-30 | CH₃ | CH₃ |
| C-31 | CF₃ | CH₃ |
| C-32 | cyclopropyl | CH₃ |

TABLE 2.C

| compound | X | R¹ | R⁴ | R⁵ |
|---|---|---|---|---|
| C-33 | CF₃ | H | CH₃ | H |
| C-34 | Cl | H | CH₃ | H |
| C-35 | CH₃ | H | CH₃ | H |
| C-36 | CF₃ | H | Cl | H |
| C-37 | Cl | H | Cl | H |
| C-38 | CH₃ | H | Cl | H |
| C-39 | CF₃ | F | CH₃ | H |
| C-40 | Cl | F | CH₃ | H |
| C-41 | CH₃ | F | CH₃ | H |
| C-42 | CF₃ | F | Cl | H |
| C-43 | Cl | F | Cl | H |

TABLE 2.C-continued

| compound | X | R¹ | R⁴ | R⁵ |
|---|---|---|---|---|
| C-44 | CH₃ | F | Cl | H |
| C-45 | CF₃ | H | H | CH₃ |
| C-46 | Cl | H | H | CH₃ |
| C-47 | CH₃ | H | H | CH₃ |

TABLE 3.C

| compound | X | R² | R³ |
|---|---|---|---|
| C-48 | F | F | H |
| C-49 | Cl | F | H |
| C-50 | CH₃ | F | H |
| C-51 | CF₃ | F | H |
| C-52 | F | CH₃ | H |
| C-53 | Cl | CH₃ | H |
| C-54 | CH₃ | CH₃ | H |
| C-55 | CF₃ | CH₃ | H |
| C-56 | F | Cl | H |
| C-57 | Cl | Cl | H |
| C-58 | CH₃ | Cl | H |
| C-59 | CF₃ | Cl | F |
| C-60 | F | H | F |
| C-61 | Cl | H | F |
| C-62 | CH₃ | H | F |
| C-63 | CF₃ | H | Cl |
| C-64 | F | H | Cl |
| C-65 | Cl | H | Cl |
| C-66 | CH₃ | H | Cl |
| C-67 | CF₃ | H | CH₃ |
| C-68 | F | H | CH₃ |
| C-69 | Cl | H | CH₃ |
| C-70 | CH₃ | H | CH₃ |

TABLE 4.C

| compound | X | R¹ | R⁶ |
|---|---|---|---|
| C-71 | F | H | CH₃ |
| C-72 | Cl | H | CH₃ |
| C-73 | CH₃ | H | CH₃ |
| C-74 | CF₃ | H | CH₃ |
| C-75 | CF₂H | H | CH₃ |
| C-76 | CH₂F | H | CH₃ |
| C-77 | OCF₃ | H | CH₃ |
| C-78 | OCF₂H | H | CH₃ |
| C-79 | CH₂CH₃ | H | CH₃ |
| C-80 | cyclopropyl | H | CH₃ |
| C-81 | F | H | F |
| C-82 | Cl | H | F |
| C-83 | CH₃ | H | F |
| C-84 | CF₃ | H | F |
| C-85 | CF₂H | H | F |
| C-86 | CH₂F | H | F |
| C-87 | OCF₃ | H | F |
| C-88 | OCF₂H | H | F |
| C-89 | CH₂CH₃ | H | F |
| C-90 | cyclopropyl | H | F |
| C-91 | F | F | CH₃ |
| C-92 | Cl | F | CH₃ |
| C-93 | CH₃ | F | CH₃ |
| C-94 | CF₃ | F | CH₃ |
| C-95 | F | F | F |
| C-96 | Cl | F | F |
| C-97 | CH₃ | F | F |
| C-98 | CF₃ | F | F |

TABLE 5.C

| compound | X | R¹ | R⁶ |
|---|---|---|---|
| C-99 | F | H | CH₃ |
| C-100 | Cl | H | CH₃ |
| C-101 | CH₃ | H | CH₃ |
| C-102 | CF₃ | H | CH₃ |
| C-103 | CF₂H | H | CH₃ |
| C-104 | CH₂F | H | CH₃ |
| C-105 | OCF₃ | H | CH₃ |
| C-106 | OCF₂H | H | CH₃ |
| C-107 | CH₂CH₃ | H | CH₃ |
| C-108 | cyclopropyl | H | CH₃ |
| C-109 | F | H | F |
| C-110 | Cl | H | F |
| C-111 | CH₃ | H | F |
| C-112 | CF₃ | H | F |
| C-113 | CF₂H | H | F |
| C-114 | CH₂F | H | F |
| C-115 | OCF₃ | H | F |
| C-116 | OCF₂H | H | F |
| C-117 | CH₂CH₃ | H | F |
| C-118 | cyclopropyl | H | F |

TABLE 5.C-continued

| compound | X | R¹ | R⁶ |
|---|---|---|---|
| C-119 | F | F | CH₃ |
| C-120 | Cl | F | CH₃ |
| C-121 | CH₃ | F | CH₃ |
| C-122 | CF₃ | F | CH₃ |
| C-123 | F | F | F |
| C-124 | Cl | F | F |
| C-125 | CH₃ | F | F |
| C-126 | CF₃ | F | F |

TABLE 6.C

| compound | X | R¹ | R² | R³ |
|---|---|---|---|---|
| C-127 | CF₃ | H | H | H |
| C-128 | CH₃ | H | H | H |
| C-129 | F | H | H | H |
| C-130 | Cl | H | H | H |
| C-131 | OCH₃ | H | H | H |
| C-132 | OCF₃ | H | H | H |
| C-133 | SCH₃ | H | H | H |
| C-134 | CH₂CH₃ | H | H | H |
| C-135 | cyclopropyl | H | H | H |
| C-136 | CF₃ | F | H | H |
| C-137 | CF₃ | H | F | H |
| C-138 | CF₃ | H | H | F |
| C-139 | H | CF₃ | H | H |
| C-140 | H | H | CF₃ | H |
| C-141 | H | H | H | CF₃ |

TABLE 7.C

| compound | X | R⁴ | R⁶ |
|---|---|---|---|
| C-142 | CF₃ | CH₃ | H |
| C-143 | CH₃ | CH₃ | H |
| C-144 | CF₃ | H | F |
| C-145 | CH₃ | H | F |
| C-146 | CH₂CH₃ | H | F |

TABLE 7.C-continued

| compound | X | R⁴ | R⁶ |
|---|---|---|---|
| C-147 | SCH₃ | H | F |
| C-148 | cyclopropyl | H | F |
| C-149 | OCF₃ | H | F |
| C-150 | OCH₃ | H | F |
| C-151 | CF₃ | H | CH₃ |
| C-152 | CH₃ | H | CH₃ |
| C-153 | CH₂CH₃ | H | CH₃ |
| C-154 | SCH₃ | H | CH₃ |
| C-155 | cyclopropyl | H | CH₃ |
| C-156 | OCF₃ | H | CH₃ |
| C-157 | OCH₃ | H | CH₃ |

TABLE 8.C

| compound | X | R⁴ | R⁶ |
|---|---|---|---|
| C-158 | CF₃ | Cl | H |
| C-159 | CH₃ | Cl | H |
| C-160 | CF₃ | H | F |
| C-161 | CH₃ | H | F |
| C-162 | CH₂CH₃ | H | F |
| C-163 | SCH₃ | H | F |
| C-164 | cyclopropyl | H | F |
| C-165 | OCF₃ | H | F |
| C-166 | OCH₃ | H | F |
| C-167 | CF₃ | H | CH₃ |
| C-168 | CH₃ | H | CH₃ |
| C-169 | CH₂CH₃ | H | CH₃ |
| C-170 | SCH₃ | H | CH₃ |
| C-171 | cyclopropyl | H | CH₃ |
| C-172 | OCF₃ | H | CH₃ |
| C-173 | OCH₃ | H | CH₃. |

9. A pharmaceutical composition comprising the chemical entity of claim 1 and a pharmaceutically acceptable carrier.

10. The pharmaceutical composition of claim 9, wherein the composition is formulated for oral administration.

11. A pharmaceutical composition comprising the chemical entity of claim 2 and a pharmaceutically acceptable carrier.

12. A pharmaceutical composition comprising the chemical entity of claim 4 and a pharmaceutically acceptable carrier.

13. A pharmaceutical composition comprising the chemical entity of claim 6 and a pharmaceutically acceptable carrier.

14. A pharmaceutical composition comprising the chemical entity of claim 8 and a pharmaceutically acceptable carrier.

15. A method of treating a disease or disorder responsive to NR2B antagonism in a subject in need of such treatment, comprising administering an effective amount of the chemical entity of claim 1.

16. The method of claim 15, wherein the disease or disorder is depression, a seizure disorder, pain, Parkinson's disease, Huntington's disease, cerebral ischaemia, traumatic brain injury, or migraine.

17. The method of claim 15, wherein the disease or disorder is depression.

18. A method of treating a disease or disorder responsive to NR2B antagonism in a subject in need of such treatment, comprising administering an effective amount of the chemical entity of claim 8.

19. The method of claim 18, wherein the disease or disorder is depression, a seizure disorder, pain, Parkinson's disease, Huntington's disease, cerebral ischaemia, traumatic brain injury, or migraine.

20. The method of claim 19, wherein the disease or disorder is depression.

* * * * *